US010087261B2

(12) United States Patent
Beasley et al.

(10) Patent No.: US 10,087,261 B2
(45) Date of Patent: Oct. 2, 2018

(54) SOLUBLE POLYPEPTIDES

(71) Applicant: Affinity Biosciences Pty Ltd, Scoresby (AU)

(72) Inventors: Matthew David Beasley, Fitzroy North (AU); Keith Philip Niven, Forest Hill (AU); Ben Ross Kiefel, MItcham (AU)

(73) Assignee: Affinity Biosciences Pty Ltd, Scoresby, Victoria (AU)

( * ) Notice: Subject to any disclaimer, the term of this patent is extended or adjusted under 35 U.S.C. 154(b) by 600 days.

(21) Appl. No.: 14/181,026

(22) Filed: Feb. 14, 2014

(65) Prior Publication Data
US 2014/0234313 A1 Aug. 21, 2014

Related U.S. Application Data

(63) Continuation of application No. PCT/AU2012/000970, filed on Aug. 17, 2012.

(30) Foreign Application Priority Data

Aug. 18, 2011 (AU) ................. 2011903298

(51) Int. Cl.
*C40B 40/08* (2006.01)
*C07K 16/46* (2006.01)
(Continued)

(52) U.S. Cl.
CPC .............. *C07K 16/46* (2013.01); *C07K 16/00* (2013.01); *C07K 16/44* (2013.01); *G01N 33/53* (2013.01);
(Continued)

(58) Field of Classification Search
None
See application file for complete search history.

(56) References Cited

U.S. PATENT DOCUMENTS 8,685,896 B2 4/2014 Enzelberger et al.
8,716,196 B2 5/2014 Fischer et al.
(Continued)

FOREIGN PATENT DOCUMENTS

JP 2003-518941 6/2013
WO WO 2001/49713 7/2001
(Continued)

OTHER PUBLICATIONS

Supplemental European Search Report for European Patent Application No. EP12824386.2. 7 pages.
(Continued)

*Primary Examiner* — Christian C Boesen
(74) *Attorney, Agent, or Firm* — Fish & Richardson P.C.

(57) ABSTRACT

The invention relates generally to polypeptides, such as antibody molecules, that demonstrate high stability and solubility. In particular, the invention relates to polypeptides comprising paired $V_L$ and $V_H$ domains that demonstrate soluble expression and folding in a reducing or intracellular environment. The invention also relates to polynucleotides encoding such polypeptides, to libraries of such polypeptides or polynucleotides, and to methods of using such polypeptides in research, diagnostic and therapeutic applications.

17 Claims, 16 Drawing Sheets

Specification includes a Sequence Listing.

IGLV1-51(aka DPL5) (SEQ ID NO: 15)
QSVLTQPPSVSAAPGQKVTISCSGSSSNIGNNYVSWYQQLPGTAPKLLIYDNNKRPSGIPDRFSGSKSGTSATLGITGLQTGDEADYYCGTWDSSLSAG IGLV1-40 (aka DPL6) (SEQ ID NO: 18)
QSVLTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGS IGLV1-44 (aka DPL2) (SEQ ID NO: 21)
QSVLTQPPSASGTPGQRVTISCSGSSSNIGSNTVNWYQQLPGTAPKLLIYSNNQRPSGVPDRFSGSKSGTSASLAISGLQSEDEADYYCAAWDDSLNGP IGV1-47 (aka DPL3) (SEQ ID NO: 24)
QSVLTQPPSASGTPGQRVTISCSGSSSNIGSNYVYWYQQLPGTAPKLLIYSNNQRPSGVPDRFSGSKSGTSASLAISGLRSEDEADYYCAAWDDSLSGP IGLV3-1 (aka DPL23) (SEQ ID NO: 6)
QSVLTQPPSVSVSPGQTASITCSGDKLGDKYACWYQQKPGQSPVLVIYQDSKRPSGIPERFSGSNSGNTATLTISGTQAMDEADYYCQAWDSSTA IGLV3-19 (SEQ ID NO: 27)
SSELTQDPAVSVALGQTVRITCQGDSLRSYYASWYQQKPGQAPVLVIYGKNNRPSGIPDRFSGSSSGNTASLTITGAQAEDEADYYCNSRDSSGNHL IGLV3-21 (SEQ ID NO: 9)
QSVLTQPPSVSVAPGQTARITCGGNNIGSKSVHWYQQKPGQAPVLVVYDDSDRPSGIPERFSGSNSGNTATLTISRVEAGDEADYYCQVWDSSSDHP IGLV6-57 (SEQ ID NO: 12)
NFMLTQPHSVSESPGKTVTISCTGSSGSIASNYVQWYQQRPGSAPTTVIYEDNQRPSGVPDRFSGSIDSSSNSASLTISGLKTEDEADYYCQSYDSSN IGHV3-23 (aka DP47) (SEQ ID NO: 3)
EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAK

(51) Int. Cl.
*C07K 16/00* (2006.01)
*C07K 16/44* (2006.01)
*G01N 33/68* (2006.01)
*G01N 33/53* (2006.01)

(52) U.S. Cl.
CPC ..... *G01N 33/6845* (2013.01); *G01N 33/6854* (2013.01); *C07K 2317/21* (2013.01); *C07K 2317/565* (2013.01); *C07K 2317/622* (2013.01); *C07K 2317/82* (2013.01); *C07K 2317/94* (2013.01); *C40B 40/08* (2013.01)

(56) References Cited

U.S. PATENT DOCUMENTS

| | | | |
|---|---|---|---|
| 8,735,331 | B2 | 5/2014 | Villa |
| 2010/0292103 | A1* | 11/2010 | Ladner ............... C07K 16/005 506/17 |
| 2011/0065610 | A1 | 3/2011 | Fischer et al. |
| 2011/0118149 | A1 | 5/2011 | Fischer |
| 2011/0236372 | A1 | 9/2011 | Villa |
| 2012/0077713 | A1 | 3/2012 | Enzelberger et al. |
| 2013/0023421 | A1 | 1/2013 | Beasley et al. |
| 2014/0121131 | A1 | 5/2014 | Beasley et al. |
| 2014/0163208 | A1 | 6/2014 | Enzelberger et al. |
| 2014/0234313 | A1 | 8/2014 | Beasley et al. |

FOREIGN PATENT DOCUMENTS

| | | |
|---|---|---|
| WO | 2003/097697 | 11/2003 |
| WO | WO2004003144 A3 | 6/2004 |
| WO | WO2010028791 A1 | 3/2010 |
| WO | 2010/054007 | 5/2010 |
| WO | WO2010136598 A1 | 12/2010 |
| WO | WO2011075761 A1 | 6/2011 |
| WO | 2011/118149 | 9/2011 |
| WO | 2013/000023 | 1/2013 |
| WO | 2013/023251 | 2/2013 |
| WO | 2014/128628 | 8/2014 |

OTHER PUBLICATIONS

Office Action for Australian Patent Application No. AU201297570. 4 pages.
Second Office Action for Australian Patent Application No. AU201297570. 7 pages.
International Search Report and Written Opinion for PCT Application No. PCT/IB2014/059107, filed Feb. 20, 2014. 7 pages.
Sharkey, R. M et al. "Improved Therapy by Pretargeted Radioimmunotherapy of Non-Hodgkin Lymphoma with a New Recombinant, Trivalent, Anti-CD20, Bispecific Antibody." Cancer Res, vol. 68, No. 13. Published Jul. 1, 2008. pp. 5282-5290.
De Marco, "Strategies for successful recombinant expression of disulfide bond-dependent proteins in *Escherichia coli*," Microbial Cell Factories (2009) 8:26, doi: 10.1186/1475-2859-8-26.
Denoncin and Collet, "Disulfide bond formation in the bacterial periplasm: major achievements and challenges ahead," Antioxidants & Redox Signaling (2013) 19(1):63-71.
Glockshuber et al., "The disulfide bonds in antibody variable domains: effects on stability, folding in vitro, and functional expression in *Escherichia coli*," Biochemistry (1992) 31(5): 1270-1279.
Natale et al., "Sec- and Tat-mediated protein secretion across the bacterial cytoplasmic membrane—distinct translocases and mechanisms," Biochimica et Biophysica Acta (2008) 1778:1735-1756.
Thie et al., "SRP and Sec pathway leader peptides for antibody phage display and antibody fragment production in *E. coli*," New Biotechnology (2008) 25(1):49-54.
Wörn and Plückthun, "An intrinsically stable antibody scFv fragment can tolerate the loss of both disulfide bonds and fold correctly," FEBS Letters (1998) 427:357-361.
Office Action for Japanese Application Serial No. JP 2014-525261, dated Jan. 17, 2017, 5 pages (with English translation).
International Search Report for International Application No. PCT/AU2012/000970, dated Oct. 23, 2012.

* cited by examiner

IGLV1-51 (aka DPL5) (SEQ ID NO: 15)
QSVLTQPPSVSAAPGQKVTISCSGSSSNIGNNYVSWYQQLPGTAPKLLIYDNNKRPSGIPDRFSGSKSGTSATLGITGLQTGDEADYYCGTWDSSLSAG IGLV1-40 (aka DPL6) (SEQ ID NO: 18)
QSVLTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGS IGLV1-44 (aka DPL2) (SEQ ID NO: 21)
QSVLTQPPSASGTPGQRVTISCSGSSSNIGSNTVNWYQQLPGTAPKLLIYSNNQRPSGVPDRFSGSKSGTSASLAISGLQSEDEADYYCAAWDDSLNGP IGV1-47 (aka DPL3) (SEQ ID NO: 24)
QSVLTQPPSASGTPGQRVTISCSGSSSNIGSNYVYWYQQLPGTAPKLLIYSNNQRPSGVPDRFSGSKSGTSASLAISGLRSEDEADYYCAAWDDSLSGP IGLV3-1 (aka DPL23) (SEQ ID NO: 6)
QSVLTQPPSVSVSPGQTASITCSGDKLGDKYACWYQQKPGQSPVLVIYQDSKRPSGIPERFSGSNSGNTATLTISGTQAMDEADYYCQAWDSSTA IGLV3-19 (SEQ ID NO: 27)
SSELTQDPAVSVALGQTVRITCQGDSLRSYYASWYQQKPGQAPVLVIYGKNNRPSGIPDRFSGSSSGNTASLTITGAQAEDEADYYCNSRDSSGNHL IGLV3-21 (SEQ ID NO: 9)
QSVLTQPPSVSVAPGQTARITCGGNNIGSKSVHWYQQKPGQAPVLVVYDDSDRPSGIPERFSGSNSGNTATLTISRVEAGDEADYYCQVWDSSSDHP IGLV6-57 (SEQ ID NO: 12)
NFMLTQPHSVSESPGKTVTISCTGSSGSIASNYVQWYQQRPGSAPTTVIYEDNQRPSGVPDRFSGSIDSSSNSASLTISGLKTEDEADYYCQSYDSSN IGHV3-23 (aka DP47) (SEQ ID NO: 3)
EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAK

Figure 7

IGLV3-1::IGHV3-23 scaffold with variable CDR3 regions (SEQ ID NO: 84)

ATG GGA GAC GGT CAG TCT GTG CTG ACT CAG CCA CCC
TCAGTGTCCGTGTCCCCAGGACAGACAGCCAGCATCACCTGCTCTGGAGAT
AAATTGGGGGATAAATATGCTTGCTGGTATCAGCAGAAGCCAGGCCAGTCC
CCTGTGCTGGTCATCTATCAAGATAGCAAGCGGCCCTCAGGGATCCCTGAG
CGATTCTCTGGCTCCAACTCTGGGAACACAGCCACTCTGACCATCAGCGGG
ACCCAGGCTATGGATGAGGCTGACTATTACTGTCAGGCGTGGGAC
NNTNNTNNTGGAGGTNNTNNTNNT
ACTGTGGTGTTCGGCACGGGCACCAAGCTCATCATTTCGTCT
*CAGACCGGTGGTTCTGGTGGTGGTGGTTCTGGCGGCGGCGGCTCCGGTGGT*
*GGTGGATCC*
GAAGTCCAACTGCTGGAGTCCGGCGGTGGCCTGGTGCAGCCAGGTGGCAGC
CTGCGCCTGAGCTGCGCCGCATCCGGTTTTACTTTCAGCAGCTACGCGATGT
CGTGGGTGCGCCAGGCACCGGGCAAGGGCCTGGAGTGGGTCAGCGCCATC
AGCGGTAGCGGCGGTTCTACGTATTATGCGGACAGCGTCAAGGGCCGTTTC
ACCATCAGCCGTGACAATTCCAAAAACACCCTGTACTTGCAGATGAACAGC
TTGCGTGCGGAAGATACGGCTGTTTACTACTGTGCGAAA
NNTNNTNNTGGANNTNNTNNT
GCCTTTGATATTTGGGGTCAAGGTACCATGGTTACCGTGAGC AGC

Translation (SEQ ID NO: 85):

MGDGQSVLTQPPSVSVSPGQTASITCSGDKLGDKYACWYQQKPGQSPVLVIYQDSKRPSG
IPERFSGSNSGNTATLTISGTQAMDEADYYCQAWD NNNGGNNN TVVFGTGTKVTVSS *QTGGSGGGG*
*SGGGGSGGGGS* EVQLLESGGGLVQPGGSLRLSCAASGFTFSSYAMSWVRQAPGKGLEWVS
AISGSGGSTYYADSVKGRFTISRDNSKNTLYLQMNSLRAEDTAVYYCAK NNNGNNN
AFDIWGQGTMVTVSS

Figure 8

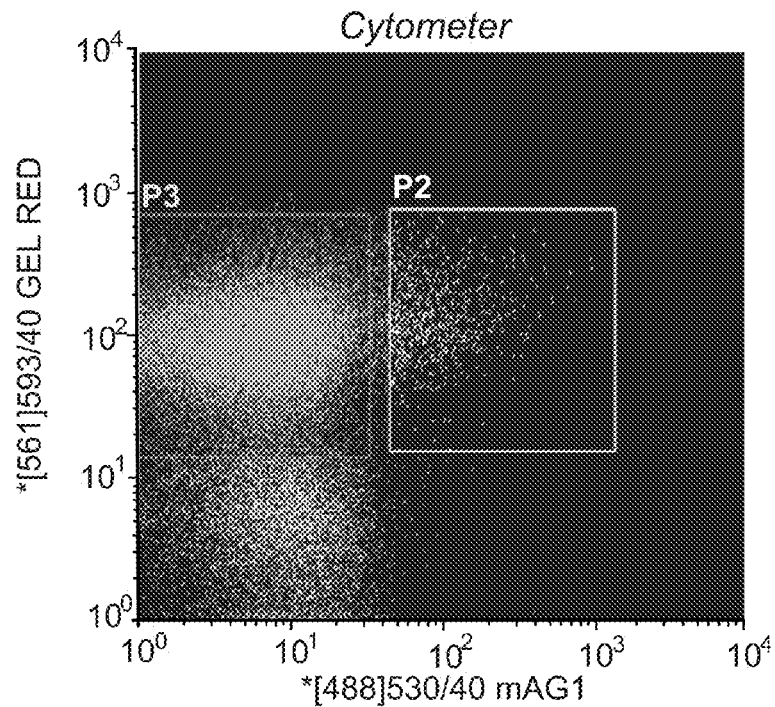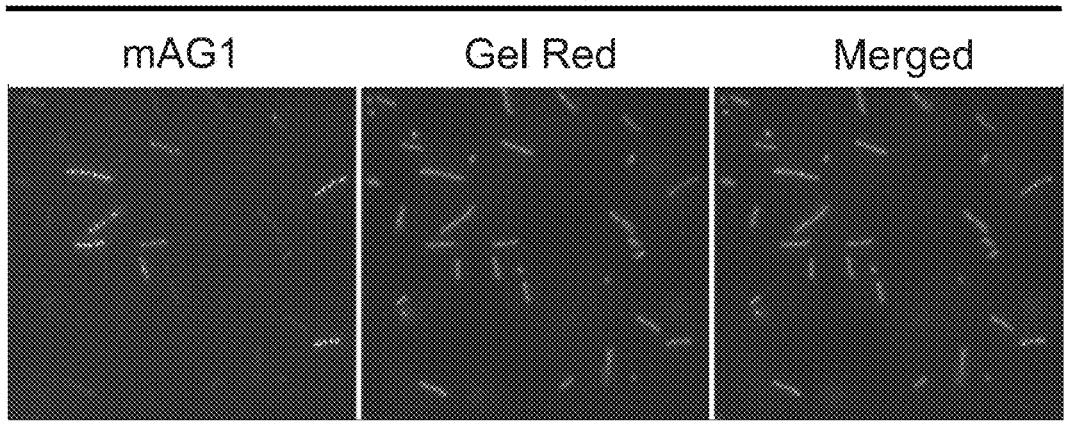
Figure 14

SOLUBLE POLYPEPTIDES

REFERENCE TO SEQUENCE LISTING

The present application is filed with a Sequence Listing in Electronic format. The Sequence Listing is provided as a file entitled 392190003001SequenceListing.txt, created Feb. 14, 2014, which is approximately 62 kb in size. The information in the electronic format of the sequence listing is incorporated herein by reference in its entirety.

FIELD OF THE INVENTION

The present invention relates generally to polypeptides, such as antibody molecules, that demonstrate high stability and solubility. In particular, the present invention relates to polypeptides comprising paired $V_L$ and $V_H$ domains that demonstrate soluble expression and folding in a reducing or intracellular environment. The present invention also relates to polynucleotides encoding such polypeptides, to libraries of such polypeptides or polynucleotides, and to methods of using such polypeptides in research, diagnostic and therapeutic applications. For example, the polypeptides can be used in screening methods to identify a polypeptide that binds to a particular target molecule.

BACKGROUND OF THE INVENTION

The vertebrate antibody repertoire was formed by the duplication and diversification of ancestral genes of a heterodimer of two immunoglobulin (Ig) folds. The diversity generated by the immune system relies not only on the germline gene families of Ig genes, but from the recombination of subdomain exons in vivo during B- and T-cell development to form numerous unique lineages with additional diversity at the exon boundaries that occur at surface-exposed loops of the Ig protein. This process of recombination is called V(D)J recombination, so called after the two variable light ($V_L$) and three variable heavy ($V_H$) exons that recombine to form the N-terminal antigen binding domains of the light chain and heavy chain of the antibody, respectively. However, as the duplicated genes diverged from their ancestral pair, the cumulated effect of mutations has resulted in a less-than-perfect interfacial fit between heterodimer units of the variable domains. Selection pressure is not applied to any one gene, but to the family as a whole. Thus, maximum diversity, which is a good thing for the immune system, can result in less-than-ideal folding stabilities for individual family members. Furthermore, the binding domains themselves may have different folding stabilities. The requirement to form a functional heterodimer from numerous diverged subunits is compensated for by the presence of conserved disulphide bonds between the Beta-sheets of the domains. However, the interface may still not be a stable fit, requiring a folding checkpoint in the ER.

As a result of the 'consensus' approach to a protein fit applied by the antibody variable domains, some pairings have a low folding stability and propensity for either poor expression in bacterial/mammalian hosts, and a propensity to aggregate. Furthermore, in almost all cases, there is a total requirement for the inter-sheet disulphide bonds to be formed within the $V_L$ and $V_H$ domains. This necessitates that for expression of antibody libraries in a bacterial host such as E. coli the antibody is expressed in the periplasm of the cell, an oxidizing space that has disulphide chaperones, and often as a fusion between the $V_L$ and $V_H$ domains (single chain antibody; scFv). However, export to the periplasm requires the excretion through the inner membrane, which is saturated at the levels desired for high expression of the antibody, resulting in far lower yields than cytoplasmic expression.

In addition to the advantage of cheaper production of scFv antibodies in the E. coli cytoplasm, an antibody scaffold that is competent to fold in a reducing environment would also be able to be used as an affinity reagent in the mammalian cytoplasm. This would enable the extension of the uses of antibodies as scientific reagents in the cytoplasm or nucleus for imaging or blocking protein function, and similarly in therapeutics and diagnostics.

As almost all mammalian antibodies are insoluble in the cytoplasm, groups have searched for the rare combinations of genes that fold to form a stable heterodimer to use as a scaffold for building further diversity. The approach taken to find cytoplasmically soluble antibodies is either the happenstance observation that an antibody clone is stably expressed in the cytoplasm (Tavladoraki et al., 1999; Vaccaro et al., 2006) which may form the basis for an intracellular antibody ("intrabody") scaffold, or, alternatively, an evolutionary approach may be taken to evolve a scFv gene towards stability, either in vivo (Martineau et al., 1998; Visintin et al., 1999; Auf der Maur et al., 2002; Fisher and DeLisa, 2009) or in vitro (Contreras-Martinez and Delisa, 2007; Jermutus L., et al. 2001). Furthermore, single domain antibodies, where only a single, unpaired, variable domain binds to the target antigen, have proven to be soluble and stable in the cytoplasm. Two camelid single domain antibodies that are folded and soluble when expressed in the cytoplasm have been described (Kirchhofer Al., et al, 2010; Saerens et al., 2005).

Another strategy for producing intracellular antibodies in the bacterial cytosol is the use of E. coli mutants that have mutations that change the redox state of proteins in the cytoplasm from reducing to oxidizing. This produces scFvs that are folded and partially and/or fully oxidized in the E. coli cytoplasm (He et al, 1995; Jurado P., et al., 2002).

Two groups that used the yeast-two-hybrid (Y2H) system as an in vivo screen for scFv binding to antigen from scFv libraries compiled sequences for their soluble clones. The first group (Tse et al., 2002) found that the VH3 Glade was paired with clades VLκ 1 and 4. By aligning multiple soluble scFvs they compiled a consensus for soluble $V_L$ and $V_H$ genes that almost exactly matched the family consensus compiled for the Morphosys HuCAL™ library for families VH3 and VLκ1 (Knappik et al., 2000). The second group using Y2H reported in WO 03/097697 that their soluble scFvs were either sequences most closely related to members of the VH3, VH1a or VH1b clades combined with sequences most closely related to members of the VLκ1 or VLλ1 or VLλ3 clades. However, their optimal configuration was VLλ3 paired with VH1b. Crucial to note, however, is that none of the sequences reported were exact matches to the translation of the germline sequence of the nearest homologous immunoglobulin gene, with multiple mutations throughout the sequence. This was presumably due to the use by both groups of pre-screened phage libraries to enrich for antigen binding clones before the limiting step of yeast transformation. However, this implies that one, or more, of the mutations in each gene may be conferring a stabilizing effect on scFv folding in the cytoplasm.

To date, there have been no published reports of an intracellular antibody that has an exact identity to the human germline amino acid sequence of the corresponding $V_L$ and $V_H$ genes. Such an antibody would be an advantageous scaffold for building diversification because it would allow a high yield from cytoplasmic expression, would provide higher stability in oxidized form, would provide greater structural stability ensuring greater tolerance of loop diversification, and would comprise a completely native sequence resulting in lowered patient rejection from production of a full antibody.

We report here the application of a protein display method previously described in WO 2011/075761 to the screening of a human scFv library and the isolation of soluble scFv genes that have identical framework regions to the human germline sequence. Furthermore, we demonstrate remarkable thermostability and tolerance of CDR3 grafting onto the scFv scaffold.

SUMMARY OF THE INVENTION

In one aspect, the invention provides a polypeptide library comprising a plurality of different polypeptides, which comprise:

i) an antibody heavy chain variable region ($V_H$) comprising a scaffold region which is at least 90% identical to the scaffold region of IGHV3-23 as set out in SEQ ID NO: 3; and ii) an antibody light chain variable region ($V_L$) comprising a scaffold region which is at least 90% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV1-51 (as set out in SEQ ID NO: 15), IGLV3-1 (as set out in SEQ ID NO: 6), IGLV3-19 (as set out in SEQ ID NO: 27), IGLV3-21 (as set out in SEQ ID NO: 9), IGLV6-57 (as set out in SEQ ID NO: 12);

wherein the $V_H$ and the $V_L$ are capable of forming an antigen-binding site; and wherein at least two of the polypeptides differ from one another in the sequence of amino acids present in one or more complementarity determining regions (CDRs) in the $V_H$ and/or $V_L$ variable regions.

Preferably, the sequence of amino acids in one or more of the CDRs of the $V_H$ and/or $V_L$ variable domains is random or semi-random or is derived from a human antibody.

In another aspect, the invention provides a method of constructing a polypeptide library, the method comprising preparing a plurality of different polypeptides, which comprise:

i) an antibody heavy chain variable region ($V_H$) comprising a scaffold region which is at least 90% identical to the scaffold region of IGHV3-23 as set out in SEQ ID NO: 3; and ii) an antibody light chain variable region ($V_L$) comprising a scaffold region which is at least 90% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV1-51 (as set out in SEQ ID NO: 15), IGLV3-1 (as set out in SEQ ID NO: 6), IGLV3-19 (as set out in SEQ ID NO: 27), IGLV3-21 (as set out in SEQ ID NO: 9), IGLV6-57 (as set out in SEQ ID NO: 12); wherein the $V_H$ and the $V_L$ are capable of forming an antigen-binding site; and wherein at least two of the polypeptides differ from one another in the sequence of amino acids present in one or more CDRs in the $V_H$ and/or $V_L$ variable regions.

In another aspect, the invention provides a polynucleotide library comprising a plurality of different polynucleotides, wherein each polynucleotide encodes a polypeptide comprising:

i) an antibody heavy chain variable region ($V_H$) comprising a scaffold region which is at least 90% identical to the scaffold region of IGHV3-23 as set out in SEQ ID NO: 3; and ii) an antibody light chain variable region ($V_L$) comprising a scaffold region which is at least 90% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV1-51 (as set out in SEQ ID NO: 15), IGLV3-1 (as set out in SEQ ID NO: 6), IGLV3-19 (as set out in SEQ ID NO: 27), IGLV3-21 (as set out in SEQ ID NO: 9), IGLV6-57 (as set out in SEQ ID NO: 12);

wherein the $V_H$ and the $V_L$ are capable of forming an antigen-binding site; and wherein at least two of the polynucleotides differ from one another by encoding polypeptides comprising one or more different CDRs in the $V_H$ and/or $V_L$ variable regions.

Preferably, the polynucleotides encode a sequence of amino acids in one or more of the CDRs of the $V_H$ and/or $V_L$ variable domains that is random or semi-random or is derived from a human antibody.

In another aspect, the invention provides a method of constructing a polynucleotide library, the method comprising preparing a plurality of different polynucleotides encoding a polypeptide, which comprises:

i) an antibody heavy chain variable region ($V_H$) comprising a scaffold region which is at least 90% identical to the scaffold region of IGHV3-23 as set out in SEQ ID NO: 3; and ii) an antibody light chain variable region ($V_L$) comprising a scaffold region which is at least 90% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV1-51 (as set out in SEQ ID NO: 15), IGLV3-1 (as set out in SEQ ID NO: 6), IGLV3-19 (as set out in SEQ ID NO: 27), IGLV3-21 (as set out in SEQ ID NO: 9), IGLV6-57 (as set out in SEQ ID NO: 12);

wherein the $V_H$ and the $V_L$ are capable of forming an antigen-binding site; and wherein at least two of the polynucleotides differ from one another by encoding polypeptides comprising one or more different CDRs in the $V_H$ and/or $V_L$ variable regions.

In another aspect, the invention provides an isolated and/or recombinant polypeptide comprising:

i) an antibody heavy chain variable region ($V_H$) comprising a scaffold region which is at least 90% identical to the scaffold region of IGHV3-23 as set out in SEQ ID NO: 3; and ii) an antibody light chain variable region ($V_L$) comprising a scaffold region which is at least 90% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV1-51 (as set out in SEQ ID NO: 15), IGLV3-1 (as set out in SEQ ID NO: 6), IGLV3-19 (as set out in SEQ ID NO: 27), IGLV3-21 (as set out in SEQ ID NO: 9), IGLV6-57 (as set out in SEQ ID NO: 12);

wherein the $V_H$ and the $V_L$ are capable of forming an antigen-binding site.

The $V_L$ preferably comprises a scaffold region which is at least 90% identical to the scaffold region of IGLV3-1 as set out in SEQ ID NO 6.

Preferably, the polypeptide is a variable fragment (Fv), such as a Fab fragment, a Fab' fragment, a F(ab') fragment, a scFv, a diabody, a triabody, a tetrabody or higher order polypeptide complex. More preferably, the polypeptide is a scFv and the $V_H$ and the $V_L$ are linked together via a peptide linker.

Preferably, the scaffold region of the $V_H$ and/or $V_L$ variable regions in the polypeptide of the invention is at least 95%, 96%, 97%, 98% or 99% identical to the scaffold region of any of the given sequences.

The polypeptide of the invention is preferably soluble under reducing conditions. In addition, the polypeptide of the invention is preferably soluble and capable of stably forming an antigen-binding site when produced under reducing conditions.

In another preferred embodiment, the polypeptide of the invention is conjugated to a compound. The compound may be selected from the group consisting of a radioisotope, a detectable label, a therapeutic compound, a colloid, a toxin, a nucleic acid, a peptide, a protein, a compound that increases the half life of the polypeptide in a subject, and mixtures thereof.

In another aspect, the invention provides an isolated and/or exogenous polynucleotide encoding the polypeptide of the invention, or a heavy or light chain variable region thereof.

In another aspect, the invention provides a vector comprising the polynucleotide of the invention.

In another aspect, the invention provides a host cell comprising the polypeptide of the invention, the polynucleotide of the invention, or the vector of the invention.

In a further aspect, the invention provides a method of screening for a polypeptide that binds to a target molecule, the method comprising contacting a polypeptide of the invention with the target molecule, and determining whether the polypeptide binds to the target molecule. In such methods, it is preferred if a polynucleotide encoding the polypeptide is expressed in a host cell or in a cell-free expression system to produce the polypeptide. When expressing the polypeptide within a cell, this expression may take place in the cytoplasm and/or periplasm of a host cell, such as a bacterial cell, a yeast cell or a mammalian cell.

In a preferred embodiment, the host cell is a bacterial cell and the method comprises:

a) culturing a bacterial cell comprising a polynucleotide encoding the polypeptide of the invention such that the polypeptide is produced, b) permeabilising the bacterial cell, wherein the polynucleotide and the polypeptide is retained inside the permeabilised bacterial cell, c) contacting the permeabilised bacterial cell with the target molecule such that it diffuses into the permeabilised bacterial cell, and d) determining whether the polypeptide of the invention binds to the target molecule.

The screening methods of the invention can be performed using any of the polypeptides described herein. Preferably, the screening methods of the invention comprise screening a library of the invention. Thus, the screening methods may comprise expressing a polypeptide or polynucleotide library of the invention and identifying polypeptides within those libraries that bind to a target molecule. Preferably, such screening methods are performed under reducing conditions. For example, such methods can be performed in a host cell. In a preferred embodiment, such methods are performed in the cytoplasm of a host cell. Preferably, the host cell is a bacterial cell, such as a gram negative bacterial cell. In a preferred embodiment, the bacterial cell is an E. coli cell.

In a further aspect, the invention provides a host cell library comprising a plurality of host cells comprising a polypeptide of the invention, wherein at least one host cell comprises a polypeptide that differs from a polypeptide present in another host cell in the library in the sequence of amino acids present in one or more CDRs in the $V_H$ and/or $V_L$ variable domains. One or more host cells in the host cell library of the invention may comprise one or more polynucleotides encoding the polypeptide of the invention. For example, a host cell in the host cell library may contain one polynucleotide encoding the $V_H$ and another polynucleotide encoding the $V_L$.

In another aspect, the invention provides a composition comprising the polypeptide, the polynucleotide and/or the vector of the invention, and a pharmaceutically acceptable carrier.

In another aspect, the invention provides a kit comprising the polypeptide of the invention, the polynucleotide of the invention and/or the invention, and an agent capable of permeabilising a bacterial cell.

In a further aspect, the invention provides the use of the polypeptide of the invention in therapeutic or diagnostic applications.

As will be apparent, preferred features and characteristics of one aspect of the invention are applicable to any other aspects of the invention, mutatis mutandis.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE
ACCOMPANYING DRAWINGS

FIG. 1 shows the typical appearance of a well-expressed, soluble scFv clone (1A, and inset), along with a well-expressed, but insoluble scFv clone (1B, and inset).

FIGS. 2, 2A, and 2B (hereinafter, "FIG. 2") show a multiple alignment of selected soluble clones that have high similarity, or total identity, to the VL genes IGLV3-1, IGLV3-21 and IGLV6-57.

FIG. 3 demonstrates the behaviour of two clones, one IGLV3-1 and one IGLV3-21, with expression at increasing temperatures.

FIG. 4 demonstrates the solubility of an IGLV3-1 clone when expressed in the E. coli cytosol at 25° C. The scFv::127::FLAG fusion protein is entirely in the soluble (S) fraction.

FIG. 5 demonstrates the thermostability behaviour of the original clone (#8.93) with replacement of the λ J region for J1 or J2.

FIG. 6A demonstrates the solubility and high expression of 4 independent clones with the IGLV3-1 CDR3 diversified.

FIG. 6B demonstrates a sample of the entire population of clones with the IGHV3-23 CDR3 diversified.

FIG. 7 illustrates exemplary CDRs (in bold and/or underlined) in preferred variable regions described herein.

FIG. 8 illustrates an example of a polynucleotide sequence encoding an IGLV3-1::IGHV3-23 scaffold with variable CDR3 regions, and the corresponding, translated amino acid sequence. CDRs are underlined and in bold type. A peptide linker sequence is italicized.

FIG. 9 shows the SNAP ligand-labeled IGLV3-1::IGHV3-23 scFv library, demonstrating the high frequency of soluble library members.

FIG. 10 shows the isolation of mAG-binding scFvs from a RED screen. Clone 34 was positive for mAG binding. Clone 25 was negative.

Figure 13:
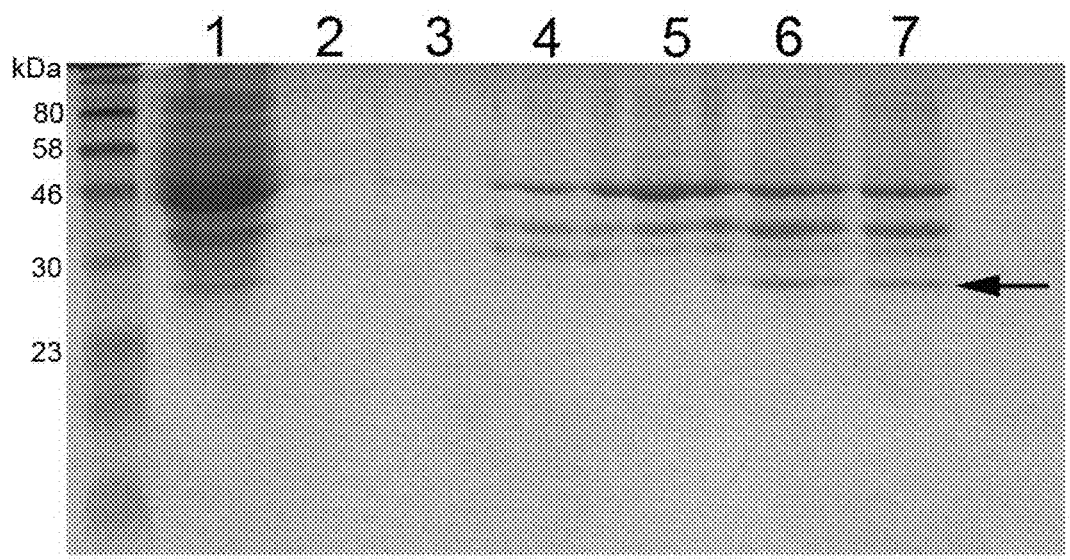

FIG. 13 demonstrates the specificity of the α-mAG scFv interaction for mAG by a 'pull-down' of unpurified mAG from *E. coli* lysate. α-mAG scFv His6 FLAG was bound to IMAC Ni-sepharose resin with the addition of mAG in total *E. coli* cell lysate (lanes 6 and 7) resulting in the binding of a protein of the expected size of mAG (~26 kD).

FIG. 14 shows a screen-grab (Top) from the FACS stage of the 'doped' mAG library screen using the encapsulated lysis-defective bacteriophage displaying the gpD::α-mAG scFv fusion protein. The mAG-positive cells containing encapsulated phage are in the right gate. The bacteriophage recovered from the FACS screen were induced for bacteriophage replication and gpD::α-mAG expression and labeled with mAG using the RED method (Bottom).

KEY TO THE SEQUENCE LISTING

SEQ ID NO: 1—polynucleotide sequence encoding IGHV3-23 (NCBI Ref. NT_026437.12).
SEQ ID NO: 2—polynucleotide sequence encoding IGHV3-23, excluding introns.
SEQ ID NO: 3—amino acid sequence of IGHV3-23
SEQ ID NO: 4—polynucleotide sequence encoding IGLV3-1 (NCBI Ref. NT_011520.12).
SEQ ID NO: 5—polynucleotide sequence encoding IGLV3-1, excluding introns.
SEQ ID NO: 6—amino acid sequence of IGLV3-1
SEQ ID NO: 7—polynucleotide sequence encoding IGLV3-21 (NCBI Ref. NT_011520.12)
SEQ ID NO: 8—polynucleotide sequence encoding IGLV3-21, excluding introns.
SEQ ID NO: 9—amino acid sequence of IGLV3-21
SEQ ID NO: 10—polynucleotide sequence encoding IGLV6-57 (NCBI Reference: NW_001838745.1)
SEQ ID NO: 11—polynucleotide sequence encoding IGLV6-57, excluding introns.
SEQ ID NO: 12—amino acid sequence of IGLV6-57
SEQ ID NO: 13—polynucleotide sequence encoding IGLV1-51 (NCBI Reference Sequence: NT_011520.12)
SEQ ID NO: 14—polynucleotide sequence encoding IGLV1-51, excluding introns.
SEQ ID NO: 15—amino acid sequence of IGLV1-51
SEQ ID NO: 16—polynucleotide sequence encoding IGLV1-40 (NCBI Reference Sequence: NT_011520.12)
SEQ ID NO: 17—polynucleotide sequence encoding IGLV1-40, excluding introns.
SEQ ID NO: 18—amino acid sequence of IGLV1-40
SEQ ID NO: 19—polynucleotide sequence encoding IGLV1-44 (NCBI Reference Sequence: NT_011520.12)
SEQ ID NO: 20—polynucleotide sequence encoding IGLV1-44, excluding introns.
SEQ ID NO: 21—amino acid sequence of IGLV1-44
SEQ ID NO: 22—polynucleotide sequence encoding IGLV1-47 (NCBI Reference Sequence: NT_011520.12)
SEQ ID NO: 23—polynucleotide sequence encoding IGLV1-47, excluding introns.
SEQ ID NO: 24—amino acid sequence of IGLV1-47
SEQ ID NO: 25—polynucleotide sequence encoding IGLV3-19 (NCBI Reference Sequence: NT_011520.12)
SEQ ID NO: 26—polynucleotide sequence encoding IGLV3-19, excluding introns.
SEQ ID NO: 27—amino acid sequence of IGLV3-19
SEQ ID NO: 28—Preferred peptide linker
SEQ ID NO: 29—CDR variant sequence
SEQ ID NO: 30—Alternative CDR variant sequence
SEQ ID NO: 31—Primer HVK1 F1
SEQ ID NO: 32—Primer HVK1 F2
SEQ ID NO: 33—Primer HVK2 F
SEQ ID NO: 34—Primer HVK3 F
SEQ ID NO: 35—Primer HVK4 F
SEQ ID NO: 36—Primer HVK5 F
SEQ ID NO: 37—Primer HVK6 F
SEQ ID NO: 38—Primer HVKCL R
SEQ ID NO: 39—Primer HVL1 F1
SEQ ID NO: 40—Primer HVL1 F2
SEQ ID NO: 41—Primer HVL2 F
SEQ ID NO: 42—Primer HVL3 F1
SEQ ID NO: 43—Primer HVL3 F2
SEQ ID NO: 44—Primer HVL4 F1
SEQ ID NO: 45—Primer HVL4 F2
SEQ ID NO: 46—Primer HVL5 F
SEQ ID NO: 47—Primer HVL6 F
SEQ ID NO: 48—Primer HVL7/8 F
SEQ ID NO: 49—Primer HVL9/10 F
SEQ ID NO: 50—Primer 01115 HVLCL R
SEQ ID NO: 51—Primer 01116 HVLCL R2
SEQ ID NO: 52—Primer HVK1 2F1
SEQ ID NO: 53—Primer HVK1 2F2
SEQ ID NO: 54—Primer HVK2 2F
SEQ ID NO: 55—Primer HVK3 2F
SEQ ID NO: 56—Primer HVK4 2F
SEQ ID NO: 57—Primer HVK5 2F
SEQ ID NO: 58—Primer HVK6 2F
SEQ ID NO: 59—Primer HVKCL 2R
SEQ ID NO: 60—Primer HVL1 2F1
SEQ ID NO: 61—Primer HVL1 2F2
SEQ ID NO: 62—Primer HVL2 2F
SEQ ID NO: 63—Primer HVL3 2F1
SEQ ID NO: 64—Primer HVL3 2F2
SEQ ID NO: 65—Primer HVL4 2F1
SEQ ID NO: 66—Primer HVL4 2F2
SEQ ID NO: 67—Primer HVL5 2F
SEQ ID NO: 68—Primer HVL6 2F
SEQ ID NO: 69—Primer HVL7/8 2F
SEQ ID NO: 70—Primer HVL9/10 2F
SEQ ID NO: 71—Primer HVLCL 2R
SEQ ID NO: 72—Lamda J region J1
SEQ ID NO: 73—Lamda J region J2
SEQ ID NO: 74—Lamda J region J3
SEQ ID NO: 75—Lamda J region J4
SEQ ID NO: 76—Lamda J region J5
SEQ ID NO: 77—Lamda J region J6
SEQ ID NO: 78—Lamda J region J7
SEQ ID NO: 79—Hybrid J region sequence
SEQ ID NO: 80—PCR primer
SEQ ID NO: 81—Translated sequence
SEQ ID NO: 82—PCR primer
SEQ ID NO: 83—Translated sequence SEQ ID NO: 84—Polynucleotide sequence encoding an IGLV3-1::IGHV3-23 scaffold with variable CDR3 regions
SEQ ID NO: 85—Amino acid sequence encoded by the polynucleotide of SEQ ID NO: 84
SEQ ID NO: 86—Template CDR3 sequence
SEQ ID NO: 87—Alternative template CDR3 sequence
SEQ ID NO: 88—Framework sequence of IGLV3-1 and the J region of IGHV3-23
SEQ ID NO: 89—Intervening sequence
SEQ ID NO: 90—Degenerate primer 1
SEQ ID NO: 91—Degenerate primer 2
SEQ ID NO: 92—CDR3 loop L1
SEQ ID NO: 93—CDR3 loop H1
SEQ ID NO: 94—CDR3 loop L2
SEQ ID NO: 95—CDR3 loop H2
SEQ ID NO: 96—CDR3 loop L3
SEQ ID NO: 97—CDR3 loop H3
SEQ ID NO: 98—CDR3 loop L4
SEQ ID NO: 99—CDR3 loop H4
SEQ ID NO: 100—CDR3 loop L5
SEQ ID NO: 101—CDR3 loop H5
SEQ ID NO: 102—CDR3 loop L6
SEQ ID NO: 103—CDR3 loop H6
SEQ ID NO: 104—CDR3 loop L8
SEQ ID NO: 105—CDR3 loop H8
SEQ ID NO: 106—CDR3 loop L9
SEQ ID NO: 107—CDR3 loop H9
SEQ ID NO: 108—CDR3 loop L10
SEQ ID NO: 109—CDR3 loop H10
SEQ ID NO: 110-mAG-BioHis6 protein
SEQ ID NO: 111-Anti-mAG-BioHis6 scFv sequence
SEQ ID NO: 112—gpD::α-mAG scFv fusion construct polynucleotide sequence
SEQ ID NO: 113—gpD::α-mAG scFv fusion protein sequence
SEQ ID NO: 114—Wildtype human IGLV 3-1
SEQ ID NO: 115—Soluble clone 8.93
SEQ ID NO: 116—Soluble clone 8.184
SEQ ID NO: 117—Soluble clone 8.174
SEQ ID NO: 118—Soluble human IGLV 3-21 clone 8.186
SEQ ID NO: 119—Soluble human IGLV 3-21 clone 8.39
SEQ ID NO: 120—Wildtype human IGLV 3-21
SEQ ID NO: 121—Soluble human IGLV 3-21 clone 9.19
SEQ ID NO: 122—Wildtype human IGLV 6-57
SEQ ID NO: 123—Soluble clone 16.26
SEQ ID NO: 124—Soluble clone 16.1
SEQ ID NO: 125—Soluble clone 16.121

DETAILED DESCRIPTION

General Techniques and Definitions

Unless specifically defined otherwise, all technical and scientific terms used herein shall be taken to have the same meaning as commonly understood by one of ordinary skill in the art (e.g., in protein chemistry, biochemistry, cell culture, molecular genetics, microbiolgy, and immunology).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, 3$^{rd}$ edn, Cold Spring Harbour Laboratory Press (2001), R. Scopes, Protein Purification—Principals and Practice, 3$^{rd}$ edn, Springer (1994), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The terms "polypeptide", "protein" and "peptide" are generally used interchangeably herein. As used herein, the term "exogenous polypeptide" refers to a polypeptide encoded by an exogenous polynucleotide. The term "exogenous polynucleotide" as used herein refers to a polynucleotide which is foreign to the cell into which it has been introduced, or that the sequence is homologous to a sequence in the cell into which it is introduced but in a position within the host cell nucleic acid in which the polynucleotide is not normally found.

The terms "antibody", "antibodies", "antibody molecule" and "antibody molecules" as used herein include polyclonal antibodies, monoclonal antibodies, bispecific antibodies, diabodies, triabodies, multibodies, heteroconjugate antibodies, chimeric antibodies including intact molecules as well as fragments thereof, such as Fab, F(ab')2, Fv and scFv and other antibody-like molecules. The skilled artisan will be aware that an antibody is generally considered to be a protein that comprises a variable region made up of a plurality of polypeptide chains, e.g., a light chain variable region ($V_L$) and a heavy chain variable region ($V_H$). An antibody may also comprise constant domains, which can be arranged into a constant region or constant fragment or fragment crystallisable (Fc). Antibodies can bind specifically to one or a few closely related antigens. Full-length antibodies generally comprise two heavy chains (~50-70 kD) covalently linked and two light chains (~23 kD each). A light chain generally comprises a variable region and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains may be held together by inter-chain disulfide bonds and/or by non-covalent interactions. The number of inter-chain disulfide bonds (if present) can vary among different types of antibodies. Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is often aligned with and disulfide bonded to the first constant domain of the heavy chain ($C_H$ which is ~330-440 amino acids in length). The light chain variable region is often aligned with the variable region of the heavy chain. The antibody heavy chain can comprise 2 or more additional $C_H$ domains (such as, $C_H2$, $C_H3$ and the like) and can comprise a hinge region that can be identified between the $C_H1$ and Cm constant domains. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. Preferably, the antibody is a murine (mouse or rat) antibody or a primate (preferably human)

antibody. The term "antibody" also encompasses humanized antibodies, primatized antibodies, human antibodies and chimeric antibodies.

As used herein, the term "variable region" refers to the portions of the light and heavy chains of an antibody as defined herein that includes amino acid sequences of CDRs; i.e., CDR1, CDR2, and CDR3, and framework regions (FRs). $V_H$ refers to the variable region of the heavy chain. $V_L$ refers to the variable region of the light chain.

As used herein, the term "scaffold region" refers to all the variable region residues other than the CDR residues.

As used herein, the term "framework region" (FR) will be understood to mean a contiguous sequence of variable region residues other than the CDR residues. Thus, all of the FRs together make up the "scaffold region". Each variable region of a naturally-occurring antibody typically has four FRs, identified as FR1, FR2, FR3 and FR4. If the CDRs are defined according to Kabat, exemplary light chain FR (LCFR) residues are positioned at about residues 1-23 (LCFR1), 35-49 (LCFR2), 57-88 (LCFR3), and 98-107 (LCFR4). Note that λLCFR1 does not comprise residue 10, which is included in κLCFR1. Exemplary heavy chain FR(HCFR) residues are positioned at about residues 1-30 (HCFR1), 36-49 (HCFR2), 66-94 (HCFR3), and 103-113 (HCFR4).

As used herein, the term "complementarity determining regions" (CDRs; i.e., CDR1, CDR2, and CDR3 or hypervariable region) refers to the amino acid residues of an immunoglobulin variable region the presence of which are necessary for antigen binding. Each variable region typically has three CDR regions identified as CDR1, CDR2 and CDR3. Each CDR may comprise amino acid residues from a "complementarity determining region" as defined by Kabat (1987 and/or 1991). For example, in a heavy chain variable region CDRH1 is between residues 31-35, CDRH2 is between residues 50-65 and CDRH3 is between residues 95-102. In a light chain CDRL1 is between residues 24-34, CDRL2 is between residues 50-56 and CDRL3 is between residues 89-97. These CDRs can also comprise numerous insertions, e.g., as described in Kabat (1987 and/or 1991).

The term "constant region" (CR or fragment crystallizable or Fc) as used herein, refers to a portion of an antibody comprising at least one constant domain and which is generally (though not necessarily) glycosylated and which binds to one or more receptors and/or components of the complement cascade (e.g., confers effector functions). The heavy chain constant region can be selected from any of the five isotypes: α, δ, ε, γ, or μ. Furthermore, heavy chains of various subclasses (such as the IgG subclasses of heavy chains) are responsible for different effector functions and thus, by choosing the desired heavy chain constant region, proteins with desired effector function can be produced. Preferred heavy chain constant regions are gamma 1 (IgG1), gamma 2 (IgG2) and gamma 3 (IgG3).

A "constant domain" is a domain in an antibody the sequence of which is highly similar in antibodies of the same type, e.g., IgG or IgM or IgE. A constant region of an antibody generally comprises a plurality of constant domains, e.g., the constant region of γ, α and δ heavy chains comprise three constant domains and the Fc of γ, α and δ heavy chains comprise two constant domains. A constant region of μ and ε heavy chains comprises four constant domains and the Fc region comprises two constant domains.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore an Fv of the invention (as well as any polypeptide of the invention) may have multiple antigen binding sites which may or may not bind the same antigen. The term "Fv" shall be understood to encompass fragments directly derived from an antibody as well as proteins corresponding to such a fragment produced using recombinant means. In preferred embodiments, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain. A "Fab fragment" consists of a monovalent antigen-binding fragment of an antibody, and can be produced, for example, by digestion of a whole antibody with the enzyme papain, to yield a fragment consisting of an intact light chain and a portion of a heavy chain or can be produced using recombinant means. A "Fab' fragment" of an antibody can be obtained, for example, by treating a whole immunoglobulin with pepsin, followed by reduction, to yield a molecule consisting of an intact light chain and a portion of a heavy chain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "$Fab_2$" fragment is a recombinant fragment comprising two Fab fragments linked using, for example a leucine zipper or a $C_H3$ domain.

A "single chain Fv" or "scFv" is a recombinant molecule containing the variable region fragment (Fv) of an immunoglobulin in which the variable region of the light chain and the variable region of the heavy chain are covalently linked by a suitable, flexible polypeptide linker. A detailed discussion of exemplary Fv containing polypeptides falling within the scope of this term is provided herein below.

As used herein, the term "antigen binding site" shall be taken to mean a structure formed by a polypeptide that is capable of specifically binding to an antigen. The antigen binding site need not be a series of contiguous amino acids, or even amino acids in a single polypeptide chain. For example, in a Fv produced from two different polypeptide chains the antigen binding site is made up of a series of regions of a $V_L$ and a $V_H$ that interact with the antigen and that are generally, however not always in the one or more of the CDRs in each variable region.

Any amino acid positions assigned to CDRs and FRs herein are defined according to Kabat (1987 and 1991). The skilled artisan will be readily able to use other numbering systems in the performance of this invention, e.g., the hypervariable loop numbering system of Chothia and Lesk (1987 and/or 1989) and/or Al-Lazikani et al (1997).

The skilled artisan will be aware that a "disulphide bond" is a covalent bond formed by coupling of thiol groups. The bond is also called an SS-bond or disulfide bridge. In polypeptides, a disulphide bond generally occurs between the thiol groups of two cysteine residues.

The skilled artisan will also be aware that the term "non-reducing conditions" includes conditions sufficient for oxidation of sulfhydryl (—SH) groups in a protein, e.g., permissive for disulphide bond formation. Accordingly, the term "reducing conditions" includes conditions which are not sufficient for oxidation of sulfhydryl (—SH) groups in a protein, e.g., not permissive for disulphide bond formation.

As used herein, the term "antigen" shall be understood to mean any composition of matter against which an antibody response can be raised. Exemplary antigens include proteins, peptides, polypeptides, carbohydrates, phosphate groups, phosphor-peptides or polypeptides, glyscosylated peptides or peptides, etc.

The description and definitions of variable regions and parts thereof, immunoglobulins, antibodies and fragments thereof herein may be further clarified by the discussion in Kabat (1987 and/or 1991), Bork et al (1994) and/or Chothia and Lesk (1987 and 1989) or Al-Lazikani et al (1997).

As used herein, the terms "conjugate", "conjugated" or variations thereof are used broadly to refer to any form to covalent or non-covalent association between a compound useful in the methods disclosed herein and another agent.

The term "and/or", e.g., "X and/or Y" shall be understood to mean either "X and Y" or "X or Y" and shall be taken to provide explicit support for both meanings or for either meaning.

The term "about" as used herein refers to a range of +/−5% of the specified value.

As will be understood from the following description, the present inventors have applied protein display methods to identify polypeptides, (for example, antibodies) that can be expressed in soluble form in the cellular cytoplasm and that demonstrate surprising levels of solubility, thermostability, and tolerance to CDR diversification. The inventors have further demonstrated that the human immunoglobulin repertoire has the potential for cytoplasmic solubility and stability using only germline sequences in the framework regions of antibody variable domains.

Retained Encapsulated Display (RED):

The present inventors have identified polypeptides that can be expressed in soluble form in the cellular cytoplasm and that demonstrate surprising levels of solubility, thermostability, and tolerance to CDR diversification using the method of Retained Encapsulated Display (RED). RED is a protein display platform for gram-negative bacteria that is described in WO 2011/075761 (the content of which is incorporated by reference in its entirety). In RED the protein to be displayed is expressed in either the periplasm or cytoplasm of the cell. The cellular membranes are then permeabilised with detergent or organic solvents while the cell wall is left intact. The display protein is retained by the cell wall, either through fusion to proteins that increase its molecular size to above the porosity limit for the cell wall (e.g. fusion to tetramer monomers), or through fusion to protein domains that bind either DNA, the cell wall itself, or both. The phenotype-genotype linkage required for a display system is provided through the co-retention of the plasmid and genomic DNA within the cell wall of the permeabilised cell.

Polypeptides:

The human antibody repertoire contains both functional and pseudogene variable regions (summarized by Lefranc, 2000). These may be cloned as exons from either genomic DNA in non-immune lineages, or from mRNA sourced from immune cells that have undergone V(D)J recombination, in order to prepare a genetic construct which can be used to express the antibody. During such a process, the variable domains of the light and heavy chains may be cloned as either a monomeric scFv, or in arrangements that form bivalent or higher-order valencies. The constant regions may also be cloned downstream of the variable domains to create Fab or full-length antibodies.

In all forms, to attain the correct fold and maintain stability and solubility during the production of an antibody, the genetic constructs encoding the antibody must almost always be expressed under conditions such that intra-domain disulphide bonds may form between the β sheets (i.e., under non-reducing conditions). Thus, in mammalian cells, antibodies are inserted into the endoplasmic reticulum (ER) and Golgi for secretion or membrane insertion. If expressed in a bacterial host such as E. coli they must be directed to the periplasmic space where the disulphide bond chaperones DsbA, B and C reside. If an antibody is expressed in a non-oxidising environment, (such as in the cellular cytoplasm) the lack of stabilizing disulphide bonds results in misfolding and degradation or, if expressed at a high level in the E. coli cytoplasm, aggregation as a subcellular inclusion body.

The present inventors have identified polypeptides comprising antibody variable region scaffolds, which are capable of forming an antigen binding site even when the polypeptides are expressed in a non-oxidising (reducing) environment.

Accordingly, the invention provides an isolated and/or recombinant polypeptide comprising an antibody heavy chain variable region ($V_H$) of the $V_H3$ family of immunoglobulin variable domains linked via a peptide linker to an antibody light chain variable region ($V_L$) of the $V_L\lambda1$, 3 or 6 families of immunoglobulin variable domains, wherein the $V_H$ and the $V_L$ are capable of forming an antigen-binding site.

The polypeptide of the invention may be provided in the form of any of the known forms of antibodies or antibody fragments. Thus, the polypeptide of the invention may be: (i) an antibody; (ii) a single domain antibody; (iii) a single chain Fv (scFv); (iv) a diabody, a triabody or a tetrabody; (v) a fusion protein comprising any one of (ii)-(iv) and a Fc domain of an antibody or a domain thereof; (vi) a fusion protein comprising any one of (ii)-(iv) and a protein capable of binding to an immune effector cell, or any other known form of antibody.

Preferably, the polypeptide of the invention is a Fv. For example, the polypeptide of the invention is preferably a Fab fragment, a Fab' fragment, a F(ab') fragment, a scFv, a diabody, a triabody, a tetrabody or higher order polypeptide complex.

Most preferably, the polypeptide of the invention is a scFv. scFvs comprise $V_H$ and $V_L$ regions in a single polypeptide chain. Preferably, the polypeptide chain further comprises a polypeptide linker between the $V_H$ and $V_L$ which enables the scFv to form the desired structure for antigen binding (i.e., for the $V_H$ and $V_L$ of the single polypeptide chain to associate with one another to form an antigen binding site). This is distinct from a diabody or higher order multimer of the invention, in which variable regions from different polypeptide chains associate or bind to one another. The peptide linker may comprise 12 or more amino acid residues. For example, the peptide linker may comprise 12, 13, 14, 15, 16, 17, 18, 19, 20, 21, 22, 23, 24, 25, 26, 27, 28, 29, 30 amino acids or more. Preferably, the peptide linker comprises in excess of 12 amino acid residues, with $(Gly_4Ser)_3$ (i.e., GGGGSGGGGSGGGGS (SEQ ID NO: 28)) being one of the more favored linkers for a scFv. Other suitable polypeptide linkers are known in the art. The polypeptides of the invention preferably comprise a scaffold region of a $V_H$ of the $V_H3$ family of immunoglobulin variable and/or a scaffold region of a $V_L$ of the $V_L\lambda1$, 3 or 6 families of immunoglobulin variable domains. Thus, the polypeptides of the invention preferably comprise all of the amino acid residues of any of the variable regions disclosed herein, excluding CDR residues. The CDR residues can readily be identified by the person skilled in the art, with reference to the discussion in Kabat (1987 and/or 1991), Bork et al (1994) and/or Chothia and Lesk (1987 and 1989) or Al-Lazikani et al (1997). Thus, the polypeptides of the invention can comprise all of the FRs of any variable region disclosed herein. The polypeptides may further comprise one or more of the CDRs of the variable regions disclosed herein. The polypeptides may also comprise one or more CDRs which are not present in the variable regions disclosed herein. Thus, one or more CDRs from a different source can be inserted into the scaffold region of the variable regions disclosed herein. A further discussion of such possibilities is included herein, below.

In a preferred embodiment, scFvs of the invention comprise a scaffold region of a $V_H$ of the $V_H3$ family of immunoglobulin variable domains linked via a peptide linker to a $V_L$ of the $V_L\lambda1$, 3 or 6 families of immunoglobulin variable domains. In further preferred embodiments, the scFvs of the invention comprise a scaffold region of IGHV3-23 and a scaffold region of any one of IGLV1-40, IGLV1-44, IGLV1-47, IGLV1-51, IGLV3-1, IGLV3-19, IGLV3-21, and IGLV6-57. Most preferably, scFvs of the invention comprise a scaffold region of IGHV3-23 and a scaffold region of IGLV3-1.

The polypeptides of the invention may be defined in terms of their percentage identity to a reference sequence. This percentage identity may be calculated by any suitable method known in the art. Several algorithms for comparing aligned sequences are known, and can be used to determine the percentage identity of a polypeptide of the invention to a reference sequence. For example, amino acid and polynucleotide sequences can be compared manually or by using computer-based sequence comparison and identification tools that employ algorithms such as BLAST (Basic Local Alignment Search Tool; Altschul et al., 1993); see also www.ncbi.nlm.nih.gov/BLAST/), the Clustal method of alignment (Higgins and Sharp, 1989) and others, wherein appropriate parameters for each specific sequence comparison can be selected as would be understood by a person skilled in the art.

Preferably, the polypeptide of the invention is an isolated and/or recombinant polypeptide. The term "isolated" or "purified" as used herein is intended to mean a polypeptide that has generally been separated from the lipids, nucleic acids, other polypeptides and peptides, and other contaminating molecules with which it is associated in its native state. Preferably, the isolated polypeptide is at least 60% free, more preferably at least 75% free, and more preferably at least 90% free from other components with which it is naturally associated.

The term "recombinant" in the context of a polypeptide refers to the polypeptide when produced by a cell, or in a cell-free expression system, in an altered amount or at an altered rate compared to its native state. In one embodiment the cell is a cell that does not naturally produce the polypeptide. However, the cell may be a cell which comprises a non-endogenous gene that causes an altered, preferably increased, amount of the peptide to be produced. A recombinant polypeptide as described herein includes polypeptides which have not been separated from other components of the transgenic (recombinant) cell or cell-free expression system in which it is produced, and polypeptides produced in such cells or cell-free systems which are subsequently purified away from at least some other components.

Then polypeptide of the invention preferably comprises amino acid sequences which are derived from a murine (mouse or rat) antibody or a primate (preferably human) antibody. Thus, the variable regions and/or scaffold regions included in the polypeptides of the invention may be murine (mouse or rat) or primate (preferably, human) variable regions and/or scaffold regions.

Preferably, the polypeptides of the invention are soluble. Methods for determining the solubility of a polypeptide are well known in the art, e.g., as described by J. Sambrook et al., Molecular Cloning: A Laboratory Manual, $3^{rd}$ edn, Cold Spring Harbour Laboratory Press (2001). The polypeptides may be determined to be soluble if, for example, they cannot be separated from a lysed and/or permeabilised cell fraction by physical separation (e.g. by centrifugation). In addition, the polypeptides of the invention may be determined to be soluble if they do not form inclusion bodies in cellular cytoplasm. Thus, the polypeptides may be considered to be soluble if, when they are expressed in a host cell, they are retained in a soluble fraction produced after lysis of the host cell by any suitable mechanical, detergent and/or enzymatic methods. Suitable mechanical methods include, for example, the use of sonication. Suitable detergent methods include, for example, the use of n-Octyl-β-D-Thioglucoside (8TGP). Suitable enzymatic methods include, for example, the use of lysozyme. Preferably, the polypeptides of the invention can be retained in a soluble fraction of a cell lysate at a level of at least 25%, such as at least 50%, at least 75%, at least 90%, at least 95%, or at least 95%.

The polypeptides of the invention are preferably capable of stably forming an antigen binding site. Thus, the polypeptides are preferably capable of binding to a target antigen at a level which is sufficient to allow detection of the polypeptide-antigen complex. Such detection may take place under any suitable experimental conditions, such as at a temperature of at least 5° C., at least 10° C., at least 15° C., at least 20° C., at least 25° C., at least 30° C., at least 35° C., at least 40° C., at least 45° C. or at least 50° C.

Conjugates

The polypeptide of the invention may be conjugated to one or more compounds using any suitable method known in the art. Examples of compounds to which a polypeptide can be conjugated are selected from the group consisting of a radioisotope, a detectable label, a therapeutic compound, a colloid, a toxin, a nucleic acid, a peptide, a protein, a compound that increases the half life of the protein in a subject and mixtures thereof. Exemplary therapeutic agents include, but are not limited to an anti-angiogenic agent, an anti-neovascularization and/or other vascularization agent, an anti-proliferative agent, a pro-apoptotic agent, a chemotherapeutic agent or a therapeutic nucleic acid.

A toxin includes any agent that is detrimental to (e.g. kills) cells. For a description of these classes of drugs which are known in the art, and their mechanisms of action, see Goodman et al., Goodman and Gilman's The Pharmacological Basis of Therapeutics, 8th Ed., Macmillan Publishing Co., 1990. Additional techniques relevant to the preparation of immunoglobulin-immunotoxin conjugates are provided in for instance Vitetta (1993) and U.S. Pat. No. 5,194,594. Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232.

Suitable chemotherapeutic agents for forming immunoconjugates comprising polypeptides of the present invention include auristatins and maytansines, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-de-hydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)).

Examples of suitable angiogenesis inhibitors (anti-angiogenic agents) include, but are not limited to, urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF, bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2) and similar agents. Other examples of inhibitors of angiogenesis, neovascularization, and/or other vascularization are anti-angiogenic heparin derivatives and related molecules (e.g., heperinase III), temozolomide, NK4, macrophage migration inhibitory factor (MIF), cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other relevant targets (such as anti-alpha-v/beta-3 integrin and anti-kininostatin mAbs) and similar agents.

In one example, a polypeptide as described herein according to any embodiment is conjugated or linked to another polypeptide, including another polypeptide of the invention or a polypeptide comprising an immunoglobulin variable region, such as an immunoglobulin or a polypeptide derived therefrom, e.g., as described herein. Other proteins are not excluded. Additional proteins will be apparent to the skilled artisan and include, for example, an immunomodulator or a half-life extending protein or a peptide or other protein that binds to serum albumin, amongst others.

Exemplary immunomodulators include cytokines and chemokines. The term "cytokine" is a generic term for proteins or peptides released by one cell population which act on another cell as intercellular mediators. Examples of cytokines include lymphokines, monokines, growth factors and traditional polypeptide hormones. Included among the cytokines are growth hormones such as human growth hormone, N-methionyl human growth hormone, and bovine growth hormone; parathyroid hormone, thyroxine, insulin, proinsulin, relaxin, prorelaxin, glycoprotein hormones such as follicle stimulating hormone (FSH), thyroid stimulating hormone (TSH) and luteinizing hormone (LH), hepatic growth factor; prostaglandin, fibroblast growth factor, prolactin, placental lactogen, OB protein, tumor necrosis factor-α and -β; mullerian-inhibiting substance, gonadotropin-associated peptide, inhibin, activin, vascular endothelial growth factor, integrin, thrombopoietin (TPO), nerve growth factors such as NGF-B, platelet-growth factor, transforming growth factors (TGFs) such as TGF-α and TGF-β, insulin-like growth factor-I or -II, erythropoietin (EPO), osteoinductive factors, interferons such as interferon-α, -β, or -γ; colony stimulating factors (CSFs) such as macrophage-CSF (M-CSF), granulocyte-macrophage-CSF (GM-CSF); and granulocyte-CSF (G-CSF), interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21 and LIF.

Chemokines generally act as chemoattractants to recruit immune effector cells to the site of chemokine expression. Chemokines include, but are not limited to, RANTES, MCAF, MIP1-alpha or MIP1-Beta. The skilled artisan will recognize that certain cytokines are also known to have chemoattractant effects and could also be classified under the term chemokines.

Exemplary serum albumin binding peptides or protein are described in US20060228364 or US20080260757.

A variety of radionuclides are available for the production of radioconjugated proteins. Examples include, but are not limited to, low energy radioactive nuclei (e.g., suitable for diagnostic purposes), such as $^{13}C$, $^{15}N$, $^{2}H$, $^{125}I$, $^{123}I$, $^{99}Tc$, $^{43}K$, $^{52}Fe$, $^{67}Ga$, $^{68}Ga$, $^{111}In$ and the like. Preferably, the radionuclide is a gamma, photon, or positron-emitting radionuclide with a half-life suitable to permit activity or detection after the elapsed time between administration and localization to the imaging site. The present invention also encompasses high energy radioactive nuclei (e.g., for therapeutic purposes), such as $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{188}Re$. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic. Alternatively, high-energy isotopes may be generated by thermal irradiation of an otherwise stable isotope, for example as in boron neutron-capture therapy (Guan et al., 1998).

In another embodiment, the polypeptide is conjugated to a "receptor" (such as streptavidin) for utilization in cell pretargeting wherein the conjugate is administered to the patient, followed by removal of unbound conjugate from the circulation using a clearing agent and then administration of a "ligand" (e.g., avidin) that is conjugated to a therapeutic agent (e.g., a radionucleotide).

The proteins of the present invention can be modified to contain additional nonproteinaceous moieties that are known in the art and readily available. Preferably, the moieties suitable for derivatization of the protein are water soluble polymers. Non-limiting examples of water soluble polymers include, but are not limited to, polyethylene glycol (PEG), polyvinyl alcohol (PVA), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol (PPG) homopolymers, prolypropylene oxide/ethylene oxide copolymers, polyoxyethylated polyols (e.g., glycerol; POG), polyvinyl alcohol, and mixtures thereof. Polyethylene glycol propionaldehyde may have advantages in manufacturing due to its stability in water.

The polymer molecules are typically characterized as having for example from about 2 to about 1000, or from about 2 to about 300 repeating units.

For example water-soluble polymers, including but not limited to PEG, poly(ethylene oxide) (PEO), polyoxyethylene (POE), polyvinyl alcohols, hydroxyethyl celluloses, or dextrans, are commonly conjugated to proteins to increase stability or size, etc., of the protein.

PEG, PEO or POE refers to an oligomer or polymer of ethylene oxide. In the case of PEG, these oligomers or polymers are produced by, e.g., anionic ring opening polymerization of ethylene oxide initiated by nucleophilic attack of a hydroxide ion on the epoxide ring. One of the more useful forms of PEG for protein modification is monomethoxy PEG (mPEG).

Particularly preferred compounds for conjugation to the polypeptide of the present invention are set out in Table 1.

TABLE 1

Preferred compounds for conjugation

| Group | Detail |
|---|---|
| Radioisotopes (either directly or indirectly) | $^{123}$I, $^{125}$I, $^{130}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Gu, $^{68}$Gu, $^{67}$Cu, $^{75}$Br, $^{76}$Br, $^{77}$Br, $^{99m}$Tc, $^{11}$C, $^{13}$N, $^{15}$O, $^{18}$I, $^{188}$Re, $^{203}$Pb, $^{64}$Cu, $^{105}$Rh, $^{198}$Au, $^{199}$Ag or $^{177}$Lu |
| Half life extenders | Polyethylene glycol<br>Glycerol<br>Glucose |
| Fluorescent probes | Phycoerythrin (PE)<br>Allophycocyanin (APC)<br>Alexa Fluor 488<br>Cy5.5 |
| Biologics | Fluorescent proteins such as Renilla luciferase, GFP<br>Immune modulators<br>Toxins<br>An Immunoglobulin<br>Half life extenders such as albumin |
| Chemotherapeutics | Taxol<br>5-Fluorouracil<br>Doxorubicin<br>Idarubicin |

In one example of the invention, a spacer moiety is included between the compound and the polypeptide to which it is conjugated. The spacer moieties of the invention may be cleavable or non-cleavable. For example, the cleavable spacer moiety may be a redox-cleavable spacer moiety, such that the spacer moiety is cleavable in environments with a lower redox potential, such the cytoplasm and other regions with higher concentrations of molecules with free sulfhydryl groups. Examples of spacer moieties that may be cleaved due to a change in redox potential include those containing disulfides. The cleaving stimulus can be provided upon intracellular uptake of the conjugated protein where the lower redox potential of the cytoplasm facilitates cleavage of the spacer moiety.

In another example, a decrease in pH causes cleavage of the spacer to thereby release of the compound into a target cell. A decrease in pH is implicated in many physiological and pathological processes, such as endosome trafficking, tumor growth, inflammation, and myocardial ischemia. The pH drops from a physiological 7.4 to 5-6 in endosomes or 4-5 in lysosomes. Examples of acid sensitive spacer moieties which may be used to target lysosomes or endosomes of cancer cells, include those with acid-cleavable bonds such as those found in acetals, ketals, orthoesters, hydrazones, trityls, cis-aconityls, or thiocarbamoyls (see for example, U.S. Pat. Nos. 4,569,789, 4,631,190, 5,306,809, and 5,665,358). Other exemplary acid-sensitive spacer moieties comprise dipeptide sequences Phe-Lys and Val-Lys.

Cleavable spacer moieties may be sensitive to biologically supplied cleaving agents that are associated with a particular target cell, for example, lysosomal or tumor-associated enzymes. Examples of linking moieties that can be cleaved enzymatically include, but are not limited to, peptides and esters. Exemplary enzyme cleavable linking moieties include those that are sensitive to tumor-associated proteases such as Cathepsin B or plasmin. Cathepsin B cleavable sites include the dipeptide sequences valine-citrulline, phenylalanine-lysine and/or valine-alanine.

Protein Complexes

The polypeptides of the invention are preferably conjugated to one or more compounds which render them particularly suitable for use in the RED assay referred to herein. For example, the polypeptide may be associated with at least a second polypeptide (referred to hereafter as "the second polypeptide") to form a protein complex having a molecular size such that the protein complex is retained inside a permeabilised bacterial cell. The polypeptide may be associated with the second polypeptide by, for example, covalent bonds such as disulphide bridges, or by non-covalent association. "Non-covalent association" refers to molecular interactions that do not involve an interatomic bond. For example, non-covalent interactions involve ionic bonds, hydrogen bonds, hydrophobic interactions, and van der Waals forces. Non-covalent forces may be used to hold separate polypeptide chains together in proteins or in protein complexes. Thus, the polypeptide and second polypeptide may be expressed as separate polypeptides either from the same or different vectors, or one or both of the polypeptides may be expressed from DNA encoding the polypeptides that has been integrated into the bacterial cell genome.

Alternatively, the polypeptide and second polypeptide which are associated in a protein complex may be a fusion protein. As used herein, "fusion protein" refers to a hybrid protein, which consists of two or more polypeptides, or fragments thereof, resulting from the expression of a polynucleotide that encodes at least a portion of each of the two polypeptides.

Protein Complexes Retained in the Permeabilised Bacterial Cell by Molecular Size The second polypeptide may be any polypeptide having sufficient molecular size, i.e. sufficient molecular weight or molecular radius, such that at least some of the complex formed with the polypeptide being screened for a desired activity is incapable of diffusion from the permeabilised bacterial cell. Thus, the protein complex is retained within the bacterial cell following permeabilisation of the cell. The person skilled in the art will appreciate that the nature of the second polypeptide, including its molecular weight and whether it is a globular or rod (filamentous) protein, will determine its ability to prevent or inhibit diffusion of the protein complex through the bacterial cell wall. In one embodiment, the molecular weight of the second polypeptide is at least about 30 kDa, or at least about 40, 50, 60, 70, 80, 90, 100, 120, 130, 140, 150 or more kDa. In one embodiment, the second polypeptide is at least about 120 kDa.

In one embodiment, the second polypeptide forms multimers having a molecular size greater than the pore-exclusion size of the permeabilised bacterial cell. As used herein, the term "multimer" and grammatical variations thereof refer to formation of a multimeric complex between two or more distinct molecules. The multimer may comprise, for example, two or more molecules of the same protein (i.e. a homo-multimer) or a mixture of two or more different or non-identical proteins (i.e. a hetero-multimer). Proteins that form multimers suitable for use in the methods of the invention include those that form dimers, trimers, tetramers, pentamers, hexamers, and higher order multimers comprising seven or more subunits.

Multimeric proteins include homodimers, for example, PDGF receptor a, and β isoforms, erythropoietin receptor, MPL, and G-CSF receptor, heterodimers whose subunits each have ligand-binding and effector domains, for example, PDGF receptor αβ isoform, and multimers having component subunits with disparate functions, for example, IL-2, IL-3, IL-4, IL-5, IL-6, IL-7, and GM-CSF receptors. Non-limiting examples of other multimeric proteins that may be utilized in the methods of the present invention include factors involved in the synthesis or replication of DNA, such as DNA polymerase proteins involved in the production of mRNA, such as TFIID and TFIIH; cell, nuclear and other membrane-associated proteins, such as hormone and other signal transduction receptors, active transport proteins and ion channels, multimeric proteins in the blood, including hemoglobin, fibrinogen and von Willabrand's Factor; proteins that form structures within the cell, such as actin, myosin, and tubulin and other cytoskeletal proteins; proteins that form structures in the extra cellular environment, such as collagen, elastin and fibronectin; proteins involved in intra- and extra-cellular transport, such as kinesin and dynein, the SNARE family of proteins (soluble NSF attachment protein receptor) and clathrin; proteins that help regulate chromatin structure, such as histones and protamines, Swi3p, Rsc8p and moira; multimeric transcription factors such as Fos, Jun and CBTF (CCAAT box transcription factor); multimeric enzymes such as acetylcholinesterase and alcohol dehydrogenase; chaperone proteins such as GroE, Gro EL (chaperonin 60) and Gro ES (chaperonin 10); anti-toxins, such as snake venom, botulism toxin, *Streptococcus* super antigens; lysins (enzymes from bacteriophage and viruses); as well as most allosteric proteins. In one embodiment, the multimeric protein is an *E. coli* protein. Non-limiting examples of *E. coli* proteins that form multimers include L-rhamnose isomerase (RhnA; for example NCBI accession CAA43002), β-galactosidase (β-gal; for example NCBI accession YP 001461520), betaine aldehyde dehydrogenase (BetB; for example NCBI accession AAA23506), glutamate-5-kinase (G5K; for example NCBI accession AAB08662), glutathione synthase (GshB; for example NCBI accession AP_003504), and a medium chain aldehyde dehydrogenase (YdcW; for example NCBI accession AP_002067).

In one embodiment, the polypeptide has a molecular size sufficient to retain the polypeptide within the bacterial cell wall. Thus, the person skilled in the art will appreciate that such a polypeptide need not necessarily be associated with a second polypeptide in order to retain the polypeptide within the permeabilised bacterial cell.

DNA Binding Proteins

The present inventors have found that DNA is retained within a bacterial cell following permeabilisation. Thus, in one embodiment, the polypeptide is associated with a DNA-binding protein to form a protein complex that binds DNA and that is retained inside the bacterial cell. As used herein, "DNA-binding protein" refers to any protein comprising a DNA-binding domain comprising at least one motif that recognizes double-stranded or single-stranded DNA. As would be known to the person skilled in the art, DNA-binding domains include helix-turn-helix, zinc finger, leucine zipper, winged helix, winged helix turn helix, helix-loop-helix, immunoglobulin fold recognizing DNA, or B3 domains. Associating the polypeptide with a DNA-binding protein advantageously provides for enhanced recovery of DNA, for example a plasmid, encoding the polypeptide in the screening methods of the invention.

Examples of DNA binding proteins include bacterial competence proteins such as, but not limited to, *E. coli* DNA binding proteins, *Neisseria gonorrhoeae* DNA binding proteins, for example ComE, Adenovirus E2 proteins, AraC transcription factor, basic helix-loop-helix transcription factors, basic-leucine zipper transcription factors, butyrate response factor, centromere protein B, COUP transcription factors, early growth response transcription factors, G-box binding factors, GATA transcription factors, HMGA proteins, homeodomain proteins, I-kappa B proteins, integration host factors, interferon regulatory factors, interferon-stimulated gene factor 3, Kruppel-like transcription factors, leucine responsive regulatory protein, matrix attachment region binding proteins, methyl-CpG-binding protein, MutS homolog 2 protein, myeloid-lymphoid leukaemia protein, NF-Kappa B, NF1 transcription factors, nuclear respiratory factors, oncogene protein p55, origin recognition complex, paired box transcription factors, POU domain factors, proto-oncogene factors, Rad51 recombinase, Rad52 DNA repair and recombination protein, replication protein A, replication protein C, retinoblastoma protein, Smad proteins, SOX transcription factors, T-box domain proteins, TCF transcription factors, telomere-binding proteins, Toll-like receptor 9, trans-activators, and winged-helix transcription factors. In one embodiment, the DNA binding protein is an *E. coli* DNA binding protein. In another embodiment, the DNA binding protein is a *Neisseria gonorrhoeae* protein, for example ComE.

Cell Wall Binding Proteins

The polypeptide may be associated with a bacterial cell wall-binding protein. The skilled person will understand that the choice of a cell wall-binding protein would depend on the host cell species, as different bacteria have different cell wall compositions. While bacteria have cell walls made up of peptidoglycan (PG), chemical modifications between species can affect cross-species binding. The skilled person will readily be able to determine cell wall-binding proteins suitable for use in a particular bacterial species.

Bacterial cell wall-binding proteins include proteins known to have a domain structure, whereby part of the polypeptide chain in the native structure is able to recognise and bind specific molecules or molecular conformations on the bacterial cell wall. Thus, the term "bacterial cell wall-binding protein" includes a protein domain which is part of the protein which specifically binds to the bacterial cell wall. Examples of bacterial cell wall-binding proteins include the cell wall hydrolases as coded by bacteriophages, cell wall hydrolases of bacteria and different autolysins. Further encompassed are receptor molecules coded by the DNA of bacteriophages and other viruses. Where the bacterial cell wall-binding protein is from hydrolytic enzymes of bacteriophage origin, which are capable of specific binding to bacteria, the cell wall-binding protein maintain their binding ability but preferably have no significant hydrolytic activity.

In one embodiment, the cell wall-binding protein binds non-covalently to the cell wall of *E. coli*. For example, for an *E. coli* host cell there are endogenous PG-binding proteins with a conserved ~100 amino acid PG-binding domain occurring in PAL, OmpA, YiaD, YfiB, and MotB (Parsons et al., 2006). However, proteins from other organisms have been shown to be well expressed in *E. coli* and to bind the cell wall with high affinity, for example the ~70 amino acid PG-binding domain from *Pseudomonas* φKZ phage (KzPG) (Briers et al., 2009). Thus a PG-binding domain from a protein that binds PG may be used as a bacterial cell wall-binding protein in the methods of the invention.

In an exemplary embodiment, the PG-binding domain may be fused to the polypeptide of the invention and expressed in the cytosol of the bacterial cell. Upon membrane permeabilisation, the PG-binding domain binds to the cell wall resulting in the retention of the polypeptide of interest within the permeabilised cell. To potentially further enhance retention of the polypeptide of interest within the cell, the skilled person will understand that the polypeptide may be associated with a DNA-binding protein in addition to a bacterial cell wall-binding protein.

Alternatively, the polypeptide may be associated with a protein that is capable of linking covalently to the bacterial cell wall. Preferably the protein comprises a periplasmic-targeting signal. Thus, the polypeptide is expressed in the cytosol of the bacterial cell, but targeted to the periplasm where it is linked to the cell wall before membrane permeabilisation.

By way of non-limiting example, the bacterial cell wall-binding protein that attaches to the cell wall covalently may be a lipoprotein capable of binding to the cell wall and which lacks a functional N-terminal signal sequence necessary for outer membrane attachment. For example, the lipoprotein may be *E. coli* LPP. LPP is an abundant *E. coli* protein that forms a trimeric coiled-coil. In its native form, one end is tethered to the outer membrane via lipidation and the other is covalently bound to the cell wall via a C-terminal lysine. The lipoprotein may further comprise a sequence which targets the lipoprotein to the periplasm, for example an OmpF periplasmic targeting sequence. In one embodiment, the lipoprotein is *E. coli* lipoprotein lacking a functional N-terminal signal sequence necessary for outer membrane attachment.

In light of the teaching of the present specification, the person skilled in the art will be able to identify or design proteins that attach covalently to the bacterial cell wall and that are suitable for use in the methods of the present invention.

In one embodiment of the invention, the polypeptide of the invention is a fusion polypeptide comprising a KzPG domain and one or more other domains selected from a spacer, SNAP and/or DBP. In one particular embodiment, the fusion polypeptide comprises one or more spacers and the KzPG, SNAP and DBP domains.

Polynucleotides

The present invention also provides a polynucleotide encoding a polypeptide of the invention. Preferably, the polynucleotide is an isolated or recombinant polynucleotide.

The term "isolated polynucleotide" is intended to mean a polynucleotide which has generally been separated from the polynucleotide sequences with which it is associated or linked in its native state. Preferably, the isolated polynucleotide is at least 60% free, more preferably at least 75% free, and more preferably at least 90% free from other components with which it is naturally associated. Furthermore, the term "polynucleotide" is used interchangeably herein with the terms "nucleic acid molecule", "gene" and "mRNA".

The term "recombinant" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide. A recombinant polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components.

"Polynucleotide" refers to an oligonucleotide, a polynucleotide or any fragment thereof. It may be DNA or RNA of genomic or synthetic origin, double-stranded or single-stranded, and combined with carbohydrate, lipids, protein, or other materials to perform a particular activity defined herein.

DNA encoding a polypeptide comprising a variable region can be isolated using standard methods in the art. For example, primers can be designed to anneal to conserved regions within a variable region that flank the region of interest, and those primers can then be used to amplify the intervening nucleic acid, e.g., by PCR. Suitable methods and/or primers are known in the art and/or described, for example, in Borrebaeck (ed), 1995 and/or Froyen et al., 1995. Suitable sources of template DNA for such amplification methods can be derived from, for example, hybridomas, transfectomas and/or cells expressing proteins comprising a variable region, e.g., as described herein.

The polynucleotide of the invention can encode the entire polypeptide of the invention. Alternatively, the polynucleotide can encode a single heavy or light chain of the polypeptide of the invention. Thus, two polynucleotides, each encoding one of the heavy or light chains, can be produced and expressed in a single cell in order to produce the polypeptide of the invention.

Preferably, the polynucleotides encode the scaffold region of the variable regions, and also one or more CDRs. Most preferably, the polynucleotides of the invention encode the scaffold region of the variable regions and all three CDRs. The polynucleotides of the invention may be mutagenised in order to produce variety in the amino acid sequences of the CDRs and possibly also in the amino acid sequences of the scaffold regions. The person skilled in the art will be aware of suitable methods for this purpose.

The polynucleotide of the invention can also encode a protein conjugate which is or is capable of being conjugated to a polypeptide of the invention, as described herein.

Polypeptide Production

The polypeptides disclosed herein can be synthesised by any methods known in the art, such as by the production and recovery of recombinant polypeptides, and by the chemical synthesis of the polypeptides. Thus, the present invention also provides a method of producing the polypeptides of the invention.

The polypeptides of the invention can be produced under reducing, or non-reducing conditions. Preferably, the polypeptides of the invention are produced under reducing conditions, such as in the cytoplasm of a host cell.

In the case of a recombinant polypeptide, nucleic acid encoding same is preferably placed into one or more expression vectors, which are then transfected into host cells, for example E. coli cells, yeast cells, insect cells, or mammalian cells, such as simian COS cells, Chinese Hamster Ovary (CHO) cells, or myeloma cells that do not otherwise produce immunoglobulin protein, to obtain the synthesis of proteins in the recombinant host cells. Review articles on recombinant expression in bacteria of DNA encoding the immunoglobulin include Skerra et al, (1993) and Plückthun, (1992). Molecular cloning techniques to achieve these ends are known in the art and described, for example in Ausubel or Sambrook. A wide variety of cloning and in vitro amplification methods are suitable for the construction of recombinant nucleic acids. Methods of producing recombinant immunoglobulins are also known in the art. See U.S. Pat. Nos. 4,816,567; 5,225,539, 6,054,297, 7,566,771 or 5,585,089.

Following isolation, the nucleic acid encoding a polypeptide of the invention is preferably inserted into an expression construct or replicable vector for further cloning (amplification of the DNA) or for expression in a cell-free system or in cells. Preferably, the nucleic acid is operably linked to a promoter, As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Preferred promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Cell free expression systems are also contemplated by the present invention. For example, a nucleic acid encoding a polypeptide of the invention can be operably linked to a suitable promoter, e.g., a T7 promoter, and the resulting expression construct exposed to conditions sufficient for transcription and translation. Typical expression vectors for in vitro expression or cell-free expression have been described and include, but are not limited to the TNT T7 and TNT T3 systems (Promega), the pEXP1-DEST and pEXP2-DEST vectors (Invitrogen).

Many vectors for expression in cells are available. The vector components generally include, but are not limited to, one or more of the following: a signal sequence, a sequence encoding protein of the present invention (e.g., derived from the information provided herein), an enhancer element, a promoter, and a transcription termination sequence. The skilled artisan will be aware of suitable sequences for expression of a protein. For example, exemplary signal sequences include prokaryotic secretion signals (e.g., pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

In a preferred embodiment, the polynucleotide encoding the polypeptide of the invention is inserted into a vector which is particularly suitable for expression in the RED system described herein. Thus, the vector may be particularly suitable for expression within a bacterial cell. For example, the vector may comprise a site for inserting into the vector a polynucleotide encoding a polypeptide of the invention, and an open reading frame encoding a second polypeptide which associates with the polypeptide of the invention to form a protein complex that can be retained inside or can attach to the cell wall of a permeabilised bacterial cell. Suitable vectors are described in WO2011/075761.

Preferably, the vector is also capable of replicating within the bacterial cell independently of the host's genome. Suitable vectors include plasmids, viruses and cosmids as well as linear DNA elements, such as the linear phage N15 of E. coli, and/or extrachromosomal DNA that replicates independently of a bacterial cell genome.

The skilled person will be able to readily determine bacterial strains suitable for expressing polypeptides in the methods of the invention. Those skilled in the art would understand that Gram-negative bacteria are suitable for use in the methods of the invention, including, for example, Salmonella, E. coli, Shigella, Campylobacter, Fusobacterium, Bordetella, Pasteurella, Actinobacillus, Haemophilus and Histophilus. In a preferred embodiment, the Gram-negative bacteria is E. coli.

Exemplary promoters that may be included in the vector of the invention include those active in prokaryotes (e.g., phoA promoter, β-lactamase and lactose promoter systems, alkaline phosphatase, a tryptophan (trp) promoter system, and hybrid promoters such as the tac promoter). These promoters are useful for expression in prokaryotes including eubacteria, such as Gram-negative or Gram-positive organisms, for example, Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis, Pseudomonas such as P. aeruginosa, and Streptomyces. Preferably, the host is E. coli. One preferred E. coli cloning host is E. coli 294 (ATCC 31,446), although other strains such as E. coli B, E. coli X 1776 (ATCC 31,537), and E. coli W3110 (ATCC 27,325), DH5α or DH10B are suitable.

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Typical promoters suitable for expression in insect cells include, but are not limited to, the OPEI2 promoter, the insect actin promoter isolated from *Bombyx muni*, the *Drosophila* sp. dsh promoter (Marsh et al., 2000) and the inducible metallothionein promoter. Preferred insect cells for expression of recombinant proteins include an insect cell selected from the group comprising, BT1-TN-5B1-4 cells, and *Spodoptera frugiperda* cells (e.g., sf19 cells, sf21 cells). Suitable insects for the expression of the nucleic acid fragments include but are not limited to *Drosophila* sp. The use of *S. frugiperda* is also contemplated.

Means for introducing the isolated nucleic acid molecule or a gene construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein of the invention may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Scaffold Sequences

To date, sequences of the structural regions of intrabodies (antibody molecules whose sequences have been engineered or evolved for higher stability such that they may be productively folded in the cytoplasm), i.e. the non-CDR sequences, have differed substantially from the cognate germline genomic sequence. As disclosed herein, the inventors have screened for, and determined, sequences of human antibody variable regions that are identical, or closely related to, the cognate germline genomic sequence, and that allow correct folding and increased stability when expressed in a non-oxidising environment. Preferred sequences for use in the present invention are described below. For any of the variable region sequences described herein, it will be appreciated that the person skilled in the art will be able to identify the CDRs (e.g., many of which are identified on the NCBI database) and the remaining scaffold region. Particular examples of CDRs in each of the variable regions described herein are shown in FIG. 7.

IGHV3-23

In a preferred embodiment, the polypeptide of the present invention comprises a heavy chain variable region ($V_H$) of the $V_H3$ family of immunoglobulin variable domains. Preferably, the $V_H$ is IGHV3-23 (SEQ ID NO: 3).

IGHV3-23, also known as DP-47, belongs to the $V_H3$ family of human Ig variable domains. The $V_H3$ family has 43% (22/51) of the functional members of the $V_H$ genes and IGHV3-23 has been cited as the most highly expressed gene in the VH repertoire (Stewart et al., 1993). It is also found at a high frequency in productive Ig rearrangements in B cells (Brezinschek et al., 1997). Because of its high frequency in native Ig repertoires, it has also been frequently isolated from phage display libraries of human V regions (Griffiths et al., 1994). It has also been used as a scaffold partner in synthetic libraries (Jirholt et al., 1998; Pini et al., 1998; Soderlind et al., 2000; Ge et al., 2010). IGHV3-23 was selected as the heavy chain variable region partner in the present inventors' study to identify a stable, soluble antibody variable region scaffold.

Preferably, the polypeptide of the invention comprises an antibody heavy chain variable region ($V_H$) comprising a scaffold region which is at least 90% identical to the scaffold region of IGHV3-23 as set out in SEQ ID NO: 3. For example, the scaffold region may be at least 95%, at least 96%, at least 97%, at least 98%, at least 99%, or 100% identical to the scaffold region of IGHV3-23 as set out in SEQ ID NO: 3. Preferably, the polypeptide of the invention comprises an antibody heavy chain variable region ($V_H$) comprising a scaffold region which is at least 96% identical to the scaffold region of IGHV3-23 as set out in SEQ ID NO: 3. The scaffold region comprises all of the variable region residues excluding the CDR residues. Thus, the polypeptide of the invention may comprise a scaffold region comprising amino acids 1-25, 33-51, 60-98 of SEQ ID NO: 3 (or a scaffold region whose amino acid sequence is at least 90%, at least 95%, at least 96%, at least 97%, at least 98%, at least 99%, or 100% identical to the sequence of these amino acids). Alternatively, the polypeptide of the invention may comprise a scaffold region comprising amino acids 1-25 and 33-98 of SEQ ID NO: 3 (or a scaffold region whose amino acid sequence is at least 90%, at least 95%, at least 96%, at least 97%, at least 98%, at least 99%, or 100% identical to the sequence of these amino acids). In another alternative, the polypeptide of the invention may comprise a scaffold region comprising amino acids 1-51 and 60-98 of SEQ ID NO: 3 (or a scaffold region whose amino acid sequence is at least 90%, at least 95%, at least 96%, at least 97%, at least 98%, at least 99%, or 100% identical to the sequence of these amino acids).

The polypeptides of the invention may comprise any CDR sequence or sequences. Thus, the polypeptides of the invention may comprise the CDR sequences of IGHV3-23 (i.e., amino acids 26-32, 52-59 of SEQ ID NO: 3). Alternatively, the polypeptides of the invention may comprise any other CDR sequence or sequences. Thus, the scaffold region of the $V_H3$ variable domain can serve as a template into which any given CDR sequences can be inserted. The CDR sequences may be randomly generated. Alternatively or in addition, the CDR sequences may be semi-randomly generated (by randomly assigning to each particular amino acid position in the CDR an amino acid residue selected from a subset of all possible amino acids, the subset being known to be necessary or particularly favoured at a given amino acid position in the CDR).

Alternatively, the CDR sequences may be derived from another antibody. Thus, CDRs from e.g. a human antibody can be grafted onto the $V_H3$ variable domain scaffold. It will be appreciated that the person skilled in the art can use various methods to ensure that a scaffold region as defined herein comprises one or more CDR sequences taken from a human antibody. Preferably, such methods include cloning one or more CDR-encoding sequences into a polynucleotide encoding a polypeptide of the invention, as described in more detail herein, below. The CDR-encoding sequences may additionally be varied by targeted or random mutagenesis, in order to provide a plurality of polypeptides comprising a plurality of different CDR sequences. Such methods can be applied to any one or combination of CDR1, CDR2 and CDR3.

Sequences of any one or more of the CDRs CDR1, CDR2 and CDR3 may be introduced into the variable domain scaffolds described herein, in any combination. Preferably, at least the sequence of a CDR3 is introduced into the $V_H3$ variable domain scaffold described herein.

In addition, the length of the CDR sequences introduced into the $V_H3$ variable domain scaffold described herein can be varied. For example, a CDR3 sequence of 15, 14, 13, 12, 11, 10, 9, 8, 7, 6, 5, 4, 3, 2 or 1 amino acids can be inserted into the scaffold. The present inventors have found that a shortened CDR3 sequence of less than 12, such as 11, 10, 9, 8, 7, 6, 5, 4, 3, 2 or 1, and most preferably 7 amino acids in length displays enhanced stability.

IGK and IGL Light Chain Partners to IGHV3-23

The inventors of the present invention, by applying only the criteria that the scFv fusion is soluble in their RED platform (in contrast to previously performed functional screens which required binding of the antibody to an antigen target in vivo and which therefore screened antibodies that were substantially mutated from their respective germline sequences) were able to screen naïve light chains that had not been mutated within the V region. Therefore, they were able to identify germline sequences that conferred solubility upon IGHV3-23 scFv fusions. This has the significant benefit of ensuring that an artificial scaffold library constructed of the $V_L$ and $V_H$ domains is identical in sequence to abundant human antibody proteins, thereby minimizing immune recognition and rejection on prolonged exposure to any derivatives.

Accordingly, the polypeptide of the invention preferably comprises an antibody light chain variable region ($V_L$) of the $V_L\lambda1$, 3 or 6 families of immunoglobulin variable domains combined with the human germline IGHV3-23 sequence. Preferred $V_L\lambda1$, 3 or 6 family members include IGLV1-40 (as set out in SEQ ID NO: 18), IGLV1-44 (as set out in SEQ ID NO: 21), IGLV1-47 (as set out in SEQ ID NO: 24), IGLV1-51 (as set out in SEQ ID NO: 15), IGLV3-1 (as set out in SEQ ID NO: 6), IGLV3-19 (as set out in SEQ ID NO: 27), IGLV3-21 (as set out in SEQ ID NO: 9) and IGLV6-57 (as set out in SEQ ID NO: 12). Thus, the polypeptide of the invention preferably comprises an antibody light chain variable region ($V_L$) comprising a scaffold region which is at least 90% identical to the scaffold region of any of IGLV1-40 (as set out in SEQ ID NO: 18), IGLV1-44 (as set out in SEQ ID NO: 21), IGLV1-47 (as set out in SEQ ID NO: 24), IGLV1-51 (as set out in SEQ ID NO: 15), IGLV3-1 (as set out in SEQ ID NO: 6), IGLV3-19 (as set out in SEQ ID NO: 27), IGLV3-21 (as set out in SEQ ID NO: 9) and IGLV6-57 (as set out in SEQ ID NO: 12). For example, the scaffold region may be at least 95%, at least 96%, at least 97%, at least 98%, at least 99%, or 100% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV1-51 (as set out in SEQ ID NO: 15), IGLV3-1 (as set out in SEQ ID NO: 6), IGLV3-19 (as set out in SEQ ID NO: 27), IGLV3-21 (as set out in SEQ ID NO: 9) and IGLV6-57 (as set out in SEQ ID NO: 12).

Most preferably the $V_L$ partner of IGHV3-23 is IGLV3-1 (SEQ ID NO: 6). Thus, the polypeptide of the invention preferably comprises an antibody light chain variable region ($V_L$) comprising a scaffold region which is at least 90% identical to the scaffold region of IGLV3-1 (SEQ ID NO: 6). For example, the scaffold region may be at least 95%, at least 96%, at least 97%, at least 98%, at least 99%, or 100% identical to the scaffold region of IGLV3-1 (SEQ ID NO: 6). The scaffold region of IGLV3-1 may comprise amino acids 1-23, 32-48, 56-89 of SEQ ID NO: 6. Accordingly, the polypeptide of the invention may comprise an antibody light chain variable region ($V_L$) comprising a scaffold region comprising amino acids 1-23, 32-48, 56-89 of SEQ ID NO: 6 (or a scaffold region whose amino acid sequence is at least 90%, at least 95%, at least 96%, at least 97%, at least 98%, at least 99%, or 100% identical to the sequence of these amino acids).

A preferred example of a polynucleotide sequence encoding an IGLV3-1::IGHV3-23 scaffold with variable CDR3 regions, and the corresponding, translated amino acid sequence is illustrated in FIG. 8.

Preferably, the polypeptide of the invention comprises the scaffold region of the $V_L$ variable domain (e.g., the polypeptide of the invention may comprise the scaffold region of IGHV3-1, e.g., amino acids 1-23, 32-48, 56-89 of SEQ ID NO: 6). Again, the polypeptides of the invention may comprise any CDR sequence or sequences. Thus, the polypeptides of the invention may comprise the CDR sequences of any of IGLV1-40, IGLV1-44, IGLV1-47, IGLV1-51, IGLV3-1, IGLV3-19, IGLV3-21, and/or IGLV6-57. Alternatively, the polypeptides of the invention may comprise any other CDR sequence or sequences. Thus, the scaffold region of the $V_L$ variable domain can serve as a template into which any given CDR sequences can be inserted, as described above in respect of the $V_H3$ variable domain scaffold. Thus, the CDR sequences may be randomly generated. Alternatively or in addition, the CDR sequences may be semi-randomly generated (by randomly assigning an amino acid residue selected from a subset of all possible amino acids to each particular amino acid position in the CDR, the subset being known to be particularly favoured at a given amino acid position in the CDR).

Alternatively, the CDR sequences may be derived from another antibody. Thus, CDRs from e.g. a human antibody can be grafted onto the $V_L$ variable domain scaffold. It will be appreciated that various different methods are available to the person skilled in the art to ensure that a scaffold region as defined herein comprises one or more CDR sequences taken from a human antibody. In addition, the CDR sequences of a human antibody may be randomly mutagenised before insertion into the $V_L$ variable domain scaffold described herein.

Any one or more of the sequences of CDR1, CDR2 and CDR3 may be inserted into the $V_L$ variable domain scaffold described herein, in any combination. Preferably, at least the sequence of a CDR3 is inserted into the $V_L$ variable domain scaffold described herein.

In addition, the length of the CDR sequences inserted into the $V_L$ variable domain scaffold described herein can be varied. For example, a CDR3 sequence of 15, 14, 13, 12, 11, 10, 9, 8, 7, 6, 5, 4, 3, 2 or 1 amino acids can be inserted into the scaffold. The present inventors have found that a shortened CDR3 sequence of less than 12, such as 11, 10, 9, 8, 7, 6, 5, 4, 3, 2 or 1, and most preferably 7 amino acids in length displays enhanced stability.

Synthetic Polypeptide Libraries

A library of polypeptide sequences may be cloned and expressed in a variety of protein display platforms to select for affinity proteins against a desired target. Thus, the invention provides a library comprising a plurality of polypeptides of the invention. In a preferred embodiment, the libraries may be prepared by identifying a "parent" polypeptide and/or polynucleotide sequence and altering that sequence to create a plurality of variant sequences to form the library. The alteration may be performed by any suitable means, for example, by site directed mutagenesis, or random mutagenesis. Suitable methods of library construction are known in the art.

As indicated above, the variable domains can be cloned directly from a biological source, such that both the structural sequences and the CDRs are present as formed by V(D)J recombination. Alternatively, the antibody library may be partly, or fully, synthetic, with the CDR and the structural regions assembled de novo. For example, a single artificial scaffold representing a pairing of commonly expressed, or particularly stable, antibody genes might be recoded for optimized expression in a host organism. The entire scaffold and CDRs may even be assembled in a single reaction using overlapping oligonucleotides, such as described by Ge et al. (2010).

Methods for building diversity in the antigen-binding CDRs have been fully described by the prior art. They include—sourcing the CDRs from mRNA, from either naïve or pre-immunised immune cells; designing and synthesizing CDRs through analysis of collated antibody sequences; designing and synthesizing CDRs with a weighted amino acid distribution based on collated antibody sequences; adopting a randomized, non-biased CDR region.

Each Ig domain, $V_L$ and $V_H$, has three CDR regions, CDR1, CDR2 and CDR3, that are of varying lengths and have different frequencies of interfacial contacts with the antigen. The most variant CDR in vivo for both $V_L$ and $V_H$ is CDR3, whose loop is formed by recombination between the exon junction of the V-J domains ($V_L$) or the V-D-J domains ($V_H$). This is representative of the naïve immune system. However, once a B-cell has been stimulated for expansion then somatic hypermutation often acts to diversify CDRs 1 and 2 as well.

However, for a cloned scFv library of variable domains built into a single, or a few, $V_L$ and $V_H$ scaffolds it is common for CDR diversity to be limited to CDR3, with amino acid composition and loop length variation accounting for target binding.

In the instance of the stable polypeptides described by the invention this allows the entirety of the scFv, other than the naturally varying CDR3 loop region, to be identical, or nearly so, to the germline sequence of the cognate antibody genes. This allows screening for affinity proteins that closely resemble the human naïve antibody repertoire, thereby minimizing sequence divergence of an engineered scaffold that might trigger patient immune recognition. Thus, in the present invention, a polypeptide library may comprise polypeptides differing from one another only in the CDR3 sequence.

An artificial antibody library may be built utilising a single scaffold, or it may be constituted by a plurality of scaffolds. Thus, the library of the present invention may comprise one or more polypeptides having a particular combination of heavy and light chain variable region scaffolds disclosed herein and one or more polypeptides having another, different combination of heavy and light chain variable region scaffolds disclosed herein.

For example, the library may comprise:

one or more polypeptides comprising an antibody heavy chain variable region ($V_H$) comprising a scaffold region which is at least 90% identical to the scaffold region of IGHV3-23 as set out in SEQ ID NO: 3, and an antibody light chain variable region ($V_L$) comprising a scaffold region which is at least 90% identical to the scaffold region of IGLV3-1 (as set out in SEQ ID NO: 6), wherein the $V_H$ and the $V_L$ are capable of forming an antigen-binding site; and one or more polypeptides comprising an antibody heavy chain variable region ($V_H$) comprising a scaffold region which is at least 90% identical to the scaffold region of IGHV3-23 as set out in SEQ ID NO: 3, and an antibody light chain variable region ($V_L$) comprising a scaffold region which is at least 90% identical to the scaffold region of any one or more of IGLV1-40 (as set out in SEQ ID NO: 18), IGLV1-44 (as set out in SEQ ID NO: 21), IGLV1-47 (as set out in SEQ ID NO: 24), IGLV1-51 (as set out in SEQ ID NO: 15), IGLV3-19 (as set out in SEQ ID NO: 27), IGLV3-21 (as set out in SEQ ID NO: 9) or IGLV6-57 (as set out in SEQ ID NO: 12), wherein the $V_H$ and the $V_L$ are capable of forming an antigen-binding site.

Thus, the library of the present invention may comprise one or more polypeptides having any combination of heavy and light chain variable region scaffolds disclosed herein.

A plurality of scaffolds may represent the two broad classes of human Ig genes, namely a heavy chain pairing with the κ and λ lambda light chain classes, or they may be a mixture of a single light chain scaffold with multiple heavy chains, or a mixture of light chain scaffold and a single heavy chain. A plurality of scaffolds could also be drawn from a single member that is the most stable representative of the different subclasses, or could be a combination of only the most stable of scaffolds, belonging to any class.

In the instance of the invention, a polypeptide library is preferably composed of scaffold regions that are identical, or nearly identical (for example, at least 90, 95, 96, 97, 98 or 99% identical), to the scaffold region of the human IGHV3-23 gene, operably linked to a sequence that is identical, or nearly identical (for example, at least 90, 95, 96, 97, 98 or 99% identical), to the scaffold region of the human genes for IGLV1-40, IGLV1-44, IGLV1-47, IGLV1-51, IGLV3-1, IGLV3-19, IGLV3-21 or IGLV6-53. The library may constitute a single scaffold pairing of a heavy and light chain gene in a recognized format (e.g. scFv) or may be a scaffold pairing of the IGHV3-23 gene with one or more of the aforementioned light chain genes. A library constructed from these scaffolds is demonstrated by the inventors to have superior and desirable stability and solubility properties in the *E. coli* cytoplasm. In effect, it is a superior intrabody library whose variation from the ideal sequence homology to their cognate germline genes exists only in the CDR loop regions.

It would be recognised by the person skilled in the art that the method of screening for cytoplasmic soluble polypeptides that have VL partners for the VH gene, IGHV3-23, could also be applied for screening for soluble partners of other variable regions, either VL or VH. Furthermore, the method of screening for cytoplasmic soluble polypeptides could be iterated using variants of a single scaffold to find mutations that increase their stability and solubility. For example, any of the scaffold pairs that have been identified (IGHV3-23 with; IGLV1-40, IGLV1-44, IGLV1-47, IGLV1-51, IGLV3-1, IGLV3-19, IGLV3-21 or IGLV6-57) could be used as the template for a further library of variants on a single scaffold with the intention of conducting the cytoplasmic screen at a temperature where the parental scaffold would have poor solubility.

It would also be recognized by experienced practitioners in the art that a polypeptide library could also be constituted by aforementioned polypeptides present at less than 100% abundance. A library composed of 50% polypeptides described by the invention; or 25% polypeptides described by the invention; or 10% polypeptides described by the invention, would still function to yield affinity proteins of desired stability properties. Thus, the polypeptide library of the invention may comprise polypeptides other than those of the present invention.

Furthermore, although the inventors have surprisingly found that a scFv scaffold that is identical or near identical in sequence to the human germline genes for the VH and VL domains described has superior and desirable stability and solubility properties in the *E. coli* cytoplasm, it would be recognized by experienced practitioners in the art that these sequences could be obtained to be more polymorphic than reported, yet still function as affinity proteins with desired stability properties. Therefore, the present invention provides a scaffold region with a sequence that diverges from the scaffold region sequences disclosed herein by up to 10%, or 5%, and that still functions to yield affinity proteins with desired solubility and/or stability properties. Thus, the polypeptides of the invention can comprise scaffold region sequences that are at least 90%, 95%, 96%, 97%, 98% or 99% identical to any of the scaffold region sequences disclosed herein.

The present invention provides both a polypeptide library and a polynucleotide library (for example, a DNA library). DNA libraries are a collection of recombinant vectors containing DNA inserts (DNA fragments) that encode the polypeptide. The origin of the DNA inserts can be genomic, cDNA, synthetic or semi-synthetic.

The cloning and construction of DNA libraries encoding polypeptides of the invention can be performed using methods known in the art. For example, Lutz and Patrick (2004) have reviewed methods of generating library variability and strategies for gene recombination for use in protein engineering. For screening of displayed polypeptide variants, the strategies used for surface-displayed libraries could be adopted and adapted for the methods of the present invention (Becker et al., 2004; Kenrick et al., 2007; Miller et al., 2006; Daugherty et al., 2000).

A library of nucleic acids can be introduced into a plurality of bacterial cells resulting in the expression of a member of the library in each of the bacterial cells. In addition to being expressed, the polypeptides are retained within the permeabilised bacterial cell, or attached to the cell wall, in order to evaluate their function or characteristic. Nucleic acid libraries of a polypeptide, for example, can be generated through a variety of methods including through the introduction of mutations such as point mutations, deletions, and insertions, or through recombination events. Methods for the generation of libraries of variants are known in the art and include error-prone PCR, synthesis of DNA in DNA repair-compromised bacteria, and chemical modification of DNA. Methods for the generation of libraries through recombination are known in the art and include gene shuffling, assembly of DNA in highly recombinogenic bacteria, synthetic nucleic acid library assembly, etc., or any combination thereof. In this way a library of polynucleotides encoding polypeptides can be introduced into a plurality of bacterial cells resulting in the expression of one or members of the library in each of the bacterial cells.

In some embodiments, a library comprises two or more variants of a polypeptide wherein each variant comprises a unique polypeptide with a minor change in amino acid sequence, for example, in a CDR sequence. A library can have at least 2, at least 5, at least 10, at least 50, at least 100, at least 1000, at least 10,000, at least 100,000, at least 1,000,000, at least $10^7$ or more members.

Screening Methods

The polypeptide (or antibody) libraries disclosed herein can be used to screen for a polypeptide that binds to a target molecule. It will be appreciated that polypeptide may be screened for or selected in the context of a library of cells each expressing a different polypeptide or polypeptide variant, or in the context of a single type of cell expressing a single polypeptide. The term "target molecule" refers to a molecule that binds to and/or is modified by the polypeptide and may be for example an antigen, an enzyme, an antibody, a receptor, etc. Thus, "target molecule" can be used to refer to a substrate such as an enzymatic substrate or a molecule that is being evaluated for binding (e.g., a ligand, eptiope, antigen, multimerization partner such as a homo or hetero dimeric partner, etc., or any combination thereof).

Thus, the invention provides a method of screening for a polypeptide that binds to a target polypeptide, the method comprising contacting a polypeptide of the invention with the target polypeptide, and determining whether the polypeptide of the invention binds to the target polypeptide. Preferably, a plurality of polypeptides of the invention is used in such methods.

A number of suitable screening methods are known in the art, which can be used in accordance with the present invention.

For example, the method may comprise a protein display method. The earliest method of protein display is phage display (Smith, 1985), in which the protein of interest is fused to one of the outer-coat proteins of the phage where it may be present along with wild-type copies of the protein. For example, a display platform based on the M13 filamentous phage using fusions to the pIII protein can be used.

Other suitable display methods include 'in vitro' display methods where the polypeptide is expressed using a cellular translation extract, and the coupling between the polypeptide and the coding nucleic acid is achieved through physical linkage (e.g. ribosome display, mRNA display) or through attachment to a common scaffold or encapsulation within a membrane, such as in in vitro compartmentalization (IVC) where the mRNA is translated within a micelle suspension that may also include a microbead (magnetic or sepharose) capture system for both mRNA and protein.

Another suitable method of polypeptide display is microbial surface display which involves the targeted location of expressed polypeptides to the exterior of a microbial cell, either gram-negative, gram-positive eubacteria or yeast. The polypeptides are fused to anchor domains that attach them to the cell surface. The anchor domains may have motifs dictating lipidation or covalent attachment to the cell wall, or they may be a fusion to an integral membrane protein within an exposed loop region.

The present application demonstrates that the polypeptides and polynucleotides of the invention are particularly effective when used in screening methods comprising cell-free expression systems. The use of the polypeptides and polynucleotides of the present invention in such expression systems greatly accelerates the screening process for polypeptides demonstrating high expression, high solubility and high affinity for a target polypeptide. The advantages result from the high solubility, stability and expression demonstrated by the polypeptides of the present invention, particularly under reducing conditions.

Thus, the polypeptides and polynucleotides of the present invention are particularly suitable for use in a screening method comprising any of the cell-free or in vitro expression systems described herein and others known in the art. For example, the polypeptides and polynucleotides of the present invention are particularly suitable for use in a screening method comprising ribosome display, mRNA display, cis-display (wherein an expressed polypeptide remains conjugated to its encoding polynucleotide sequence), or other such methods known in the art.

In addition, the present application demonstrates that the polypeptides and polynucleotides of the invention are particularly effective when used in screening methods based on protein display methods. For example, the polypeptides and polynucleotides of the invention are particularly effective when used in screening methods comprising phage display (e.g., lytic lambda phage, M13 filamentous phage, lysis defective phage, and others known in the art). In one example, the polypeptides and polynucleotides of the invention are surprisingly effective when used in a screening method comprising lambda phage.

In addition, the polypeptides and polynucleotides of the present invention can be used in a screening method based on a lysis defective phage (e.g., as described in International Patent Application No. PCT/AU2012/000761; the content of which is incorporated by reference in its entirety) in combination with the RED system described herein and in WO 2011/075761.

Kits

The necessary components for performing the methods of the invention may conveniently be provided in the form of a kit. As will be understood to a person skilled in the art, the various components in the kit may be supplied in individual containers or aliquots, or the solution components may be combined in different combinations and at different concentrations to achieve optimal performance of the methods of the invention. It is within the knowledge of the skilled addressee to determine which components of the kit may be combined such that the components are maintained in a stable form prior to use.

The kits of the invention will typically at a minimum contain a vector which comprises a site for inserting into the vector a polynucleotide encoding a polypeptide of the invention, and an open reading frame encoding a second polypeptide which associates with the first polypeptide to form a protein complex that can be retained inside or can attach to the cell wall of a permeabilised bacterial cell. Preferably, the kit also contains an agent for permeabilising a bacterial cell. In one embodiment, the kit further comprises bacterial cells, preferably Gram-negative bacterial cells. Other additional components may be included with the kit, or other components supplied by the end user, if required.

Uses

The polypeptides of the present invention are useful in a variety of applications, including research, diagnostic and therapeutic applications. Depending on the antigen to which the polypeptide binds it may be useful for delivering a compound to a cell, e.g., to kill the cell or prevent growth and/or for imaging and/or for in vitro assays. In one example, the polypeptide is useful for both imaging and delivering a cytotoxic agent to a cell, i.e., it is conjugated to a detectable label and a cytotoxic agent or a composition comprises a mixture of proteins some of which are conjugated to a cytotoxic agent and some of which are conjugated to a detectable label.

The polypeptides described herein can also act as inhibitors to inhibit (which can be reducing or preventing) (a) binding (e.g., of a ligand, an inhibitor) to a receptor, (b) a receptor signalling function, and/or (c) a stimulatory function. Polypeptides which act as inhibitors of receptor function can block ligand binding directly or indirectly (e.g., by causing a conformational change). The polypeptides described herein may be particularly suitable for applications involving a binding interaction that takes place within a host cell, given the stability and size of preferred polypeptides described herein.

Pharmaceutical Compositions and Methods of Treatment

The polypeptides of the present invention (syn. active ingredients) are useful for parenteral, topical, oral, or local administration, aerosol administration, or transdermal administration for prophylactic or for therapeutic treatment. The pharmaceutical compositions can be administered in a variety of unit dosage forms depending upon the method of administration. For example, unit dosage forms suitable for oral administration include powder, tablets, pills, capsules and lozenges or by parenteral administration. It is recognized that the pharmaceutical compositions of this invention, when administered orally, should be protected from digestion. This is typically accomplished either by complexing the proteins with a composition to render it resistant to acidic and enzymatic hydrolysis or by packaging the compound in an appropriately resistant carrier such as a liposome. Means of protecting proteins from digestion are known in the art.

Typically, a therapeutically effective amount of the polypeptide will be formulated into a composition for administration to a subject. The phrase "a therapeutically effective amount" refers to an amount sufficient to promote, induce, and/or enhance treatment or other therapeutic effect in a subject. As will be apparent, the concentration of proteins of the present invention in these formulations can vary widely, and will be selected primarily based on fluid volumes, viscosities, body weight and the like in accordance with the particular mode of administration selected and the patient's needs. Depending on the type and severity of the disease, a therapeutically effective amount may be about 1 µg/kg to 15 mg/kg (e.g. 0.1-20 mg/kg) of molecule, whether, for example, by one or more separate administrations, or by continuous infusion. A typical daily dosage might range from about 1 µg/kg to 100 mg/kg or more. An exemplary dosage of the protein to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of the protein. Other dosage regimens may be useful. The progress of this therapy is easily monitored by conventional techniques and assays.

Alternatively, the polypeptide of the invention is formulated at a concentrated does that is diluted to a therapeutically effective dose prior to administration to a subject.

The pharmaceutical compositions of this invention are particularly useful for parenteral administration, e.g., formulated for injection via the intravenous, intramuscular, sub-cutaneous, transdermal, or other such routes, including peristaltic administration and direct instillation into a tumour or disease site (intracavity administration). The compositions for administration will commonly comprise a solution of the proteins of the present invention dissolved in a pharmaceutically acceptable carrier, preferably an aqueous carrier. A variety of aqueous carriers can be used, e.g., buffered saline and the like. Other exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

Techniques for preparing pharmaceutical compositions are generally known in the art as exemplified by Remington's Pharmaceutical Sciences, 16th Ed. Mack Publishing Company, 1980.

WO2002/080967 describes compositions and methods for administering aerosolized compositions comprising proteins for the treatment of, e.g., asthma, which are also suitable for administration of protein of the present invention.

Suitable dosages of compounds of the present invention will vary depending on the specific protein, the condition to be diagnosed/treated/prevented and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment/prophylaxis, data from cell culture assays or animal studies are used, wherein a suitable dose is within a range of circulating concentrations that include the ED50 of the active compound with little or no toxicity. The dosage may vary within this range depending upon the dosage form employed and the route of administration utilized. A therapeutically/prophylactically effective dose can be estimated initially from cell culture assays. A dose may be formulated in animal models to achieve a circulating plasma concentration range that includes the IC50 (i.e., the concentration of the compound which achieves a half-maximal inhibition of symptoms) as determined in cell culture. Such information can be used to more accurately determine useful doses in humans. Levels in plasma maybe measured, for example, by high performance liquid chromatography.

A protein of the invention may be combined in a pharmaceutical combination formulation, or dosing regimen as combination therapy, with a second compound. The second compound of the pharmaceutical combination formulation or dosing regimen preferably has complementary activities to the protein of the combination such that they do not adversely affect each other.

The second compound may be a chemotherapeutic agent, cytotoxic agent, cytokine, growth inhibitory agent, antihormonal agent, and/or cardioprotectant. Such molecules are suitably present in combination in amounts that are effective for the purpose intended. A pharmaceutical composition containing a protein of the invention may also have a therapeutically effective amount of a chemotherapeutic agent such as a tubulin-forming inhibitor, a topoisomerase inhibitor, or a DNA binder.

Pharmaceutical "slow release" capsules or compositions may also be used. Slow release formulations are generally designed to give a constant drug level over an extended period and may be used to deliver compounds of the present invention.

The present invention also provides a method of treating or preventing a condition in a subject, the method comprising administering a therapeutically effective amount of a protein of the invention to a subject in need thereof.

As used herein, the terms "preventing", "prevent" or "prevention" in the context of preventing a condition include administering an amount of a protein described herein sufficient to stop or hinder the development of at least one symptom of a specified disease or condition.

As used herein, the terms "treating", "treat" or "treatment" include administering a therapeutically effective amount of an inhibitor(s) and/or agent(s) described herein sufficient to reduce or eliminate at least one symptom of a specified disease or condition. As used herein, the term "subject" shall be taken to mean any animal including humans, preferably a mammal. Exemplary subjects include but are not limited to humans, primates, livestock (e.g. sheep, cows, horses, donkeys, pigs), companion animals (e.g. dogs, cats), laboratory test animals (e.g. mice, rabbits, rats, guinea pigs, hamsters), captive wild animals (e.g. fox, deer). Preferably the mammal is a human or primate. More preferably the mammal is a human.

As used herein, a "condition" is a disruption of or interference with normal function, and is not to be limited to any specific condition, and will include diseases or disorders. In an example, the condition is a cancer or an immunopathological disorder.

Exemplary cancers include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Immunopathology is the study of disease having an immunological cause and immunologic disease is any condition caused by the reactions of immunoglobulins to antigens. Thus, an "immunopathological disorder" can be defined as a disorder arising from reaction of a subject's immune system to antigens. Immunopathological disorders include autoimmune diseases and hypersensitivity responses (e.g. Type I: anaphylaxis, hives, food allergies, asthma; Type II: autoimmune haemolytic anaemia, blood transfusion reactions; Type III: serum sickness, necrotizing vasculitis, glomerulonephritis, rheumatoid arthritis, lupus; Type IV: contact dermatitis, graft rejection). Autoimmune diseases include rheumatologic disorders (such as, for example, rheumatoid arthritis, Sjogren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjogren's syndrome, Graves' disease, IDDM, pernicious anemia, thyroiditis, and glomerulonephritis.

In another embodiment, the disorder is an inflammatory disease. Inflammation is a protective response of body tissues to irritation or injury- and can be acute or chronic. Thus, inflammatory disorders include diseases involving neutrophils, monocytes, mast cells, basophils, eosinophils, macrophages where cytokine release, histamine release, oxidative burst, phagocytosis, release of other granule enzymes and chemotaxis occur. Hypersensitivity responses (defined above under immunopathological disorders) can also be regarded as inflammatory diseases (acute or chronic) since they often involve complement activation and recruitment/infiltration of various leukocytes such as neutrophils, mast cells, basophils, etc.

The compositions of the present invention will be administered in a manner compatible with the dosage formulation and in such amount as is therapeutically/prophylactically effective. Formulations are easily administered in a variety of manners, e.g., by ingestion or injection or inhalation.

Other therapeutic regimens may be combined with the administration of a polypeptide of the invention. The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

The invention will now be further described with reference to the following, non-limiting examples.

EXAMPLES

Example 1

Cloning of Human VL Sub-libraries into a IGHV3-23 Display Vector

To screen for human light chain partners for IGHV3-23 that would be well expressed and soluble in the E. coli cytoplasm, the inventors cloned all 10λ and 5κ functional light chain families as scFv fusions to IGHV3-23. The scFv library was cloned into an expression construct that was arabinose-inducible and was further fused to downstream domains that conferred cell-wall binding (peptidoglycan (PG) binding domain), an expression reporter domain (SNAP; New England Biolabs), and a DNA binding domain (DBP), in that order. These downstream domains enable retention of the scFv moiety when the outer and inner bacterial host cell membranes are permeabilised by detergent or organic solvents by anchoring the fusion protein to both DNA and the cell wall.

The λ and κ light chain families were amplified from cDNA prepared from human peripheral blood mononuclear cells (PBMCs). The κ and λ light chain subfamilies were amplified in 7 and 11 PCR reactions respectively. Each sublibrary was first screened separately to broadly characterise the percentage of the library that contained apparently soluble members. Sublibraries that contained an appreciable percentage of soluble members (>1%) were then screened as individual clones.

The oligonucleotide primers were based on the sequences described by Hust and Dubel (2010) with modifications to the ends for cloning via BsmBI. Further changes were made to the reverse primer sequences that were originally designed against the C1 constant domain of the light chain. This was considered to include unnecessary sequence, and degenerate primers were designed against the J regions for the light chain. The oligonucleotide sequences for amplification of the light chain regions are listed in Table 2.

TABLE 2

Oligonucleotide sequences for amplification of the light chain regions.

| | Oligonucleotide sequence |
|---|---|
| κ first round | |
| HVK1 F1 | GAC ATC CAG ATG ACC CAG TCT CC (SEQ ID NO: 31) |
| HVK1 F2 | GMC ATC CRG WTG ACC CAG TCT CC (SEQ ID NO: 32) |
| HVK2 F | GAT RTT GTG ATG ACY CAG WCT CC (SEQ ID NO: 33) |
| HVK3 F | GAA ATW GTG WTG ACR CAG TCT CC (SEQ ID NO: 34) |
| HVK4 F | GAC ATC GTG ATG ACC CAG TCT CC (SEQ ID NO: 35) |
| HVK5 F | GAA ACG ACA CTC ACG CAG TCT CC (SEQ ID NO: 36) |
| HVK6 F | GAW RTT GTG MTG ACW CAG TCT CC (SEQ ID NO: 37) |
| HVKCL R | ACA CTC TCC CCT GTT GAA GCT CTT (SEQ ID NO: 38) |
| λ first round | |
| HVL1 F1 | CAG TCT GTG CTG ACT CAG CCA CC (SEQ ID NO: 39) |
| HVL1 F2 | CAG TCT GTG YTG ACG CAG CCG CC (SEQ ID NO: 40) |
| HVL2 F | CAG TCT GCC CTG ACT CAG CCT (SEQ ID NO: 41) |
| HVL3 F1 | TCC TAT GWG CTG ACW CAG CCA CC (SEQ ID NO: 42) |
| HVL3 F2 | TCT TCT GAG CTG ACT CAG GAC CC (SEQ ID NO: 43) |

TABLE 2 -continued

Oligonucleotide sequences for amplification of the light chain regions.

| | Oligonucleotide sequence |
|---|---|
| HVL4 F1 | CTG CCT GTG CTG ACT CAG CCC (SEQ ID NO: 44) |
| HVL4 F2 | CAG CYT GTG CTG ACT CAA TCR YC (SEQ ID NO: 45) |
| HVL5 F | CAG SCT GTG CTG ACT CAG CC (SEQ ID NO: 46) |
| HVL6 F | AAT TTT ATG CTG ACT CAG CCC CA (SEQ ID NO: 47) |
| HVL7/8 F | CAG RCT GTG GTG ACY CAG GAG CC (SEQ ID NO: 48) |
| HVL9/10 F | CAG SCW GKG CTG ACT CAG CCA CC (SEQ ID NO: 49) |
| 01115 HVLCL R | TGA ACA TTC TGT AGG GGC CAC TG (SEQ ID NO: 50) |
| 01116 HVLCL R2 | TGA ACA TTC CGT AGG GGC AAC TG (SEQ ID NO: 51) |

κ second round

| | |
|---|---|
| HVK1 2F1 | ATCTAGAATG GGA GAC GGT GAC ATC CAG ATG ACC CAG TCT CC (SEQ ID NO: 52) |
| HVK1 2F2 | ATCTAGAATG GGA GAC GGT GMC ATC CRG WTG ACC CAG TCT CC (SEQ ID NO: 53) |
| HVK2 2F | ATCTAGAATG GGA GAC GGT GAT RTT GTG ATG ACY CAG WCT CC (SEQ ID NO: 54) |
| HVK3 2F | ATCTAGAATG GGA GAC GGT GAA ATW GTG WTG ACR CAG TCT CC (SEQ ID NO: 55) |
| HVK4 2F | ATCTAGAATG GGA GAC GGT GAC ATC GTG ATG ACC CAG TCT CC (SEQ ID NO: 56) |
| HVK5 2F | ATCTAGAATG GGA GAC GGT GAA ACG ACA CTC ACG CAG TCT CC (SEQ ID NO: 57) |
| HVK6 2F | ATCTAGAATG GGA GAC GGT GAW RTT GTG MTG ACW CAG TCT CC (SEQ ID NO: 58) |
| HVKCL 2R | GATCAG GGT CTG AGA CGA TTT RAT HTC CAS YYK KGT CCC HBS GCC RAA VGT (SEQ ID NO: 59) |

λ second round

| | |
|---|---|
| HVL1 2F1 | ATCTAGAATG GGA GAC GGT CAG TCT GTG CTG ACT CAG CCA CC (SEQ ID NO: 60) |
| HVL1 2F2 | ATCTAGAATG GGA GAC GGT CAG TCT GTG YTG ACG CAG CCG CC (SEQ ID NO: 61) |
| HVL2 2F | ATCTAGAATG GGA GAC GGT CAG TCT GCC CTG ACT CAG CCT (SEQ ID NO: 62) |
| HVL3 2F1 | ATCTAGAATG GGA GAC GGT TCC TAT GWG CTG ACW CAG CCA CC (SEQ ID NO: 63) |
| HVL3 2F2 | ATCTAGAATG GGA GAC GGT TCT TCT GAG CTG ACT CAG GAC CC (SEQ ID NO: 64) |
| HVL4 2F1 | ATCTAGAATG GGA GAC GGT CTG CCT GTG CTG ACT CAG CCC (SEQ ID NO: 65) |
| HVL4 2F2 | ATCTAGAATG GGA GAC GGT CAG CYT GTG CTG ACT CAA TCR YC (SEQ ID NO: 66) |
| HVL5 2F | ATCTAGAATG GGA GAC GGT CAG SCT GTG CTG ACT CAG CC (SEQ ID NO: 67) |
| HVL6 2F | ATCTAGAATG GGA GAC GGT AAT TTT ATG CTG ACT CAG CCC CA (SEQ ID NO: 68) |
| HVL7/8 2F | ATCTAGAATG GGA GAC GGT CAG RCT GTG GTG ACY CAG GAG CC (SEQ ID NO: 69) |
| HVL9/10 2F | ATCTAGAATG GGA GAC GGT CAG SCW GKG CTG ACT CAG CCA CC (SEQ ID NO: 70) |
| HVLCL 2R | GATCAG GGT CTG AGA CGA RRY GRT SAS CTB SGT BCC HBY DCC RAA BAC (SEQ ID NO: 71) |

The VL genes for λ and κ light chain sublibraries were amplified in two rounds of PCR using Vent DNA polymerase (New England Biolabs). Each sublibrary was cloned separately into the RED display vector using BsmBI (New England Biolabs). Each library was estimated to produce approximately 20-40,000 colonies.

Example 2

Screening of Human scFv Fusions Using Retained Encapsulated Display (RED)

As an initial screen of solubility each library plate was scraped and suspended in 10 mL of LB/glycerol (10%). A fraction of the suspension (~50 uL) was grown in 1 mL of LB media (10 g tryptone, 5 g yeast extract, 10 g NaCl per litre) at 37° C. for 1 hour and then induced with 0.2% arabinose and grown for a further 2 hours at 25° C. At this point the cells were permeabilised by resuspension of the bacterial pellet in 0.5% n-Octyl-β-D-Thioglucoside (8TGP) in LB media for 10 minutes at 25° C. The permeabilised cells were washed once by pelleting and resuspension in LB media before the induced scFv fusion protein was labeled by the addition of SNAP-surface 488 reagent (S9124S; New England Biolabs) and incubation at 25° C. for 20 minutes. The labeled cells were then washed again by pelleting and resuspended in PBS before a sample was mounted for viewing by fluorescence microscopy.

Microscopic examination showed that although all libraries had some cells within each field of view that appeared to be well expressed and soluble, only the sublibraries representing the Vλ1, Vλ3 and Vλ6 clades were found to have >1% of cells that had a soluble morphology. Thus, the sublibraries for all except for the Vλ1, Vλ3 and Vλ6 were not considered to have a high enough frequency of soluble clones and were not screened further.

Sublibraries Vλ1, Vλ3 and Vλ6 were plated at dilutions that produced single clones and screened for solubility individually. Thus, the Vλ1, Vλ3 and Vλ6 sublibraries were plated at dilutions allowing clean picks of single colonies, which were then induced for expression, and prepared for microscopy, as described above.

Figure 1:
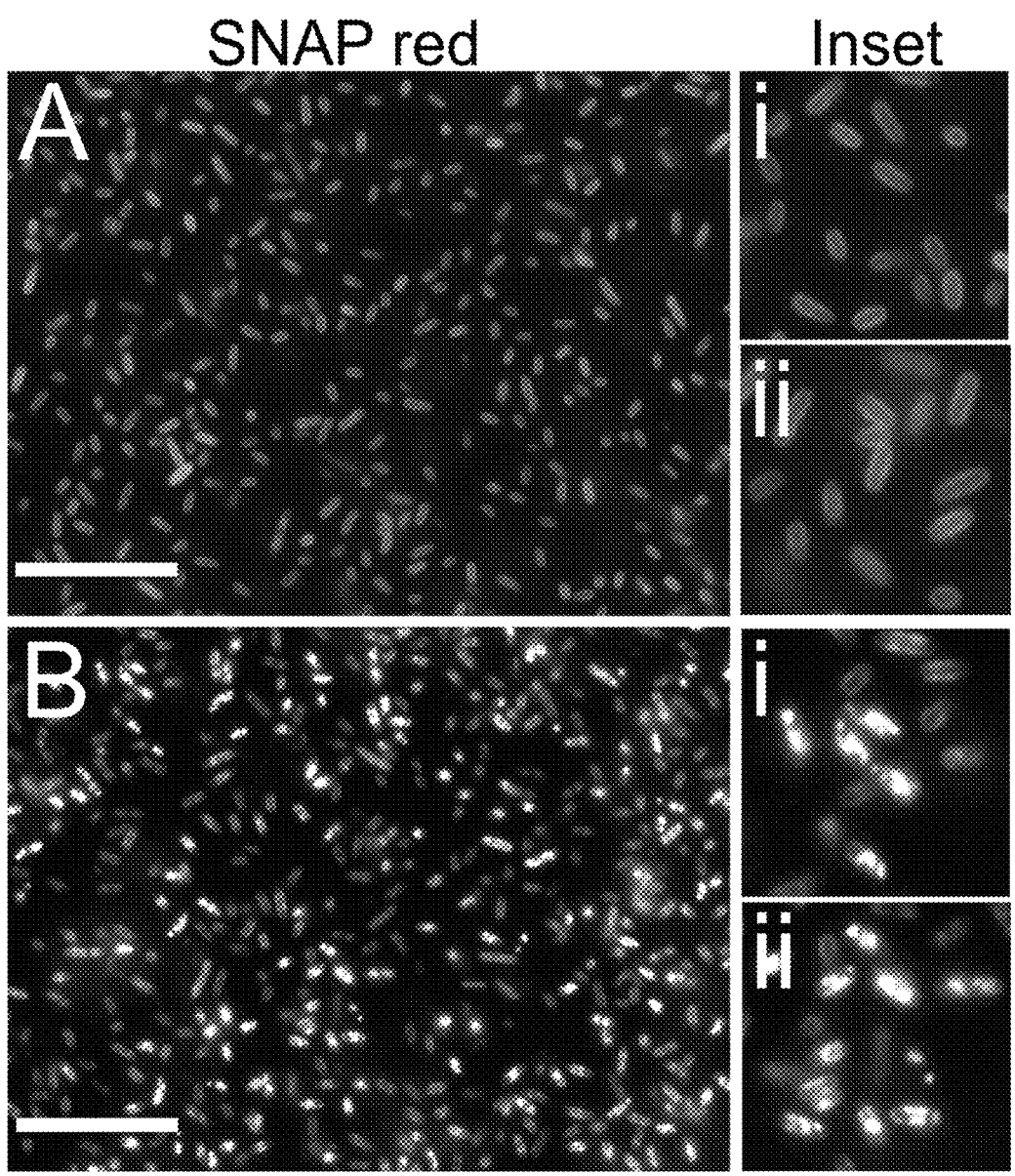

FIG. 1 demonstrates the typical appearance of a well-expressed, soluble scFv clone (1A, and inset), along with a well-expressed, but insoluble scFv clone (1B, and inset). The cells are labelled with SNAP fluorophore following permeabilisation as described above. The distinctive clumping of an insoluble clone contrasts with the more diffuse and peripheral localisation of the soluble clone.

scFv clones that demonstrated soluble expression were then grown overnight at 37° C. under 100 μg/mL ampicillin selection, a plasmid preparation performed using standard methods (Sambrook et al., Molecular Cloning: A Laboratory Manual, 3$^{rd}$ edn, Cold Spring Harbour Laboratory Press (2001) and the DNA was sequenced with a primer in the upstream promoter region of the expression construct. Sequence files were then analysed against the human genomic GenBank database using the NCBI BLAST algorithm.

Figure 2:
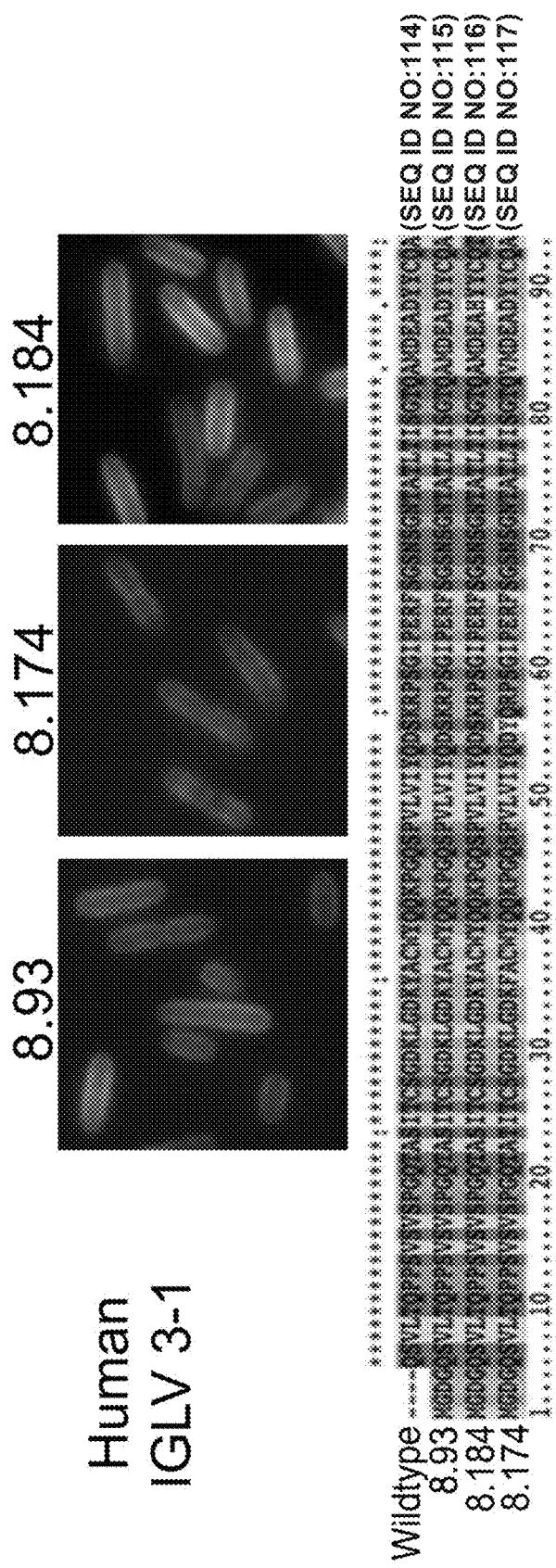
Figure 2A:
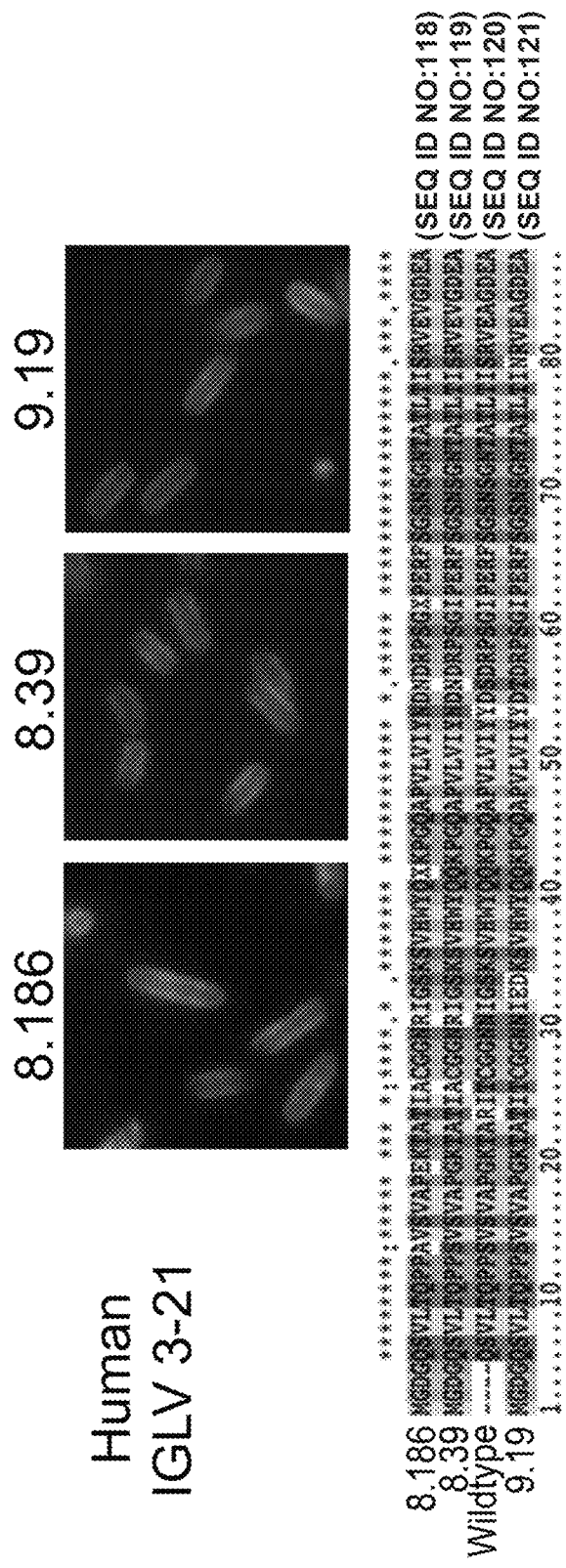
Figure 2B:
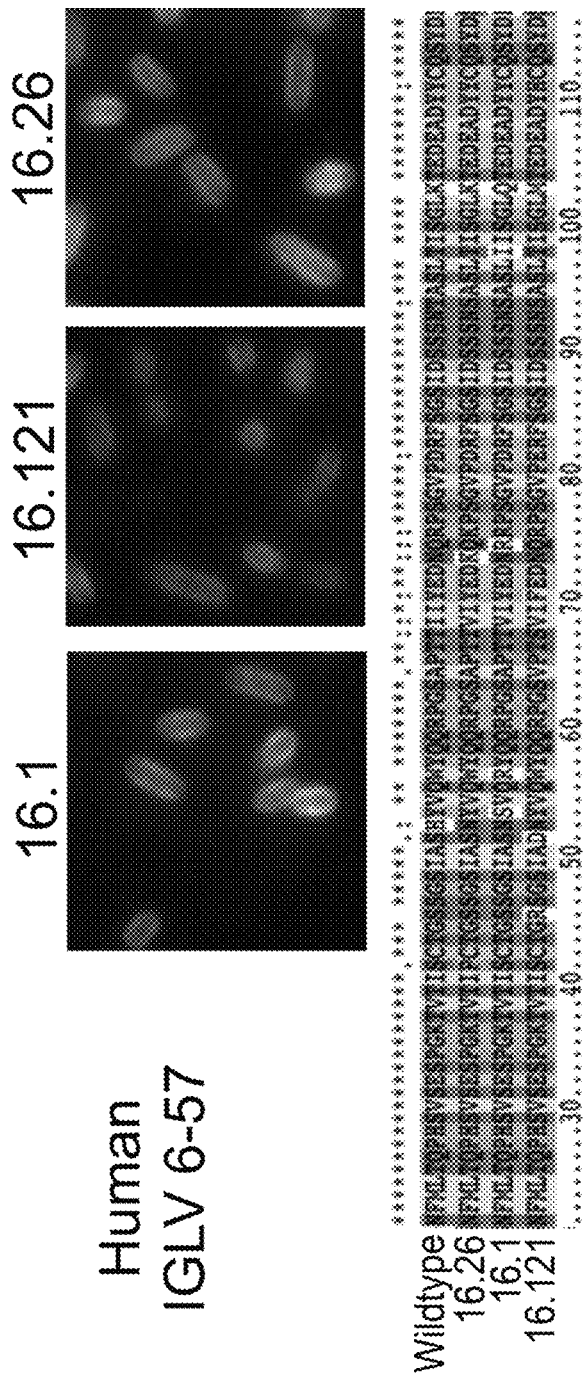

FIG. 2 represents a multiple alignment of selected soluble clones that have high similarity, or total identity, to the VL genes IGLV3-1, IGLV3-21 and IGLV6-57. The multiple alignment was prepared using CLUSTAL X. The images of soluble clone (listed by isolate number) above the alignment correspond to the aligned sequences below.

Clones were checked by isolation and sequencing.

The screen of 779 sublibrary members for soluble individuals yielded 11 clones of IGLV1-40 (SEQ ID NO: 18); 2 clones of IGLV1-44 (SEQ ID NO: 21); 3 clones of IGLV1-47 (SEQ ID NO: 24); 3 clones of IGLV1-51 (SEQ ID NO: 15); 25 clones of IGLV3-1 (SEQ ID NO: 6); 2 clones of IGLV3-19 (SEQ ID NO: 27); 4 clones of IGLV3-21 (SEQ ID NO: 9); 18 clones of IGLV6-57 (SEQ ID NO: 12). Analysis of the sequences of soluble scFv clones showed that there were apparently naïve sequences for members IGLV1-40, IGLV1-51, IGLV3-1, and IGLV3-19 that had not been affinity selected or matured in vivo during B-cell presentation. Furthermore, certain IGLV6-57 clones had high solubility with only 1 (2 clones) or 2 (1 clone) amino acid changes from the translation of the germline sequence, for a total identity of 99% and 98%, respectively.

Therefore, in contrast to the results of prior screening for soluble and stable human antibodies in the cytoplasm of yeast by Tse et al., (2002) who found soluble antibodies that comprised a $V_H3$ domain were entirely paired with VLκ 1 and 4 partners, the inventors found that VLκ subfamilies had poor apparent solubility as a class, with >99% of the VLκ sublibraries clones specifically paired with the IGHV3-23 domain either poorly expressed in E. coli or showing signs of misfolding. Tissot et al. (WO 03/097697) also conducted a Y2H screen for soluble human scFvs, and reported that their soluble scFvs were sequences most closely related to members of the VH1a, VH1b or VH3, clades combined with sequences most closely related to members of the VLκ1 or VLλ1 or VLλ3 clades. However, their optimal configuration was VLλ3 paired with VH1b.

However, as both Tse et al. (2002) and Tissot (WO 03/097697) were applying a functional screen (i.e., binding of the antibody to an antigen target in vivo) as a further requirement for solubility their output antibodies that have a positive Y2H signal required both 1) solubility; and, 2) target binding, and therefore by necessity, were substantially mutated from their germline sequence.

The majority of the VL members isolated in the screen for soluble fusions to the IGHV3-23 domain were IGLV3-1, also known as DPL23. Although some clones had numerous mutations a significant number were identical to the IGLV3-1 germline V sequence (SEQ ID NO: 4), indicating that the germline sequence is inherently stable and soluble in the cytoplasm when partnered with IGHV3-23.

IGLV3-1 has a moderately high expression in the human immune system, representing 15% of the λ light chains (Knappik et al., 2000), but is not the most abundantly expressed λ member (DPL11). In the published literature it is uncharacterized, lacking any specific citations, and no reported structures with high identity. Although artificial scFv scaffold libraries using IGHV3-23 had been made before, the VL partners were chosen mainly on the basis of their relative expression levels in vivo, i.e. highly expressed DPK22 (Pini et al., 1998; and Ge et al., 2010), DPL3 (aka. IGLV1-47) (Kobayashi et al, 1997; Soderlind et al, 2000) and DPL16 (aka. IGLV3-19) (Viti et al., 2000).

The only published report of a global analysis of the thermostability of the human variable domain repertoire was performed on the Morphosys HuCAL™ library by Ewert et al. (2003). In their article titled "Biophysical Properties of Human Antibody Variable Domains", the authors examined both the stability of individual domains, as well as the stability of domain pairings ($V_L::V_H$), when expressed in the E. coli periplasm.

The VH3 consensus, to which IGHV3-23 is related, was declared the most stable for thermodynamic stability and solubility of the heavy chain variable regions, whilst the Vκ3 consensus was the most stable light chain variable region.

The $V_H::V_L$ combinations that produced the most stable pairings were those formed between H3::κ3, H1b::κ3, H5::κ3 and H3::κ1. It is noteworthy that none of the most stable pairings included the $V_L3$ family. Furthermore, constructing our scFv library using a $V_H3$ partner (IGHV3-23) was not, in of itself, sufficient to confer stability on the fusion protein when expressed in the E. coli cytoplasm as the vast majority of clones in most sublibraries were either misfolded or poorly expressed.

In summary, on the basis of the prior art, the combination of use of domains IGHV3-23 and IGLV3-1 as a scFv fusion could not be predicted to possess enhanced stability and solubility when expressed in a reducing environment, such as the E. coli cytoplasm.

Example 3

Thermostability Testing of scFv Clones

Following the initial screen of the $V_L$ sublibraries with induction and expression at 25° C., the scFv clones were subjected to a further screen to grade the clones and families for thermostability.

Each clone was induced at temperatures of 26° C., 28° C., 30° C., 32° C., 34° C., 36° C. and 38° C. for 90 minutes before permeabilising and labelling with SNAP, as described for Example 2. Clones were scored for solubility using fluorescence microscopy, as described for Example 2.

Figure 3:
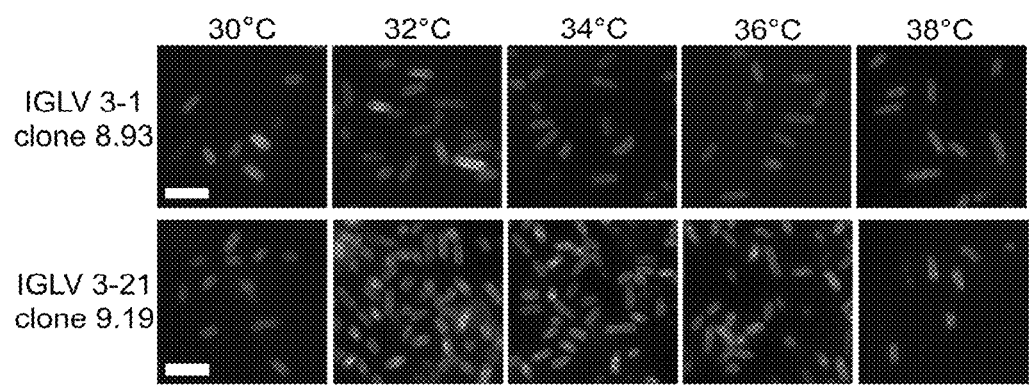

FIG. 3 demonstrates the behaviour of two clones, one IGLV3-1 and one IGLV3-21, with expression at increasing temperatures. The scFv fusion proteins remain soluble until at least 36° C. for the IGLV3-1 clone, although the IGLV3-21 clone shows signs of misfolding between 32 and 34° C.

Figure 4:
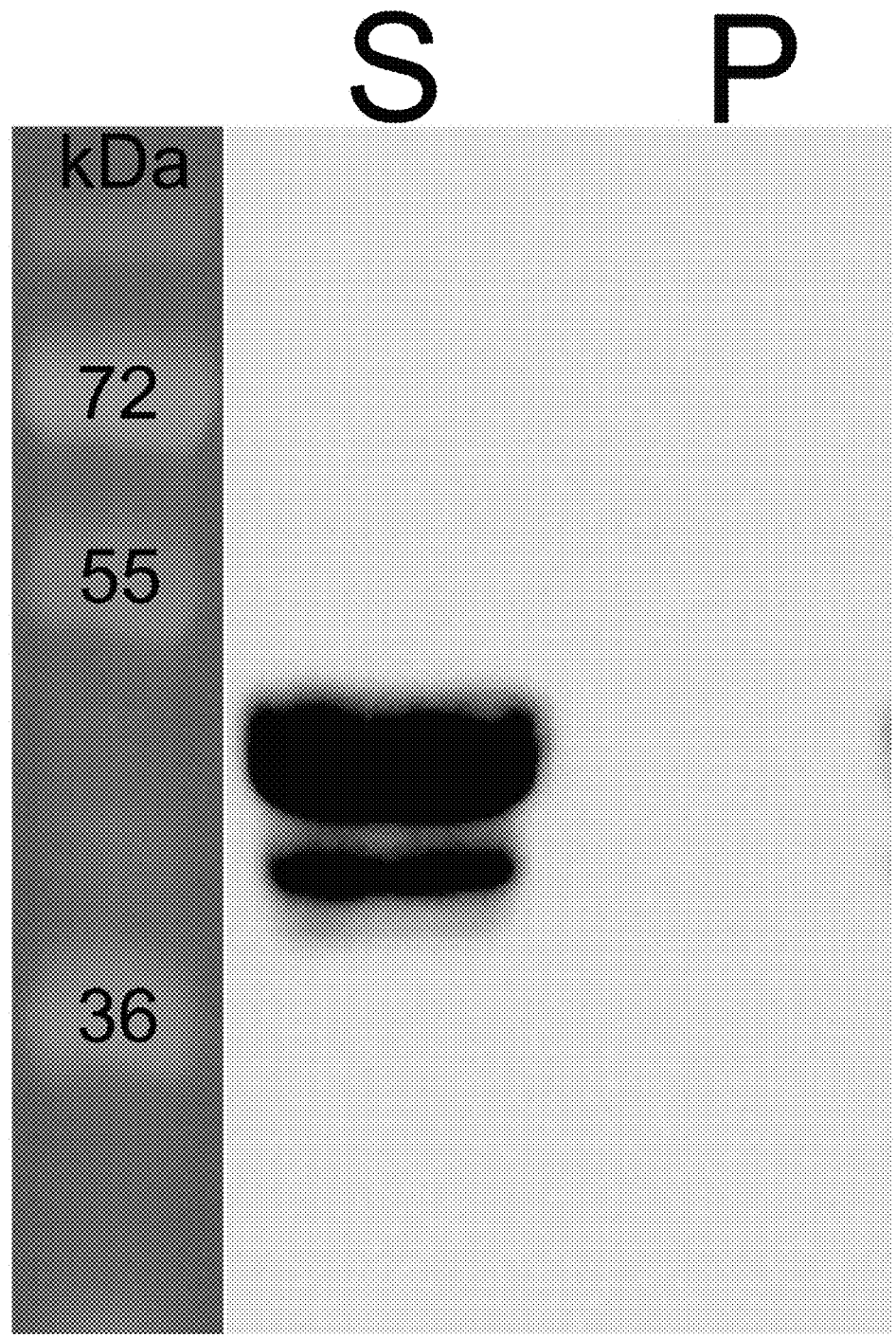

This expression temperature gradient showed that scFv clones related, or identical to, IGLV3-1 and IGLV6-57 were judged as having the best solubility as a class, although individual clones of the other λ genes also demonstrated varying degrees of solubility. FIG. 4 demonstrates the solubility of representative clones of each species of $V_L$ domain isolated from the screen.

That the apparent solubility of the scFvs by microscopy was not artifactual was confirmed by subcloning the scFv fragment, along with the downstream 127 domain from human Titin, into an expression construct with a C-terminal FLAG epitope. The scFv::127::FLAG fusion protein was induced with arabinose at temperatures ranging from 26° C. to 38° C. and the *E. coli* cells lysed using ultrasonication. Soluble proteins were separated from insoluble debris and protein aggregates by centrifugation (14K 1 min).

FIG. 4 demonstrates the excellent solubility of an IGLV3-1 clone when expressed in the *E. coli* cytosol at 25° C. The scFv::127::FLAG fusion protein is entirely in the soluble fraction. It does demonstrate some N-terminal cleavage of a minor fraction of the total protein, although this was eliminated when the protein was extracted under denaturing conditions suggesting that it was caused by the interaction of periplasmic proteases that were released with the permeabilisation by the 8TGP detergent.

Thus, due to the high frequency of recovery of IGLV3-1 from the solubility screen in *E. coli*, it was further characterized for the necessary traits for an exemplary scaffold of a soluble scFv library-stability in the cytoplasm at temperatures close to 37° C., and tolerance for a diversified CDR3 loop. The IGLV3-1 was tested for thermostability in the *E. coli* cytoplasm at a temperature range from 28° C. to 38° C. It was found to be highly soluble to 36° C. when coupled to the light chain J1 and J2 regions, as well as J regions that were formed using the degenerate oligonucleotides as primers during PCR of the PBMC cDNA. At 36° C. and above, it demonstrated a degree of misfolding. This was confirmed by both immunofluorescence and by Western blotting of FLAG-tagged scFv.

Example 4

IGLV3-1 J Domain Exchange

The degenerate oligonucleotide sequences listed in Table 2 that were used to amplify the VL domains had to prime the 7 different λ J regions in the human genome (Table 3). As such, the clones isolated from the screen had hybrid λ J regions that represented a non-canonical sequence that may have decreased their folding stability.

TABLE 3

| Human λ J regions | |
|---|---|
| Lambda J region | Amino acid sequence |
| J1 | VFGTGTKVTVs (SEQ ID NO: 72) |
| J2 | VFGGGTKLTVs (SEQ ID NO: 73) |
| J3 | VFGGGTKLTVs (SEQ ID NO: 74) |
| J4 | VFGGGTQLIIs (SEQ ID NO: 75) |
| J5 | VFGEGTELTVs (SEQ ID NO: 76) |
| J6 | VFGSGTKVTVs (SEQ ID NO: 77) |
| J7 | VFGGGTQLTAs (SEQ ID NO: 78) |

TABLE 3-continued

Comparison of the J regions of the most stable of the IGLV3-1 clones that had the germline sequence of the framework regions showed the highest similarity to J regions 1 and 2/3. Therefore, the hybrid J region ("VFGTGTKLIIS" (SEQ ID NO: 79)) was replaced with the germline λ J1 or J2/3 sequences (Table 3) to test whether the thermostability of the IGLV3-1 scaffold would be further improved. The variants were tested at temperatures between 30° C., 32° C., 34° C., 36° C. and 38° C. Subjectively, it was felt that λ J1 gave slightly better folding and solubility than J2/3 or the original hybrid J region of the clone tested.

Figure 5:
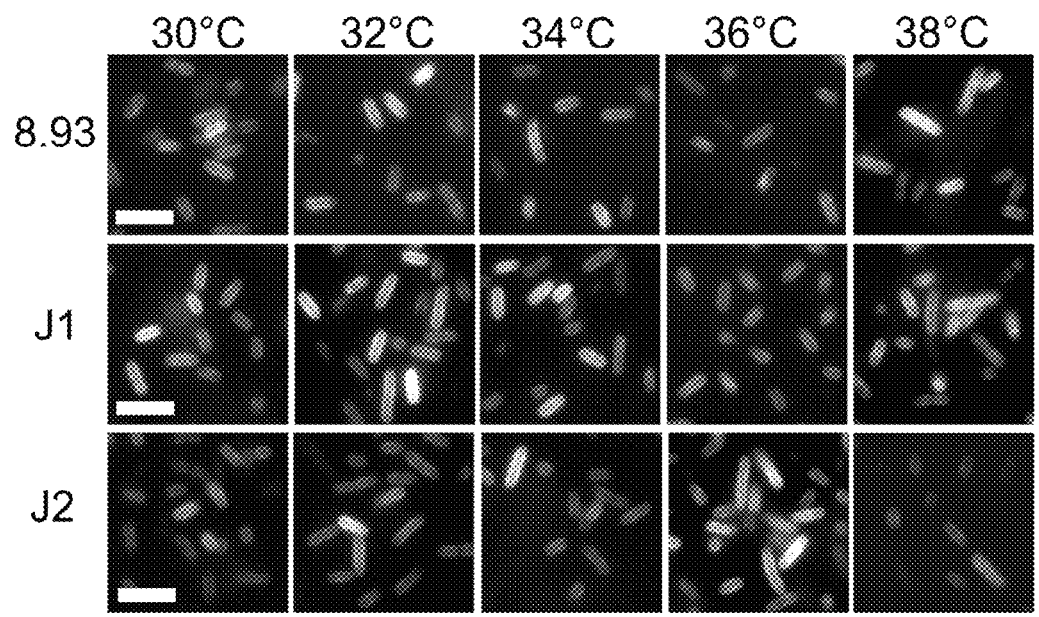

FIG. 5 demonstrates the thermostability behaviour of the original clone (#8.93) with replacement of the λ J region for J1 or J2.

Example 5

Tolerance of IGLV3-1 and IGHV3-23 to CDR3 Diversification

For an scFv to be useful as a framework for an affinity library, it needs to be tolerant of substitutions in the CDR3 region. This is especially true for scFvs that are expressed in a reducing environment, such as the *E. coli* cytosol, where the stabilising intra-domain disulphide bonds are absent.

To test the stability of the preferred scFv scaffold, IGLV3-1::IGHV3-23, the CDR3 region of each domain was diversified separately. Thus, both the IGLV3-1 and IGHV3-23 genes were tested for their tolerance to CDR3 diversification. FIG. 2 shows the region around CDR3 for both sequences, as well as the proposed diversification. The IGLV3-1 CDR3 of 2 amino acids was replaced with a "-NNNGGNNN-" (SEQ ID NO: 29) region (where 'N' is an amino acid other than Trp, Gln, Lys, Glu, Met). Similarly, the IGHV3-23 CDR3 of 12 amino acids was replaced with a "-NNNGNNN-" (SEQ ID NO: 29) region. Each domain was tested separately for solubility and expression as a pooled library of clones. In addition, randomly picked individual clones were also tested and sequenced to confirm the expected diversity.

The IGLV3-1 CDR3 was replaced from residue 91 onwards by modifying the IGLV3-1 domain by PCR using the (reverse) oligonucleotide sequence:

```
                                       (SEQ ID NO: 80)
GATCAGGGTCTGAGACGAGACCGTCACTTTCGTACCGGTGCCGAACACC

ACAGTANNANNANNTCCGCCANNANNANNGTCCCACGCCTGACAGTAAT

AGTCAGC
```

The (rev/comp) translation of this sequence gives (where "N" is any amino acid other than Trp, Gln, Lys, Glu, Met):

```
                                     (SEQ ID NO: 81)
...ADYYCQAWD(91) NNNGGNNN TVVFGTGTKVTVSS
```

The IGLV3-1 CDR3 replacement was resoundingly successful. The appearance of the population with protein induction at 30° C. was very soluble clones with good expression. 40 clones were analysed individually and 36 were ranked as excellent for solubility and expression. The 4 failed clones, and 16 others with good solubility and expression, were sequenced across the VL domain. It was confirmed that the four failed clones failed due to frameshifts in the long oligonucleotide primer used to amplify up the gene. All other clones examined that had the correct reading frame had a random mixture of amino acids, and demonstrate that the germline IGLV3-1 framework is very tolerant of CDR3 diversification.

Thus, for IGLV3-1, the solubility of a diversified CDR3 library when expressed at 30° C. in the E. coli cytoplasm was surprisingly high. Approximately 90% of clones were soluble with high expression. The 10% clones with low or no expression, or were misfolded, were sequenced and shown to be frameshifted, predominantly in the region of the reverse primer that was by necessity ~100 bases long. Base deletions are a common error when building synthetic libraries using long oligonucleotides and other groups have developed pre-screening strategies based on antibiotic selection to enrich for in-frame alleles (e.g. Ge et al., 2010).

The CDR3 region of the VH domain, IGHV3-23 was replaced using a reverse oligonucleotide similarly to the method described above from residue 98 onwards by modifying the IGHV3-23 domain by PCR using the (reverse) oligonucleotide sequence:

```
                                          (SEQ ID NO: 82)
GATCAGGGTCTGAGACCCGCTGCTCACGGTAACCATGGTACCTTGACCC

CAAATATCAAACGCANNANNANNGCCANNANNANNTTTCGCACAGTAGT

AAACAGC
```

The (rev/comp) translation of this sequence gives (where "N" is any amino acid other than Trp, Gln, Lys, Glu, Met):

```
                                     (SEQ ID NO: 83)
VYYCAK(98) NNNGNNN AFDIWGQGTMVT
```

The IGHV3-23 proved just as robust to CDR3 diversification as the IGLV3-1 domain, with 80% of tested clones showing soluble, high expression, and the 20% that were poorly expressed were explicable upon sequencing due to conservative mismatches in the framework, or more commonly, single base pair deletions in the region of the long oligonucleotide primer, thereby changing the frame of protein translation.

Thus, for IGHV3-23, the solubility of a diversified CDR3 library when expressed at 30° C. in the E. coli cytoplasm was, again, surprisingly high (~80%). Again, frameshifting of the fusion protein was responsible for many negatives. The shortening of the CDR3 loop from 12 to 7 amino acids also improved the solubility of this library compared to the parental clone.

Figure 6:
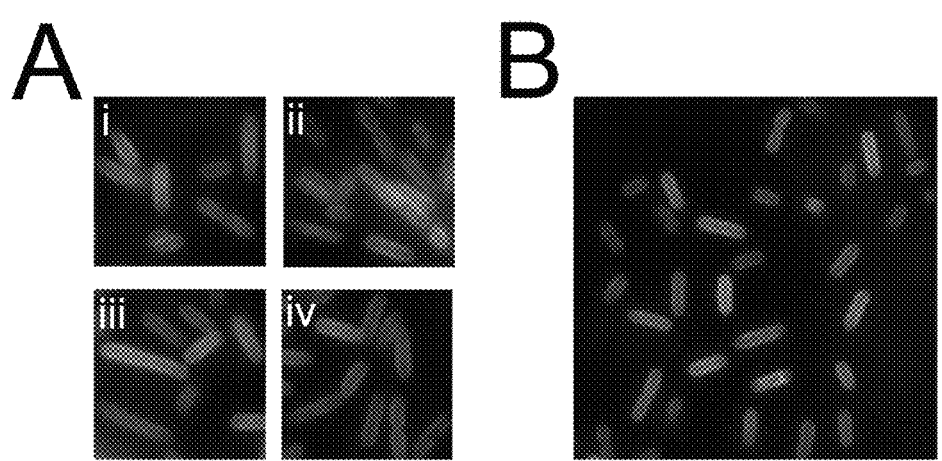

FIG. 6A demonstrates the solubility and high expression of 4 independent clones with the IGLV3-1 CDR3 diversified. FIG. 6B demonstrates a sample of the entire population of clones with the IGHV3-23 CDR3 diversified. Therefore, in summary, the IGLV3-1::IGHV3-23 framework is an exemplary scaffold for constructing an affinity library, being identical to the human germline sequence and remaining robustly soluble with replacement of the CDR3 loops with diversified sequence. Furthermore, combining the scaffold with the RED protein display method in the E. coli cytoplasm enables concurrent screening for both affinity protein stability, expression and binding to the target molecule. The scaffold is highly stable and soluble in the reducing environment of the E. coli cytoplasm where it lacks the stabilizing intra-domain disulphide bonds that are an essential requirement for folding and stability of almost all other scFv proteins. This scaffold will enable low-cost production of affinity reagents in the E. coli cytoplasm for research, therapeutic or diagnostic uses, as well as the use of such reagents in the cytoplasm of mammalian cells for targeting endogenous proteins.

Example 6

Construction of a Diversified IGLV3-1::IGHV3-23 scFv Library

The IGLV3-1::IGHV3-23 scaffold was diversified using the strategy described for Example 5 to introduce the amino acid sequences 'NNNGGNNN' (SEQ ID NO: 86) and 'NNNGNNN' (SEQ ID NO: 87) into the CDR3 regions of VL and VH, respectively.

The diversity was introduced by first creating a base scaffold that consisted of the framework sequence of IGLV3-1 and the J region for IGHV3-23 as follows:

Framework Sequence:

```
                                          (SEQ ID NO: 88)
ATG GGA GAC GGT CAG TCT GTG CTG ACT CAG CCA CCC

TCAGTGTCCGTGTCCCCAGGACAGACAGCCAGCATCACCTGCTCTGGAG

ATAAATTGGGGGATAAATATGCTTGCTGGTATCAGCAGAAGCCAGGCCA

GTCCCCTGTGCTGGTCATCTATCAAGATAGCAAGCGGCCCTCAGGGATC

CCTGAGCGATTCTCTGGCTCCAACTCTGGGAACACAGCCACTCTGACCA

TCAGCGGGACCCAGGCTATGGATGAGGCTGACTATTACTGTCAGGCG

TGG GAC tgagacctagacggtctct gcg TTT GAT ATT TGG

GGT CAA GGT ACC ATG GTT ACC GTG AGC AGC TCG TCT

CaG ACC.
```

This framework was cloned into the RED cytoplasmic expression vector with the PG and DNA binding domain elements via flanking BsmBI sites. The intervening sequence (the VL J region and IGHV3-23 framework) (SEQ ID NO: 89) was encoded on a separate plasmid that served as template for a PCR using degenerate primers (SEQ ID NOs: 90 and 91) that contained the CDR3 diversity of both the VL and VH regions at the 5' and 3' ends, respectively. These primer sequences had terminal BsaI restriction sites that enabled seamless cloning of the PCR product into appropriately orientated BsaI sites in the scaffold.

Intervening Sequence:

(SEQ ID NO: 89)
ACT GTG GTG TTC GGC acc ggt acg aaa gtg acT gtc

TCA TCT CAG ACC GGTGGTTCTGGTGGTGGTGGTTCTGGCGGCGGC

GGCTCCGGTGGTGGTGGATCCGAAGTCCAACTGCTGGAGTCCGGCGGTG

GCCTGGTGCAGCCAGGTGGCAGCCTGCGCCTGAGCTGCGCCGCATCCGG

TTTTACTTTCAGCAGCTACGCGATGTCGTGGGTGCGCCAGGCACCGGGC

AAGGGCCTGGAGTGGGTCAGCGCCATCAGCGGTAGCGGCGGTTCTACGT

ATTATGCGGACAGCGTCAAGGGCCGTTTCACCATCAGCCGTGACAATTC

CAAAAACACCCTGTACTTGCAGATGAACAGCTTGCGTGCGGAAGATACG

GCTGTTTACTACTGTGCGAAA

Degenerate Primer 1:

(SEQ ID NO: 90)
gatcag ggtctca ggac NNT NNT NNT ggc gga NNT NNT

NNT ACT GTG GTG TTC GGC acc ggt acg aaa gtg

Degenerate Primer 2:

(SEQ ID NO: 91)
GATCAGGGTCTCAACGCANNANNANNGCCANNANNANNTTTCGCACAGT

AGTAAACAGCCGTATCTTC

10 μg of the base scaffold vector was cut with BsaI. The cut vector was precipitated using Sureclean (Bioline). The insert, containing the CDR3 diversity regions, was PCR generated from the core framework as template using primers SEQ ID Nos: 90 and 91. 2 μg of insert PCR was gel-purified before digestion with BsaI. The PCR digest was precipitated using Sureclean. Equimolar amounts of digested vector and PCR insert were ligated using T4 DNA ligase. The ligation was heat-killed and serially electroporated into *Argentum E. coli* cells (Alchemy Bio). Electroporated cells were spread onto 15 cm LB+carbenicillin (40 μg/mL)+glucose (0.1%) agar plates. The total library size was >1×10$^8$ independent clones.

The quality of the library build was assessed by expression of the diversified scFv's. As formerly noted, expression of soluble, partially soluble or insoluble fusion partners can be directly assessed by the appearance of the scFv in the RED display system using the peptidoglycan (PG) binding domain and a chromogenic expression reporter such as SNAP (New England Biolabs). A soluble fusion protein is notably evenly distributed around the perimeter of the cell as it is free to diffuse and bind to the cell wall once the membranes have been permeabilised (e.g. FIG. 1A). In comparison, an insoluble fusion protein forms a densely staining aggregate that does not migrate to the cell wall (e.g. FIG. 1B). A partially soluble fusion has some characteristics of each. We had previously found an excellent correlation between the appearance of a fusion protein, as described above, and the quantity appearing in the soluble/insoluble fractions in Western blots such as the soluble scFv in FIG. 4.

Figure 9:
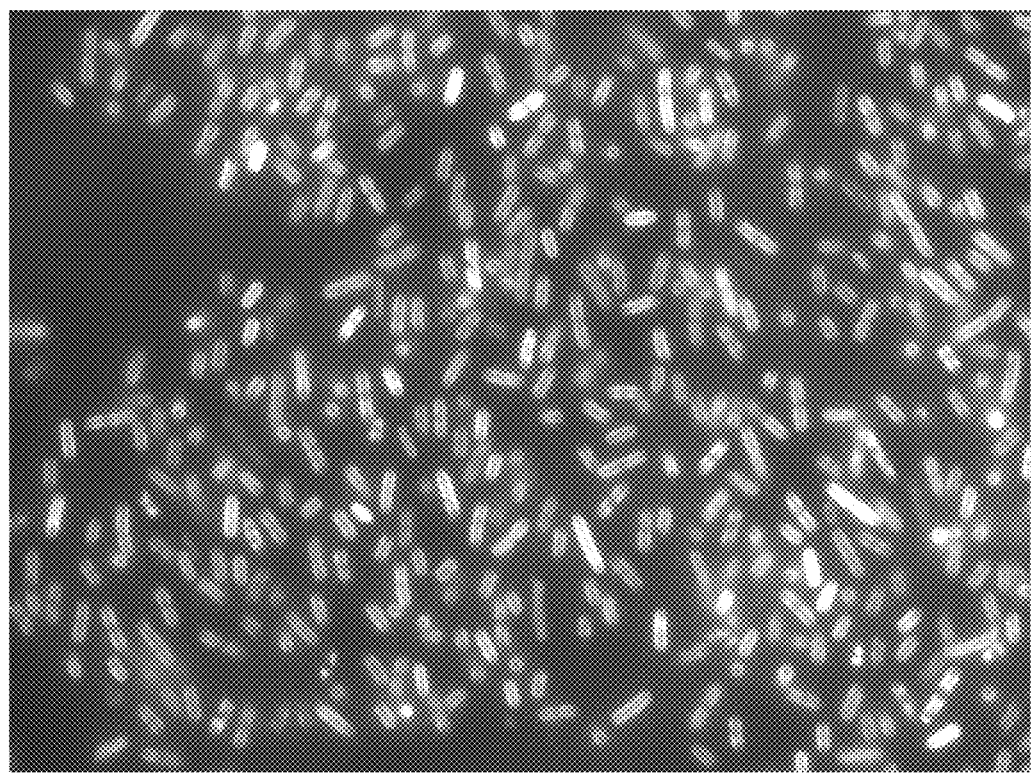

By this empirical standard, our diversified scFv library was composed of ~90% soluble and well-expressed members, which indicated the tolerance of the IGLV3-1::IGHV3-23 scaffold for the inserted CDR3 diversity. FIG. 9 is a SNAP labeled image of a sample of the expressed library.

To further confirm that the library was composed of randomized $V_L$ and $V_H$ CDR3 regions, 10 independent clones were sequenced. The sequencing showed that the composition of the CDR3 loops (shown in Table 4) was that expected for a codon diversity created by the 'NNT' nucleotide triplet used for degeneracy, i.e. the absence of stop codons, and the amino acids W, Q, M, K, and E.

TABLE 4

Sample CDR3 loop sequences in randomised library

| Clone | VL CDR3 | VH CDR3 |
|---|---|---|
| 1 | PFGGGGYV (SEQ ID NO: 92) | PPHGAPA (SEQ ID NO: 93) |
| 2 | LCIGGVAS (SEQ ID NO: 94) | HNSGNNF (SEQ ID NO: 95) |
| 3 | FVSGGIST (SEQ ID NO: 96) | FNFGNAY (SEQ ID NO: 97) |
| 4 | INSGGASF (SEQ ID NO: 98) | XXXGTNY (SEQ ID NO: 99) |
| 5 | SRAGGCNG (SEQ ID NO: 100) | FDYGHCI (SEQ ID NO: 101) |
| 6 | TNRGGVCA (SEQ ID NO: 102) | TAAGVPF (SEQ ID NO: 103) |
| 7 | Mixed clone | Mixed clone |
| 8 | FSTGGCAF (SEQ ID NO: 104) | AICGATA (SEQ ID NO: 105) |
| 9 | FXGGGDGT (SEQ ID NO: 106) | PYRGSFF (SEQ ID NO: 107) |
| 10 | IIPGGLYA (SEQ ID NO: 108) | PVIGSNT (SEQ ID NO: 109) |

Example 7

Screening of the IGVL3-1::IGVH3-23 Library for Binding to mAG1 Target

The diversified library was screened for clones that bound to a target protein, mAG. Azami-Green (AG) is a distant ortholog of the *Aequorea victoria* green fluorescent protein (GFP). Although of low sequence identity (5%), it is similarly green fluorescent with an absorption peak at 492 nm and emission peak at 510 nm. A monomeric form (mAG) was reported by Karasawa et al. (2003) and was re-coded for optimal expression in *E. coli* by DNA2.0 (USA). A C-terminal *E. coli* BirA biotinylation motif and 6×His tag was included to aid in purification and mAG matrix attachment. The amino acid sequence of the mAG-BioHis6 protein is listed as SEQ ID NO:110.

mAG BioHis6 Protein Sequence:

(SEQ ID NO: 110)
MVSVIKPEMKIKLCMRGTVNGHNFVIEGEGKGNPYEGTQILDLNVTEGAPLPFAYDILTT

VFQYGNRAFTKYPADIQDYFKQTFPEGYHWERSMTYEDQGICTATSNISMRGDCFFYDI

RFDGTNFPPNGPVMQKKTLKWEPSTEKMYVEDGVLKGDVNMRLLLEGGGHYRCDFKT

TYKAKKEVRLPDAHKIDHRIEILKHDKDYNKVKLYENAVARYSMLPSQAKSGGLNDIFE

AQKIEWHEDTGGSHHHHHH $10^{10}$ cells of the diversified library, representing a ~100-fold redundancy were induced for RED display as described in Example 2 and in WO 2011/075761. The permeabilised cells were suspended in 50 mL PBS and were labeled with purified mAG that had been pre-bound to MACS streptavidin-conjugated microbeads (130-048-102, Miltenyi Biotec). The cells and microbeads were gently agitated overnight at 4° C. They were then loaded onto 3×LS columns (130-042-401, Miltenyi Biotec) that were fixed to a magnetic support. Each column was washed with 50 mL of PBS. The cells were eluted in 10 mL PBS, pooled and pelleted. Plasmid DNA encoding the library in the RED display vector was isolated from the cell pellet by the alkaline lysis. The plasmid was then electroporated back into *Argentum* cells and the induction, binding and column purification was repeated. After four iterations of the affinity screen, a low abundance of RED permeabilised cells were observed by fluorescence microscopy to be binding to the mAG protein. At the fifth iteration the permeabilised cells were sorted for mAG binding by FACS. Cells were labeled for FACS using SNAP ligand, to normalise the fusion protein expression, and mAG. FACS of the cell population during the collection of 4,428 mAG-positive events from $2.46 \times 10^8$ total events showed an abundance of approximately 1 binding event in $10^5$ cells. The scFv from the mAG-positive cells that were the FACS output were recovered by PCR using oligonucleotide primers flanking the scFv sequence and the product was re-cloned back into the RED display vector. Analysis of the final screen output for cells that were positive for mAG binding showed that ~40% (23/60) of the clones were mAG1-positive. Thus, the FACS stage was capable of an ~$10^5$-fold enrichment of positive cells from the library background.

Figure 10:
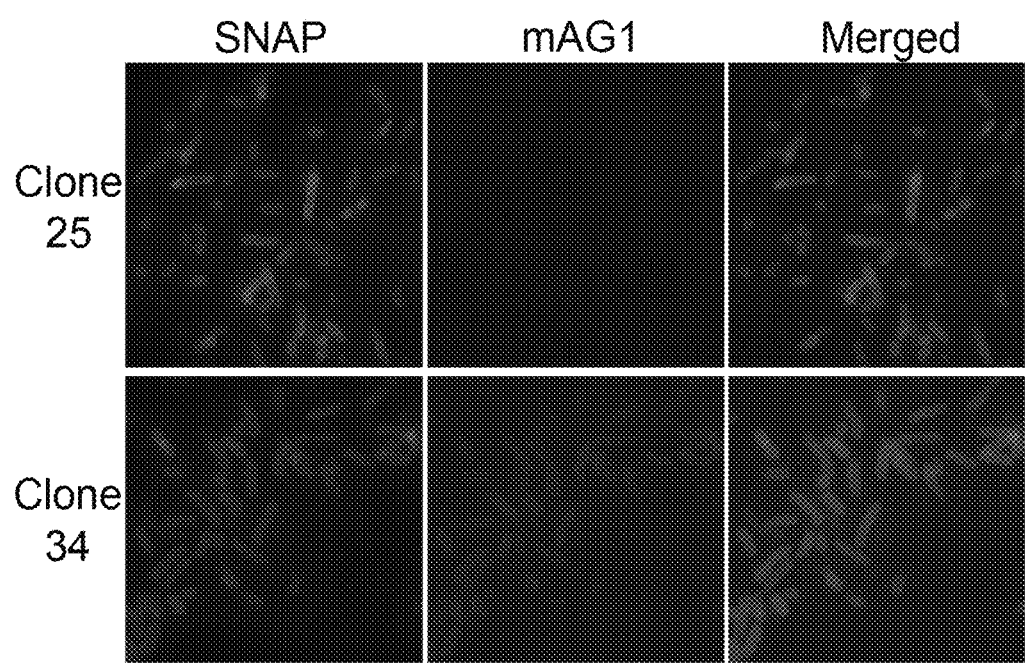

FIG. 10 shows the binding of mAG to RED permeabilised cells for clones that was negative (clone 25) and positive (clone 34) for mAG binding.

Figure 11:
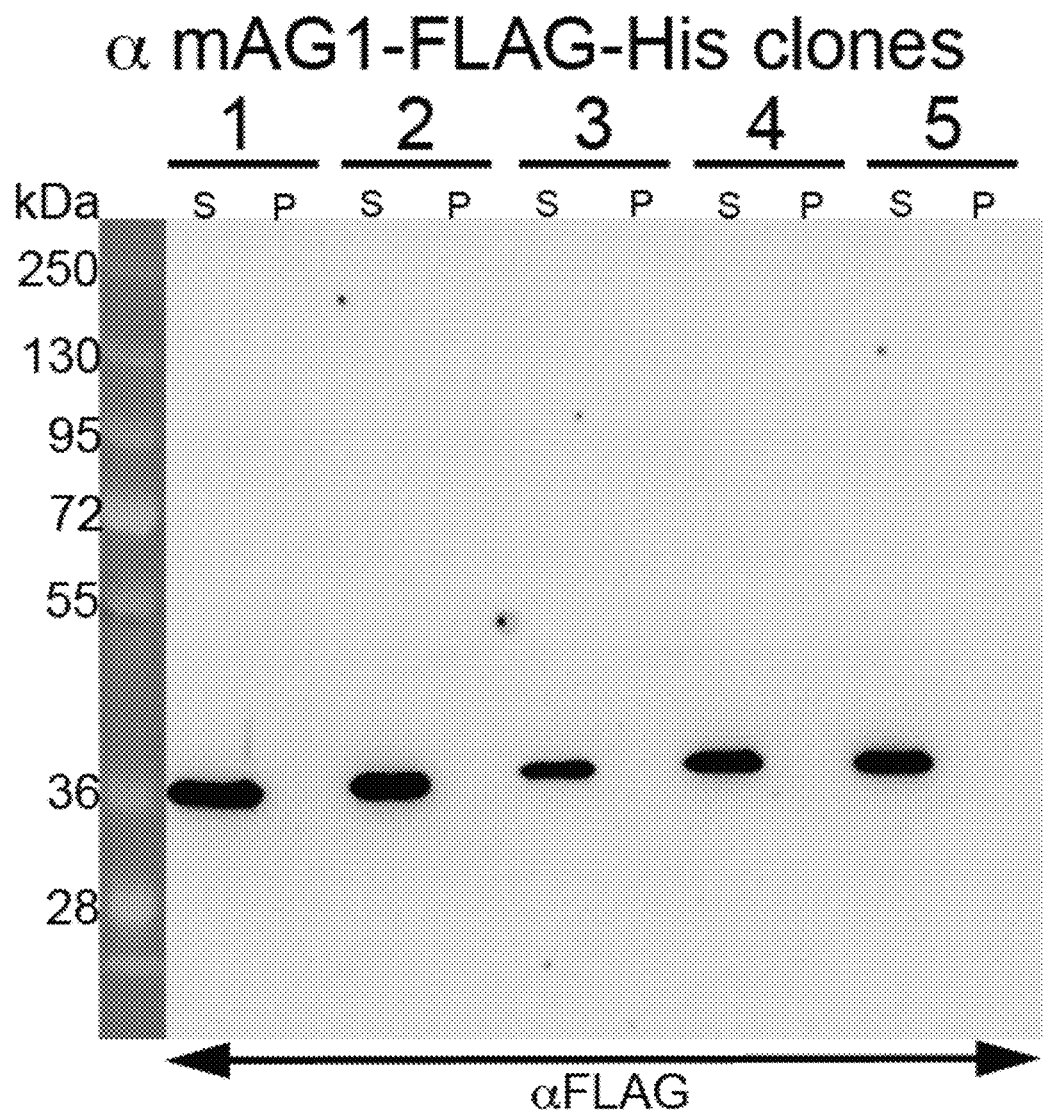
FIG. 11 illustrates the soluble nature of the IGLV3-1::IGHV3-23 scFv scaffold with the entirety of the α-mAG scFv isolated from the RED screen cloned as a C-terminal His6 FLAG fusion protein present in the soluble fraction (S), with no protein in the insoluble fraction (P). Detection was using an α-FLAG monoclonal antibody.

20 mAG-positive clones were sequenced and it was found that all 20 were identical. The protein sequence of the mAG-binding IGLV3-1::IGHV3-23 clone is listed in SEQ ID NO: 111 below (with CDR3 sequences in bold and enlarged font, and peptide linker underlined). The VL CDR3 was found to be 'FNLGGCGD' and the VH CDR3 'HIDG-PVA' which conforms with the designed diversity.
Anti-mAG Binding scFv:

To determine the properties of the α-mAG scFv, the gene was cloned into an expression vector with a C-terminal 6×His and a FLAG epitope tag. scFv expression was induced with arabinose and the cells permeabilised with 0.5% 8TGP to release soluble scFv into the supernatant. The insoluble cellular material was pelleted and samples of both extracts were boiled with SDS-PAGE loading dye and electrophoresed on a 15% SDS-PAGE gel. The resolved proteins were transferred to nitrocellulose membrane and probed with an α-FLAG mouse monoclonal antibody. FIG. 11 demonstrates that the α-mAG scFv was almost exclusively in the soluble fraction.

Figure 12:
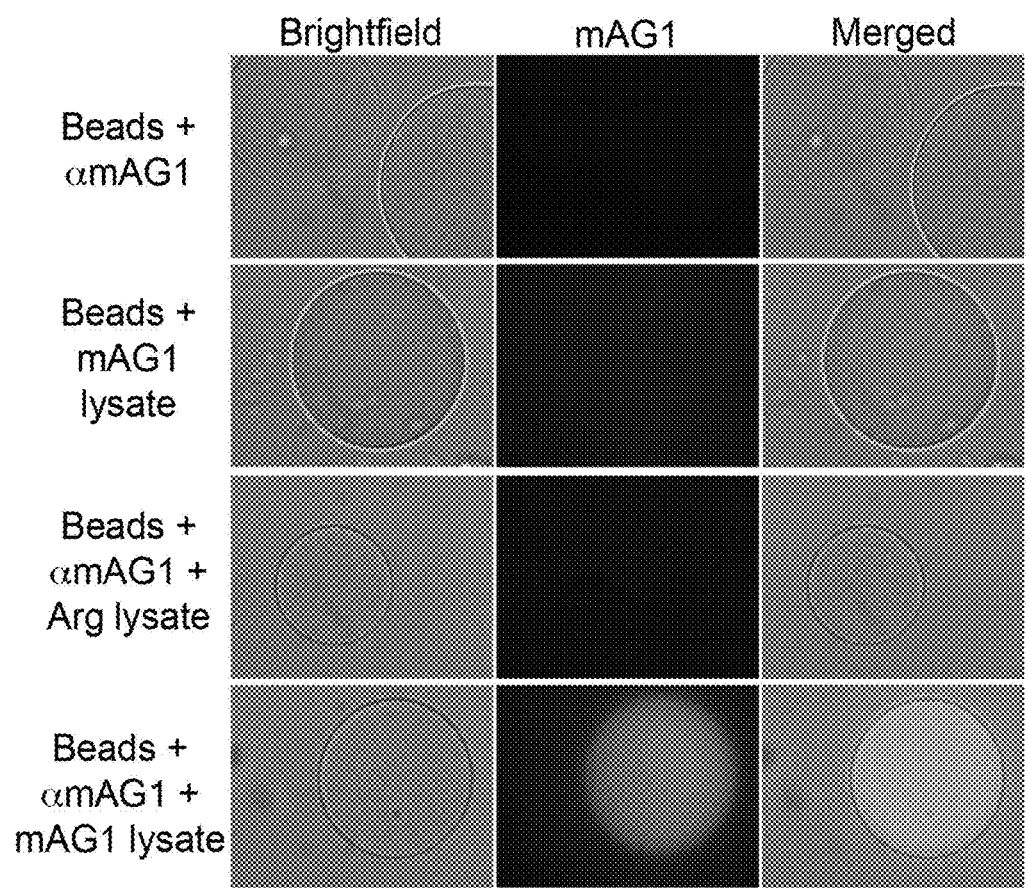
FIG. 12 shows the binding of mAG by the α-mAG scFv His6FLAG fusion bound to IMAC Ni-sepharose.

To demonstrate that the α-mAG scFv was specific to mAG protein, and not merely a 'sticky' antibody, α-mAG scFv permeabilised cells were labeled with the structurally and functionally mAG related protein, EGFP. These cells, while binding mAG, did not bind EGFP (data not shown). To further evaluate the specificity of the α-mAG scFv, the α-mAG scFv His6-FLAG protein was also bound to IMAC Ni-sepharose resin. A crude cell lysate of 'clean' mAG protein (with the His6 and FLAG tags removed) was mixed with the resin. Unbound proteins were washed free. Fluorescence microscopy images in FIG. 12 demonstrate that the resin beads with attached α-mAG scFv bound mAG, whereas control beads did not. The bound proteins were eluted with imidazole and electrophoresed on a SDS-PAGE gel. Coomassie staining of the gel (FIG. 13) demonstrated a band in the α-mAG scFv sample that was of the correct size to be mAG protein with no other bands specific to the mAG cell lysate evident.

Thus, the present invention can be used successfully to generate a library of scFv polypeptides containing randomised CDR3 loops and screened to identify scFvs showing specific binding activity.

Example 8

Lambda Phage Display Using the α-mAG IGLV3-1::IGHV3-23 scFv

To demonstrate the utility of a scaffold that exhibits enhanced stability and productive folding in the reducing environment of the cytoplasm, the α-mAG IGLV3-1::IGHV3-23 scFv was cloned as a C-terminal fusion to the (SEQ ID NO: 111)
MGDGQSVLTQPPSVSVSPGQTASITCSGDKLGDKYACWYQQKPGQSPVLVIYQDSKRP

SGIPERFSGSNSGNTATLTISGTQAMDEADYYCQAWDFNLGGCGDTVVFGTGTKVTVSSQ

<u>TGGSGGGGSGGGGSGGGGS</u>EVQLLESGGGLVQPGGSLRLSCAASGFTFSSYAMSWVRQAP

GKGLEWVSAISGSGGSTYYADSVKGRFTISRDNSKNTLYLQMNSLRAEDTAVYYCAKHID

GPVAAFDIWGQGTMVTVSSSSQTSILVA lambda bacteriophage gpD capsid protein. Lambda bacteriophage has long been reported as an exemplary vehicle for protein display as it has a number of advantages over filamentous phage. The lambda capsid protein, gpD, is present in ~400 copies per phage head, and is a robust and tolerant display partner, allowing >80% of the gpD loaded per capsid to be recombinant fusion proteins while maintaining infectious viability (Vaccaro et al., 2006). Furthermore, it is tolerant of fusions to either its N- or C-terminal end.

Therefore, a lambda bacteriophage, or equivalently packaged vector, has a multivalent display of the library protein, compared to the nominally single molecule display of filamentous phage. This multivalent display can result in phenomenal capture efficiencies of the phage from a binding solution—up to almost 100% capture (Mikawa et al., 1996). Additionally, the assembly of lambda bacteriophage libraries is facilitated by the commercial availability of kits that enable high efficiency packaging of lambda (up to $2 \times 10^9$ pfu/µg).

However, lambda bacteriophage has not enjoyed the popularity of use of filamentous phage for antibody display due to the singular fact that lambda, and related phage such as P2/P4, P22, T7 and T4, have a lytic lifestyle that results from their assemblage in the cytoplasm. As the great majority of antibody scaffolds are not productively folded without oxidized interdomain disulphide bridges, this has largely precluded the use of lambda bacteriophage for antibody display.

Our identification of a number of IGLV partners for the IGHV3-23 domain that form a cytoplasmically stable scFv scaffold has enabled us to demonstrate the exemplary application of lambda display for antibody screening. The α-mAG scFv was cloned as a C-terminal fusion to the lambda gpD capsid protein with the expression of the fusion protein under control of the arabinose-inducible araBAD promoter and araC regulator. This unit was cloned into the lambda bacteriophage genome similarly to other lambda display platforms (Mikawa et al., 1996; Sternberg and Hoess, 1995; Minenkova et al., 2003), with the notable exception that the lambda genome used was genetically cI857 gpD$^+$ RS$^-$. The deletion of the RS genes, which constitute the lambda endolysin (R) and porin (S) genes necessary for cellular lysis, was described in International Patent Application No. PCT/AU2012/000761 for the use of lysis-defective bacteriophage in lambdoid display. A lysis-defective phage vector used for lambdoid display enables the packaging of an infective bacteriophage particle within the cytoplasm. These particles continue to accumulate within the cell, with their capsid fusion protein tethered on their surface at high density, until growth is halted by the researcher processing the host bacterial cells for cytoplasmic RED display. The resultant preparation may thereby be screened for fusion protein antigen binding by FACS. To release the bacteriophage particles that are encapsulated within the permeabilised cell that have been positively sorted by FACS for antigen binding merely requires the addition of a lysozyme. A highly active lysozyme preparation may be purchased commercially for this task (e.g. Ready-Lyse from Epicentre). To complete the recovery of the affinity-selected clones the infectious bacteriophage particles may be infected into host E. coli cells and grown as lysogens. Thus, it should be appreciated by practitioners of the art that the use of lysis-defective phage, in conjunction with a cytoplasmically stable human antibody scaffold, enables high capture frequencies of polyvalent library clones in the free-bacteriophage format, with the final screen being conducted by FACS. Importantly, this change in screening format occurs without any requirement for reformatting of the library expression construct. Thus, this is a screening system that has dual capability for both highly-parallel screening (free bacteriophage panning) with low clonal selectivity and a screen with high clonal selectivity but low throughput (FACS of encapsulated bacteriophage).

To demonstrate the benefits of lambda phage display using the polypeptides of the present invention, the model α-mAG scFv fusion (as one of many suitable examples of the polypeptides of the present invention) was cloned as a C-terminal fusion to the lambda capsid gpD gene.

The DNA sequence of the gpD::α-mAG scFv fusion construct used was:

(SEQ ID NO: 112)

```
ATGACGAGCAAAGAAACCTTTACCCATTACCAGCCGCAGGGCAACAGTG

ACCCGGCTCATACCGCAACCGCGCCCGGCGGATTGAGTGCGAAAGCGCC

TGCAATGACCCCGCTGATGCTGGACACCTCCAGCCGTAAGCTGGTTGCG

TGGGATGGCACCACCGACGGTGCTGCCGTTGGCATTCTTGCGGTTGCTG

CTGACCAGACCAGCACCACGCTGACGTTCTACAAGTCCGGCACGTTCCG

TTATGAGGATGTGCTCTGGCCGGAGGCTGCCAGCGACGAGACGAAAAAA

CGGACCGCGTTTGCCGGAACGGCAATCAGCATCGTTGGAGGTAGCGGCG

GATCGGATGACGACGATAAGTCTAGAAATGGCGGAGACGGTCAGTCTGT

GCTGACTCAGCCACCCTCAGTGTCCGTGTCCCCAGGACAGACAGCCAGC

ATCACCTGCTCTGGAGATAAATTGGGGGATAAATATGCTTGCTGGTATC

AGCAGAAGCCAGGCCAGTCCCCTGTGCTGGTCATCTATCAAGATAGCAA

GCGGCCCTCAGGGATCCCTGAGCGATTCTCTGGCTCCAACTCTGGGAAC

ACAGCCACTCTGACCATCAGCGGGACCCAGGCTATGGATGAGGCTGACT

ATTACTGTCAGGCGTGGGACTTTAATCTTGGCGGATGTGGTGATACTGT

GGTGTTCGGCACCGGTACGAAAGTGACTGTCTCATCTCAGACCGGTGGT

TCTGGTGGCGGTGGTTCTGGCGGCGGCGGCTCCGGTGGTGGTGGATCCG

AAGTCCAACTGCTGGAGTCCGGTGGTGGCCTGGTGCAGCCAGGTGGCAG

CCTGCGCCTGAGCTGCGCCGCATCCGGTTTTACTTTCAGCAGCTACGCG

ATGTCGTGGGTGCGCCAGGCACCGGGCAAGGGCCTGGAGTGGGTCAGCG

CCATCAGCGGTAGCGGCGGTTCTACGTATTATGCGGACAGCGTCAAGGG

CCGTTTCACCATCAGCCGTGACAATTCCAAAAACACCCTGTACTTGCAG

ATGAACAGCTTGCGTGCGGAAGATACGGCTGTTTACTACTGTGCGAAAC

ATATTGATGGCCCTGTTGCTGCGTTTGATATTTGGGGTCAAGGTACCAT

GGTTACCGTGAGCAACTCGAGCGATTACAAGGACGATGATGACAAATAA
```

The protein sequence of the gpD::α-mAG scFv fusion protein used was:

(SEQ ID NO: 113)
MTSKETFTHYQPQGNSDPAHTATAPGGLSAKAPAMTPLMLDTSSRKLVAWDGTTDGAAVG

ILAVAADQTSTTLTFYKSGTFRYEDVLWPEAASDETKKRTAFAGTAISIVGGSGGSDDDD

KSRNGGDGQSVLTQPPSVSVSPGQTASITCSGDKLGDKYACWYQQKPGQSPVLVIYQDSK

RPSGIPERFSGSNSGNTATLTISGTQAMDEADYYCQAWDFNLGGCGDTVVFGTGTKVTVS

SQTGGSGGGGSGGGGSGGGGSEVQLLESGGGLVQPGGSLRLSCAASGFTFSSYAMSWVRQ

APGKGLEWVSAISGSGGSTYYADSVKGRFTISRDNSKNTLYLQMNSLRAEDTAVYYCAKH

IDGPVAAFDIWGQGTMVTVSNSSDYKDDDDK*

The gpD::α-mAG scFv fusion was then cloned into the lambda display vector under the control of the araBAD promoter. The host cells were induced for lambda packaging by heating the lysogen clone at 42° C. for 15 minutes (the lambda genetic background was cI857 gpD⁺ RS⁻ with the temperature sensitive cI repressor). The fusion protein was induced with 0.2% arabinose immediately following thermal induction. The culture was grown, with aeration, at 32° C. for a further 75 minutes. The cells were pelleted and resuspended in $\frac{1}{3}^{rd}$ culture volume of LB media+0.5% 8TGP and incubated at 25° C. for 10 minutes to permeabilise the cells by the RED method for screening. To release the phage, $\frac{1}{10,000}^{th}$ culture volume of Ready-Lyse (Epicentre) lysozyme was added to the suspension. A drop of chloroform was added to inactivate any surviving cells and the bacteriophage particles released were titred for lysogen forming units (cfu/mL). Two bacteriophage stocks were made—one with the construct with the cloned gpD::α-mAG scFv fusion, the other an empty construct. The gpD::α-mAG scFv fusion was diluted to 1 clone in 10⁹ of empty construct, to simulate a starting scFv library density of only a few positive clones. This 'doped' library was then panned against biotinylated mAG bound to a streptavidin bead support. The panning was conducted according to methods commonly used for phage panning known to practitioners of the art. Two rounds of panning were conducted with the final round being recovered into the host E. coli strain as lysogens. The third round of screening was conducted by FACS. The lysogen cells were treated as described above for heat-induction of bacteriophage along with arabinose-induction of the gpD::α-mAG scFv fusion. However, instead of releasing the bacteriophage particles with lysozyme treatment, the permeabilised cells were instead incubated with mAG protein. The permeabilised cells were washed once, resuspended in TBS+10 mM MgSO4 and then sorted for mAG binding (i.e. mAG-positive cells would be labeled green) by FACS. FIG. 14 (TOP) shows a screen-grab of the FACS sort in operation demonstrating the incidence of mAG-positive cells. The final incidence of mAG-positive cells post-FACS, assessed by fluorescence microscopy (FIG. 14, BOTTOM), was 20%.

Thus, it has been demonstrated that lambda capsid display, in conjunction with the stable and soluble scFv scaffolds of the present invention, can robustly isolate binding clones from a relatively high starting dilution (1 in 10⁹). Furthermore, when combined with a lysis-defective bacteriophage and treated by the method taught by RED, enables a further magnification of the beneficial properties to include the capability of FACS screening without recloning of the library members.

The combination of these methods greatly accelerate the screening process for antibody clones with ideal properties (high expression, high solubility and high affinity).

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Al-Lazikani et al. (1997) J Mol Biol 273:927-948.
Altschul et al. (1993) J. Mol. Biol. 215: 403410.
Auf der Maur et al. (2002) JBC 277:45075-45085.
Becker et al. (2004) Curr. Opin. Biotech. 15:323-329.
Bork et al. (1994) J. Mol. Biol. 242: 309-320.
Borrebaeck (ed) (1995) Antibody Engineering. Oxford University Press.
Brezinschek et al. (1997) J. Clin. Invest. 99:2488-2501.
Briers et al. (2009) Biochem. Biophys. Res. Comm. 383: 187-191.
Chen W et al. (2008) JMB 382:779-789.
Chothia and Lesk (1987) J. Mol. Biol. 196:901-917.
Chothia et al. (1989) Nature 342:877-883.
Contreras-Martinez and DeLisa (2007) JMB 372:513-524.
Daugherty et al. (2000) J. Immunol. Methods 243:211-227.
Ewert et al. (2003) JMB 325: 531-553.
Fisher and Delisa (2009) JMB 385:299-311.
Froyen et al. (1995) Mol. Immunol. 37: 515-521.
Ge et al. (2010) Biotech Bioeng 106, 347-57.
Griffiths et al. (1994) EMBO J. 13:3245-3260.
Guan et al. (1998) Proc. Natl. Acad. Sci. USA, 95: 13206-10.
He et al. (1995) NAR 23:4009-4010.
Higgins and Sharp (1989) CABIOS. 5: 151-153.
Hust and Dubel (2010) Antibody Eng. Chapter 5: Antibody Engineering, Vol 1; Springer.
Jermutus et al. (2001) PNAS 98:75-80.
Jirholt et al. (1998) Gene 215, 471-476.
Jurado et al. (2002)JMB 320:1-10.
Kabat (1987 and 1991) Sequences of Proteins of Immunological Interest. National Institutes of Health.
Karasawa et al. (2003) JBC 278:34167-34171.
Kenrick et al. (2007) Curr. Prot. Cyt. 4.6.1-4.6.27.
Kirchhofer et al. (2010) Nat. Struct. Mol. Bio. 17:133-139.

Knappik et al. (2000) JMB 296:57-86.
Kobayashi et al. (1997) Biotechniques 23:500-503.
Lefranc (2000) Curr. Prot. 1 mm. 1-37.
Lutz and Patrick (2004) Curr. Opin. Biot. 15:291-297.
Marsh et al. (2000) Hum. Mol. Genet. 9:13-25.
Martineau et al. (1998) JMB 280:117-127.
Mikawa et al. (1996) JMB 262:21-30.
Miller et al. (2006) Nat. Meth. 3:561-570.
Minenkova et al. (2003) Int J Can 106:534-544.
Parsons et. al. (2006) Biochem. 45:2122-2128.
Pini et al. (1998) JBC 273:21769-21776.
Plückthun (1992) Immunol. Revs., 130:151-188.
Saerens et al. (2005) JMB 352:597-607.
Skerra et al (1993) Curr. Opinion in Immunol. 5:256-262.
Smith (1985) Science 228:1315-1317.
Soderlind et al. (2000) Nat. Biotech. 18:852-856.
Sternberg and Hoess (1995) PNAS 92:1609-1613.
Stewart et al. (1993) J. Exp. Med. 177:409-418.
Tavladoraki et al. (1999) Eur. J. Biochem. 262:617-624.
Tse et al. (2002) JMB 317:85-94.
Vaccaro et al. (2006) J. Imm. Methods. 310:149-158.
Visintin et al. (1999) PNAS 96:11723-11728.
Vitetta et al. (1993) Immunol. Today 14: 252-259.
Viti et al. (2000) Meth. Enzy. 326:480-505

What is claimed is:

1. A polynucleotide library comprising a plurality of different polynucleotides, wherein each polynucleotide encodes a polypeptide comprising:
   i) an antibody heavy chain variable region ($V_H$) comprising a scaffold region which is at least 90% identical to the scaffold region of IGHV3-23 as set out in SEQ ID NO: 3; and
   ii) an antibody light chain variable region ($V_L$) comprising a scaffold region which is at least 90% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV3-1 (as set out in SEQ ID NO: 6), IGLV3-19 (as set out in SEQ ID NO: 27), or IGLV6-57 (as set out in SEQ ID NO: 12); wherein the $V_H$ and the $V_L$ are capable of forming an antigen-binding site; and
   wherein at least two of the polynucleotides differ from one another by encoding polypeptides comprising one or more different CDRs in the $V_H$, the $V_L$, or both,
   wherein each polynucleotide encodes a polypeptide that is soluble and capable of stably forming an antigen-binding site when produced under reducing conditions, and
   wherein each polynucleotide encodes a polypeptide that is a bispecific antibody, a chimeric antibody, a Fab fragment, a scFv, a diabody, a triabody, or a tetrabody and wherein when the polynucleotide encodes the polypeptide that comprises a $V_H$ and $C_{H1}$ of the Fab fragment, the polynucleotide also encodes either a stop codon following the $C_{H1}$ or a second polypeptide wherein the second polypeptide is not an Fc domain of an antibody.

2. A method of constructing a polynucleotide library, the method comprising preparing a plurality of different polynucleotides encoding a polypeptide, which comprises:
   i) an antibody heavy chain variable region ($V_H$) comprising a scaffold region which is at least 90% identical to the scaffold region of IGHV3-23 as set out in SEQ ID NO: 3; and
   ii) an antibody light chain variable region ($V_L$) comprising a scaffold region which is at least 90% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV3-1(as set out in SEQ ID NO: 6), IGLV3-19 (as set out in SEQ ID NO: 27), IGLV6-57 (as set out in SEQ ID NO: 12); wherein the $V_H$ and the $V_L$ are capable of forming an antigen-binding site; and
   wherein at least two of the polynucleotides differ from one another by encoding polypeptides comprising one or more different CDRs in the $V_H$, the $V_L$, or both,
   wherein each polynucleotide encodes a polypeptide that is soluble and capable of stably forming an antigen-binding site when produced under reducing conditions, and
   wherein each polynucleotide encodes a polypeptide that is a bispecific antibody, a chimeric antibody, a Fab fragment, a scFv, a diabody, a triabody, or a tetrabody and wherein when the polynucleotide encodes the polypeptide that comprises a $V_H$ and $C_{H1}$ of the Fab fragment, the polynucleotide also encodes either a stop codon following the $C_{H1}$ or a second polypeptide wherein the second polypeptide is not an Fc domain of an antibody.

3. A polynucleotide encoding a polypeptide comprising,
   i) an antibody heavy chain variable region ($V_H$) comprising a scaffold region which is at least 90% identical to the scaffold region of IGHV3-23 as set out in SEQ ID NO: 3; and
   ii) an antibody light chain variable region ($V_L$) comprising a scaffold region which is at least 90% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV3-1 (as set out in SEQ ID NO: 6), IGLV3-19 (as set out in SEQ ID NO: 27), IGLV6-57 (as set out in SEQ ID NO: 12); wherein the $V_H$ and the $V_L$ are capable of forming an antigen-binding site,
   wherein the polynucleotide encodes a polypeptide that is a bispecific antibody, a chimeric antibody, a Fab fragment, a scFv, a diabody, a triabody, or a tetrabody and wherein when the polynucleotide encodes the polypeptide that comprises a $V_H$ and $C_{H1}$ of the Fab fragment, the polynucleotide also encodes either a stop codon following the $C_{H1}$ or a second polypeptide wherein the second polypeptide is not an Fc domain of an antibody.

4. A vector comprising the polynucleotide of claim 3.

5. A host cell comprising the polynucleotide of claim 3.

6. The polynucleotide library of claim 1, wherein each polynucleotide encodes a polypeptide comprising a $V_L$ that comprises a scaffold region which is at least 90% identical to the scaffold region of IGLV3-1 as set out in SEQ ID NO.6.

7. The polynucleotide library of claim 1, wherein each polynucleotide encodes a polypeptide that is a scFv, and wherein and the $V_H$ and the $V_L$ are linked together via a peptide linker.

8. The polynucleotide library of claim 1, wherein the $V_H$ scaffold region is at least 95% identical to the scaffold region of IGHV3-23 as set out in SEQ ID NO: 3.

9. The polynucleotide library of claim 1, wherein the $V_H$ scaffold region is at least 96% identical to the scaffold region of IGHV3-23 as set out in SEQ ID NO: 3.

10. The polynucleotide library of claim 1, wherein the $V_H$ scaffold region is at least 97% identical to the scaffold region of IGHV3-23 as set out in SEQ ID NO: 3.

11. The polynucleotide library of claim 1, wherein the $V_H$ scaffold region is at least 98% identical to the scaffold region of IGHV3-23 as set out in SEQ ID NO: 3.

12. The polynucleotide library of claim 1, wherein the $V_H$ scaffold region is at least 99% identical to the scaffold region of IGHV3-23 as set out in SEQ ID NO: 3.

13. The polynucleotide library of claim 1, wherein the $V_L$ scaffold region is at least 95% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV3-1 (as set out in SEQ ID NO: 6), IGLV3-19 (as set out in SEQ ID NO: 27), or IGLV6-57 (as set out in SEQ ID NO: 12).

14. The polynucleotide library of claim 1, wherein the $V_L$ scaffold region is at least 96% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV3-1 (as set out in SEQ ID NO: 6), IGLV3-19 (as set out in SEQ ID NO: 27), or IGLV6-57 (as set out in SEQ ID NO: 12).

15. The polynucleotide library of claim 1, wherein the $V_L$ scaffold region is at least 97% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV3-1 (as set out in SEQ ID NO: 6), IGLV3-19 (as set out in SEQ ID NO: 27), or IGLV6-57 (as set out in SEQ ID NO: 12).

16. The polynucleotide library of claim 1, wherein the $V_L$ scaffold region is at least 98% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV3-1 (as set out in SEQ ID NO: 6), IGLV3-19 (as set out in SEQ ID NO: 27), or IGLV6-57 (as set out in SEQ ID NO: 12).

17. The polynucleotide library of claim 1, wherein the $V_L$ scaffold region is at least 99% identical to the scaffold region of any one of IGLV1-40 (as set out in SEQ ID NO: 18), IGLV1-44 (as set out in SEQ ID NO: 21), IGLV1-47 (as set out in SEQ ID NO: 24), IGLV3-1 (as set out in SEQ ID NO: 6), IGLV3-19 (as set out in SEQ ID NO: 27), or IGLV6-57 (as set out in SEQ ID NO: 12).

* * * * *

UNITED STATES PATENT AND TRADEMARK OFFICE
CERTIFICATE OF CORRECTION

PATENT NO. : 10,087,261 B2
APPLICATION NO. : 14/181026
DATED : October 2, 2018
INVENTOR(S) : Matthew David Beasley, Keith Philip Niven and Ben Ross Kiefel Page 1 of 1

It is certified that error appears in the above-identified patent and that said Letters Patent is hereby corrected as shown below:

In the Claims

Column 122, Line 14 (approx.): In Claim 3, below "site," insert -- wherein the polynucleotide encodes a polypeptide that is soluble and capable of stably forming an antigen-binding site when produced under reducing conditions, and --.

Signed and Sealed this
Fourth Day of December, 2018

Andrei Iancu
*Director of the United States Patent and Trademark Office*

SEQUENCE LISTING

```
<160> NUMBER OF SEQ ID NOS: 125

<210> SEQ ID NO 1
<211> LENGTH: 456
<212> TYPE: DNA
<213> ORGANISM: Homo sapiens

<400> SEQUENCE: 1
tctttcgcac agtaatatac ggccgtgtcc tcggctctca ggctgttcat ttgcagatac    60
agcgtgttct tggaattgtc tctggagatg gtgaaccggc ccttcacgga gtctgcgtag   120
tatgtgctac caccactacc actaatagct gagacccact ccagcccctt ccctggagcc   180
tggcggaccc agctcatggc atagctgcta aaggtgaatc cagaggctgc acaggagagt   240
ctcagggacc cccaggctg taccaagcct ccccagact ccaacagctg cacctcacac    300
tggacacctg caaacaaaaa gaaaccctgg tcagaaactg ccacacgtat ccactgtttc   360
tctcactctt atccattcac actcaatttt tctatttctc catgaattac cttttaaaat   420
agccacaaga aaaagccagc tcagcccaaa ctccat                             456

<210> SEQ ID NO 2
<211> LENGTH: 296
<212> TYPE: DNA
<213> ORGANISM: Homo sapiens

<400> SEQUENCE: 2
gaggtgcagc tgttggagtc tgggggaggc ttggtacagc ctgggggtc cctgagactc     60 tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gaaaga       296

<210> SEQ ID NO 3
<211> LENGTH: 98
<212> TYPE: PRT
<213> ORGANISM: Homo sapiens

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys

<210> SEQ ID NO 4
<211> LENGTH: 481
<212> TYPE: DNA
<213> ORGANISM: Homo sapiens

<400> SEQUENCE: 4
atgaccctgc tgcaggtgga tgggctcggc ggggctgaaa tcccccaca cagtgctcat      60
gtgctcacac tgccttaggg ctctttcatc cctggatctg tgtccaggcc aggcacgtgg    120
gaagatttac ttggagttca gctcctcagt ttcaagcctt ttctctcccg ttttctctcc    180
tgtaggatcc gtggcctcct atgagctgac tcagccaccc tcagtgtccg tgtccccagg    240
acagacagcc agcatcacct gctctggaga taaattgggg gataaatatg cttgctggta    300
tcagcagaag ccaggccagt cccctgtgct ggtcatctat caagatagca agcggccctc    360
agggatccct gagcgattct ctggctccaa ctctgggaac acagccactc tgaccatcag    420
cgggacccag gctatggatg aggctgacta ttactgtcag cgtgggaca gcagcactgc    480
a                                                                    481

<210> SEQ ID NO 5
<211> LENGTH: 285
<212> TYPE: DNA
<213> ORGANISM: Homo sapiens

<400> SEQUENCE: 5
tcctatgagc tgactcagcc accctcagtg tccgtgtccc caggacagac agccagcatc     60
acctgctctg gagataaatt gggggataaa tatgcttgct ggtatcagca gaagccaggc    120
cagtcccctg tgctggtcat ctatcaagat agcaagcggc cctcagggat ccctgagcga    180
ttctctggct ccaactctgg gaacacagcc actctgacca tcagcgggac ccaggctatg    240
gatgaggctg actattactg tcaggcgtgg gacagcagca ctgca                    285

<210> SEQ ID NO 6
<211> LENGTH: 95
<212> TYPE: PRT
<213> ORGANISM: Homo sapiens

<400> SEQUENCE: 6

Gln Ser Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala
            85                  90                  95

<210> SEQ ID NO 7
<211> LENGTH: 781
<212> TYPE: DNA
<213> ORGANISM: Homo sapiens

<400> SEQUENCE: 7

```
atggcctgga ccgttctcct cctcggcctc ctctctcact gcacaggtga tcccccagg      60
gtctcaccaa cctgcccagc caagggttc tgggtccagc gtgtccttga ttctgagctc     120
aggagggccc ttcctgtggt gggcaggatg ctcatgaccc tgctgcaggg tgggaggctg     180
gtggggctga actcccccca aactgtgctc aaaggcttgt gagagcctga gggactgcac     240
ctgccaggag agagtagtga gttttcagtt caaagtctcc atacaacagg aaagtcatgg     300
gccactgggg ctgggctga ttgcagggga taccctgagg gttcacagac tctctggagc      360
ttgtctggga cagcagggca agggatttca taagaagcat ctttcacctg caagccaacc     420
tctctcttat ttatttattt atttatttat ttatttattt atttattttt atctttgcag     480
gctctgtgac ctcctatgtg ctgactcagc caccctcggt gtcagtggcc ccaggacaga     540
cggccaggat tacctgtggg ggaaacaaca ttggaagtaa agtgtgcac tggtaccagc      600
agaagccagg ccaggcccct gtgctggtcg tctatgatga tagcgaccgg ccctcaggga     660
tccctgagcg attctctggc tccaactctg gaacacggc caccctgacc atcagcaggg      720
tcgaagccgg ggatgaggcc gactattact gtcaggtgtg ggatagtagt agtgatcatc     780
c                                                                      781
```

<210> SEQ ID NO 8
<211> LENGTH: 290
<212> TYPE: DNA
<213> ORGANISM: Homo sapiens

<400> SEQUENCE: 8

```
tcctatgtgc tgactcagcc accctcggtg tcagtggccc caggacagac ggccaggatt     60
acctgtgggg gaaacaacat tggaagtaaa agtgtgcact ggtaccagca gaagccaggc    120
caggcccctg tgctggtcgt ctatgatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgatcatcc                290
```

<210> SEQ ID NO 9
<211> LENGTH: 97
<212> TYPE: PRT
<213> ORGANISM: Homo sapiens

<400> SEQUENCE: 9

```
Gln Ser Val Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95
```

Pro

<210> SEQ ID NO 10
<211> LENGTH: 478
<212> TYPE: DNA
<213> ORGANISM: homo sapiens

<400> SEQUENCE: 10

| | | | | | |
|---|---|---|---|---|---|
| atggcctggg | ctccactact | tctcaccctc | ctcgctcact | gcacaggtgg | ctgcctgcaa | 60 |
| ggaattcagg | gagcgttcct | ggatgtcacc | tgggctgatg | atctgttcct | cctgcctggg | 120 |
| aaccagtctt | catctctccc | cactgatctc | tgtgttgctc | tcttcttgca | ggttcttggg | 180 |
| ccaattttat | gctgactcag | ccccactctg | tgtcggagtc | tccggggaag | acggtaacca | 240 |
| tctcctgcac | cggcagcagt | ggcagcattg | ccagcaacta | tgtgcagtgg | taccagcagc | 300 |
| gcccgggcag | tgcccccacc | actgtgatct | atgaggataa | ccaaagaccc | tctggggtcc | 360 |
| ctgatcggtt | ctctggctcc | atcgacagct | cctccaactc | tgcctccctc | accatctctg | 420 |
| gactgaagac | tgaggacgag | gctgactact | actgtcagtc | ttatgatagc | agcaatca | 478 |

<210> SEQ ID NO 11
<211> LENGTH: 296
<212> TYPE: DNA
<213> ORGANISM: Homo sapiens

<400> SEQUENCE: 11

| | | | | | |
|---|---|---|---|---|---|
| aattttatgc | tgactcagcc | ccactctgtg | tcggagtctc | cggggaagac | ggtaaccatc | 60 |
| tcctgcaccg | gcagcagtgg | cagcattgcc | agcaactatg | tgcagtggta | ccagcagcgc | 120 |
| ccgggcagtg | cccccaccac | tgtgatctat | gaggataacc | aaagaccctc | tggggtccct | 180 |
| gatcggttct | ctggctccat | cgacagctcc | tccaactctg | cctccctcac | catctctgga | 240 |
| ctgaagactg | aggacgaggc | tgactactac | tgtcagtctt | atgatagcag | caatca | 296 |

<210> SEQ ID NO 12
<211> LENGTH: 98
<212> TYPE: PRT
<213> ORGANISM: Homo sapiens

<400> SEQUENCE: 12

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn

<210> SEQ ID NO 13
<211> LENGTH: 462
<212> TYPE: DNA
<213> ORGANISM: homo sapiens

<400> SEQUENCE: 13

```
atgacctgct cccctctcct cctcacccctt ctcattcact gcacaggtgc ccagacacag    60
ggtcagggga ggggtccagg aagcccatga ggccctgctt tctccttctc tctctagacc   120
aagaatcacc gtgtctgtgt ctctcctgct tccagggtcc tgggcccagt ctgtgttgac   180
gcagccgccc tcagtgtctg cggccccagg acagaaggtc accatctcct gctctggaag   240
cagctccaac attgggaata attatgtatc ctggtaccag cagctcccag gaacagcccc   300
caaactcctc atttatgaca ataataagcg accctcaggg attcctgacc gattctctgg   360
ctccaagtct ggcacgtcag ccacccctggg catcaccgga ctccagactg gggacgaggc   420
cgattattac tgcggaacat gggatagcag cctgagtgct gg                      462
```

<210> SEQ ID NO 14
<211> LENGTH: 296
<212> TYPE: DNA
<213> ORGANISM: Homo sapiens

<400> SEQUENCE: 14

```
cagtctgtgt tgacgcagcc gccctcagtg tctgcggccc caggacagaa ggtcaccatc    60
tcctgctctg gaagcagctc caacattggg aataattatg tatcctggta ccagcagctc   120
ccaggaacag ccccaaaact cctcatttat gacaataata gcgaccctc agggattcct   180
gaccgattct ctggctccaa gtctggcacg tcagccaccc tgggcatcac cggactccag   240
actggggacg aggccgatta ttactgcgga acatgggata gcagcctgag tgctgg       296
```

<210> SEQ ID NO 15
<211> LENGTH: 99
<212> TYPE: PRT
<213> ORGANISM: Homo sapiens

<400> SEQUENCE: 15

```
Gln Ser Val Leu Thr Gln Pro Pro Ser Val Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly
```

<210> SEQ ID NO 16
<211> LENGTH: 466
<212> TYPE: DNA
<213> ORGANISM: homo spaiens

<400> SEQUENCE: 16

```
atggcctggt ctcctctcct cctcactctc ctcgctcact gcacaggtga ctggatacag    60
gtccagggga ggggccctgg gaagccctatg gattcttgct ttctcctgtt gtctctagaa   120
gccgaataat gatgcctgtg tctctcccac ttccagggtc ctgggcccag tctgtgctga   180
cgcagccgcc ctcagtgtct ggggccccag ggcagagggt caccatctcc tgcactggga   240
```

```
gcagctccaa catcggggca ggttatgatg tacactggta ccagcagctt ccaggaacag    300
cccccaaact cctcatctat ggtaacagca atcggccctc aggggtccct gaccgattct    360
ctggctccaa gtctggcacc tcagcctccc tggccatcac tgggctccag gctgaggatg    420
aggctgatta ttactgccag tcctatgaca gcagcctgag tggttc                   466
```

<210> SEQ ID NO 17
<211> LENGTH: 299
<212> TYPE: DNA
<213> ORGANISM: Homo sapiens

<400> SEQUENCE: 17

```
cagtctgtgc tgacgcagcc gccctcagtg tctggggccc cagggcagag ggtcaccatc    60
tcctgcactg ggagcagctc caacatcggg gcaggttatg atgtacactg gtaccagcag   120
cttccaggaa cagcccccaa actcctcatc tatggtaaca gcaatcggcc ctcaggggtc   180
cctgaccgat ctctggctcc aagtctggca cctcagcct cctggccat cactgggctc    240 caggctgagg atgaggctga ttattactgc cagtcctatg acagcagcct gagtggttc    299
```

<210> SEQ ID NO 18
<211> LENGTH: 100
<212> TYPE: PRT
<213> ORGANISM: Homo sapiens

<400> SEQUENCE: 18

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser
            100
```

<210> SEQ ID NO 19
<211> LENGTH: 468
<212> TYPE: DNA
<213> ORGANISM: homo sapiens

<400> SEQUENCE: 19

```
atggccagct ccctctcct cctcacccct ctcactcact gtgcaggtga caggatgggg    60
accaagaaag gggccctggg aagcccatgg ggccctgctt ctcctcttg tctccttttg   120 tctcttgtca atcaccatgt ctgtgtctct ctcacttcca gggtcctggg cccagtctgt   180
gctgactcag ccaccctcag cgtctgggac cccgggcag aggtcacca tctcttgttc    240 tggaagcagc tccaacatcg gaagtaatac tgtaaactgg taccagcagc tcccaggaac    300 ggccccaaa ctcctcatct atagtaataa tcagcggccc tcaggggtcc ctgaccgatt    360
ctctggctcc aagtctggca cctcagcctc cctggccatc agtgggctcc agtctgagga    420
tgaggctgat tattactgtg cagcatggga tgacagcctg aatggtcc                468
```

<210> SEQ ID NO 20
<211> LENGTH: 296
<212> TYPE: DNA
<213> ORGANISM: Homo sapiens

<400> SEQUENCE: 20

```
cagtctgtgc tgactcagcc accctcagcg tctgggaccc ccgggcagag ggtcaccatc      60
tcttgttctg gaagcagctc caacatcgga agtaatactg taaactggta ccagcagctc     120
ccaggaacgg cccccaaact cctcatctat agtaataatc agcggccctc aggggtccct     180
gaccgattct ctggctccaa gtctggcacc tcagcctccc tggccatcag tgggctccag     240
tctgaggatg aggctgatta ttactgtgca gcatgggatg acagcctgaa tggtcc         296
```

<210> SEQ ID NO 21
<211> LENGTH: 99
<212> TYPE: PRT
<213> ORGANISM: Homo sapiens

<400> SEQUENCE: 21

```
Gln Ser Val Leu Thr Gln Pro Pro Ser Ala Ser Gly Thr Pro Gly Gln
 1               5                  10                  15
Arg Val Thr Ile Ser Cys Ser Gly Ser Ser Asn Ile Gly Ser Asn
            20                  25                  30
Thr Val Asn Trp Tyr Gln Gln Leu Pro Gly Thr Ala Pro Lys Leu Leu
        35                  40                  45
Ile Tyr Ser Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
Asn Gly Pro
```

<210> SEQ ID NO 22
<211> LENGTH: 468
<212> TYPE: DNA
<213> ORGANISM: homo sapiens

<400> SEQUENCE: 22

```
atggccggct ccctctcct cctcaccctc ctcactcact gtgcaggtga caggatgggg       60
accaagagag gggccctggg aagcccatgg ggccctgctt ctcctcttg tctcctttcg      120
tctcttgtca atcaccatgt ctgtgtctct ctcacttcca gggtcctggg cccagtctgt     180
gctgactcag ccaccctcag cgtctgggac cccgggcag agggtcacca tctcttgttc      240
tggaagcagc tccaacatcg gaagtaatta tgtatactgg taccagcagc tcccaggaac    300
ggcccccaaa ctcctcatct atagtaataa tcagcggccc tcaggggtcc ctgaccgatt     360
ctctggctcc aagtctggca cctcagcctc cctggccatc agtgggctcc ggtccgagga    420
tgaggctgat tattactgtg cagcatggga tgacagcctg agtggtcc                 468
```

<210> SEQ ID NO 23
<211> LENGTH: 296
<212> TYPE: DNA
<213> ORGANISM: Homo sapiens

<400> SEQUENCE: 23

```
cagtctgtgc tgactcagcc accctcagcg tctgggaccc ccgggcagag ggtcaccatc    60
tcttgttctg gaagcagctc caacatcgga agtaattatg tatactggta ccagcagctc   120
ccaggaacgg ccccaaaact cctcatctat agtaataatc agcggccctc aggggtccct   180
gaccgattct ctggctccaa gtctggcacc tcagcctccc tggccatcag tgggctccgg   240
tccgaggatg aggctgatta ttactgtgca gcatgggatg acagcctgag tggtcc       296
```

<210> SEQ ID NO 24
<211> LENGTH: 99
<212> TYPE: PRT
<213> ORGANISM: Homo sapiens

<400> SEQUENCE: 24

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro
```

<210> SEQ ID NO 25
<211> LENGTH: 493
<212> TYPE: DNA
<213> ORGANISM: homo sapiens

<400> SEQUENCE: 25

```
atggcctgga cccctctctg gctcactctc ctcactcttt gcataggtgc tgcctcccag    60
ggctcaaccc catattatca tgctagctgt gccaacctgg ccctgagctt cggctcaaca   120 caggagtag tgtagggtgt gggactctag gcgtgaaacc cttatcctca cctcttctgt   180
cctcttttgc aggttctgtg gtttcttctg agctgactca ggaccctgct gtgtctgtgg   240
ccttgggaca gacagtcagg atcacatgcc aaggagacag cctcagaagc tattatgcaa   300
gctggtacca gcagaagcca ggacaggccc ctgtacttgt catctatggt aaaaacaacc   360
ggccctcagg gatcccagac cgattctctg ctccagctc aggaaacaca gcttccttga   420
ccatcactgg gctcaggcg gaagatgagg ctgactatta ctgtaactcc cggacagca    480 gtggtaacca tct                                                       493
```

<210> SEQ ID NO 26
<211> LENGTH: 290
<212> TYPE: DNA
<213> ORGANISM: Homo sapiens

<400> SEQUENCE: 26

```
tcttctgagc tgactcagga ccctgctgtg tctgtggcct tgggacagac agtcaggatc    60
acatgccaag gagacagcct cagaagctat tatgcaagct ggtaccagca gaagccagga   120
caggcccctg tacttgtcat ctatggtaaa aacaaccggc cctcagggat cccagaccga   180
ttctctggct ccagctcagg aaacacagct tccttgacca tcactggggc tcaggcggaa   240
```
gatgaggctg actattactg taactcccgg gacagcagtg gtaaccatct                  290

<210> SEQ ID NO 27
<211> LENGTH: 97
<212> TYPE: PRT
<213> ORGANISM: Homo sapiens

<400> SEQUENCE: 27

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu

<210> SEQ ID NO 28
<211> LENGTH: 15
<212> TYPE: PRT
<213> ORGANISM: Artificial Sequence
<220> FEATURE:
<223> OTHER INFORMATION: Peptide linker

<400> SEQUENCE: 28

Gly Gly Gly Gly Ser Gly Gly Gly Gly Ser Gly Gly Gly Gly Ser
1               5                   10                  15

<210> SEQ ID NO 29
<211> LENGTH: 8
<212> TYPE: PRT
<213> ORGANISM: Artificial Sequence
<220> FEATURE:
<223> OTHER INFORMATION: CDR Variant Sequence 1
<220> FEATURE:
<221> NAME/KEY: VARIANT
<222> LOCATION: (1)..(3)
<223> OTHER INFORMATION: X is any amino acid other than Trp, Gln, Lys,
      Glu, Met
<220> FEATURE:
<221> NAME/KEY: VARIANT
<222> LOCATION: (6)..(8)
<223> OTHER INFORMATION: X is any amino acid other than Trp, Gln, Lys,
      Glu, Met

<400> SEQUENCE: 29

Xaa Xaa Xaa Gly Gly Xaa Xaa Xaa
1               5

<210> SEQ ID NO 30
<211> LENGTH: 7
<212> TYPE: PRT
<213> ORGANISM: Artificial Sequence
<220> FEATURE:
<223> OTHER INFORMATION: CDR Variant Sequence
<220> FEATURE:
<221> NAME/KEY: VARIANT
<222> LOCATION: (1)..(3)
<223> OTHER INFORMATION: X is any amino acid other than Trp, Gln, Lys,
      Glu, Met

```
<220> FEATURE:
<221> NAME/KEY: VARIANT
<222> LOCATION: (5)..(7)
<223> OTHER INFORMATION: X is any amino acid other than Trp, Gln, Lys,
      Glu, Met

<400> SEQUENCE: 30

Xaa Xaa Xaa Gly Xaa Xaa Xaa
1               5

<210> SEQ ID NO 31
<211> LENGTH: 23
<212> TYPE: DNA
<213> ORGANISM: Artificial Sequence
<220> FEATURE:
<223> OTHER INFORMATION: HVK1F1

<400> SEQUENCE: 31
gacatccaga tgacccagtc tcc                                              23

<210> SEQ ID NO 32
<211> LENGTH: 23
<212> TYPE: DNA
<213> ORGANISM: Artificial Sequence
<220> FEATURE:
<223> OTHER INFORMATION: HVK1 F2

<400> SEQUENCE: 32
gmcatccrgw tgacccagtc tcc                                              23

<210> SEQ ID NO 33
<211> LENGTH: 23
<212> TYPE: DNA
<213> ORGANISM: Artificial Sequence
<220> FEATURE:
<223> OTHER INFORMATION: HVK2 F

<400> SEQUENCE: 33
gatrttgtga tgacycagwc tcc                                              23

<210> SEQ ID NO 34
<211> LENGTH: 23
<212> TYPE: DNA
<213> ORGANISM: Artificial Sequence
<220> FEATURE:
<223> OTHER INFORMATION: HVK 3F

<400> SEQUENCE: 34
gaaatwgtgw tgacrcagtc tcc                                              23

<210> SEQ ID NO 35
<211> LENGTH: 23
<212> TYPE: DNA
<213> ORGANISM: Artificial Sequence
<220> FEATURE:
<223> OTHER INFORMATION: HVK4 F

<400> SEQUENCE: 35
gacatcgtga tgacccagtc tcc                                              23

<210> SEQ ID NO 36
<211> LENGTH: 23
<212> TYPE: DNA
<213> ORGANISM: Artificial Sequence
<220> FEATURE:
<223> OTHER INFORMATION: HVK5 F
```

```
<400> SEQUENCE: 36
gaaacgacac tcacgcagtc tcc                                              23

<210> SEQ ID NO 37
<211> LENGTH: 23
<212> TYPE: DNA
<213> ORGANISM: Artificial Sequence
<220> FEATURE:
<223> OTHER INFORMATION: HVK6 F

<400> SEQUENCE: 37
gawrttgtgm tgacwcagtc tcc                                              23

<210> SEQ ID NO 38
<211> LENGTH: 24
<212> TYPE: DNA
<213> ORGANISM: Artificial Sequence
<220> FEATURE:
<223> OTHER INFORMATION: HVKCL R

<400> SEQUENCE: 38
acactctccc ctgttgaagc tctt                                             24

<210> SEQ ID NO 39
<211> LENGTH: 23
<212> TYPE: DNA
<213> ORGANISM: Artificial Sequence
<220> FEATURE:
<223> OTHER INFORMATION: HVL1 F1

<400> SEQUENCE: 39
cagtctgtgc tgactcagcc acc                                              23

<210> SEQ ID NO 40
<211> LENGTH: 23
<212> TYPE: DNA
<213> ORGANISM: Artificial Sequence
<220> FEATURE:
<223> OTHER INFORMATION: HVL1 F2

<400> SEQUENCE: 40
cagtctgtgy tgacgcagcc gcc                                              23

<210> SEQ ID NO 41
<211> LENGTH: 21
<212> TYPE: DNA
<213> ORGANISM: Artificial Sequence
<220> FEATURE:
<223> OTHER INFORMATION: HVL2F

<400> SEQUENCE: 41
cagtctgccc tgactcagcc t                                                21

<210> SEQ ID NO 42
<211> LENGTH: 23
<212> TYPE: DNA
<213> ORGANISM: Artificial Sequence
<220> FEATURE:
<223> OTHER INFORMATION: HVL3 F1

<400> SEQUENCE: 42
tcctatgwgc tgacwcagcc acc                                              23

<210> SEQ ID NO 43
<211> LENGTH: 23
```

<210> SEQ ID NO 43
<211> LENGTH: 23
<212> TYPE: DNA
<213> ORGANISM: Artificial Sequence
<220> FEATURE:
<223> OTHER INFORMATION: HVL3 F2

<400> SEQUENCE: 43
tcttctgagc tgactcagga ccc                                            23

<210> SEQ ID NO 44
<211> LENGTH: 21
<212> TYPE: DNA
<213> ORGANISM: Artificial Sequence
<220> FEATURE:
<223> OTHER INFORMATION: HVL4 F1

<400> SEQUENCE: 44
ctgcctgtgc tgactcagcc c                                              21

<210> SEQ ID NO 45
<211> LENGTH: 23
<212> TYPE: DNA
<213> ORGANISM: Artificial Sequence
<220> FEATURE:
<223> OTHER INFORMATION: HVL4 F2

<400> SEQUENCE: 45
cagcytgtgc tgactcaatc ryc                                            23

<210> SEQ ID NO 46
<211> LENGTH: 20
<212> TYPE: DNA
<213> ORGANISM: Artificial Sequence
<220> FEATURE:
<223> OTHER INFORMATION: HVL5F

<400> SEQUENCE: 46
cagsctgtgc tgactcagcc                                                20

<210> SEQ ID NO 47
<211> LENGTH: 23
<212> TYPE: DNA
<213> ORGANISM: Artificial Sequence
<220> FEATURE:
<223> OTHER INFORMATION: HVL6 F

<400> SEQUENCE: 47
aattttatgc tgactcagcc cca                                            23

<210> SEQ ID NO 48
<211> LENGTH: 23
<212> TYPE: DNA
<213> ORGANISM: Artificial Sequence
<220> FEATURE:
<223> OTHER INFORMATION: HVL7/8F

<400> SEQUENCE: 48
cagrctgtgg tgacycagga gcc                                            23

<210> SEQ ID NO 49
<211> LENGTH: 23
<212> TYPE: DNA
<213> ORGANISM: Artificial Sequence
<220> FEATURE:
<223> OTHER INFORMATION: HVL9/10F

<400> SEQUENCE: 49
cagscwgkgc tgactcagcc acc					23

<210> SEQ ID NO 50
<211> LENGTH: 23
<212> TYPE: DNA
<213> ORGANISM: Artificial Sequence
<220> FEATURE:
<223> OTHER INFORMATION: 01115 HVLCL R

<400> SEQUENCE: 50
tgaacattct gtaggggcca ctg					23

<210> SEQ ID NO 51
<211> LENGTH: 23
<212> TYPE: DNA
<213> ORGANISM: Artificial Sequence
<220> FEATURE:
<223> OTHER INFORMATION: 01116 HVLCL R2

<400> SEQUENCE: 51
tgaacattcc gtaggggcaa ctg					23

<210> SEQ ID NO 52
<211> LENGTH: 42
<212> TYPE: DNA
<213> ORGANISM: Artificial Sequence
<220> FEATURE:
<223> OTHER INFORMATION: HVK1 2F1

<400> SEQUENCE: 52
atctagaatg ggagacggtg acatccagat gacccagtct cc					42

<210> SEQ ID NO 53
<211> LENGTH: 42
<212> TYPE: DNA
<213> ORGANISM: Artificial Sequence
<220> FEATURE:
<223> OTHER INFORMATION: HVK1 2F2

<400> SEQUENCE: 53
atctagaatg ggagacggtg mcatccrgwt gacccagtct cc					42

<210> SEQ ID NO 54
<211> LENGTH: 42
<212> TYPE: DNA
<213> ORGANISM: Artificial Sequence
<220> FEATURE:
<223> OTHER INFORMATION: HVK2 2F

<400> SEQUENCE: 54
atctagaatg ggagacggtg mcatccrgwt gacccagtct cc					42

<210> SEQ ID NO 55
<211> LENGTH: 42
<212> TYPE: DNA
<213> ORGANISM: Artificial Sequence
<220> FEATURE:
<223> OTHER INFORMATION: HVK3 2F

<400> SEQUENCE: 55
atctagaatg ggagacggtg aaatwgtgwt gacrcagtct cc					42

<210> SEQ ID NO 56
<211> LENGTH: 42
<212> TYPE: DNA
<213> ORGANISM: Artificial Sequence

```
<220> FEATURE:
<223> OTHER INFORMATION: HVK4 2F

<400> SEQUENCE: 56
atctagaatg ggagacggtg acatcgtgat gacccagtct cc                              42

<210> SEQ ID NO 57
<211> LENGTH: 42
<212> TYPE: DNA
<213> ORGANISM: Artificial Sequence
<220> FEATURE:
<223> OTHER INFORMATION: HVK5 2F

<400> SEQUENCE: 57
atctagaatg ggagacggtg aaacgacact cacgcagtct cc                              42

<210> SEQ ID NO 58
<211> LENGTH: 42
<212> TYPE: DNA
<213> ORGANISM: Artificial Sequence
<220> FEATURE:
<223> OTHER INFORMATION: HVK6 2F

<400> SEQUENCE: 58
atctagaatg ggagacggtg awrttgtgmt gacwcagtct cc                              42

<210> SEQ ID NO 59
<211> LENGTH: 51
<212> TYPE: DNA
<213> ORGANISM: Artificial Sequence
<220> FEATURE:
<223> OTHER INFORMATION: HVKCL 2R

<400> SEQUENCE: 59
gatcagggtc tgagacgatt trathtccas yykkgtccch bsgccraavg t                    51

<210> SEQ ID NO 60
<211> LENGTH: 42
<212> TYPE: DNA
<213> ORGANISM: Artificial Sequence
<220> FEATURE:
<223> OTHER INFORMATION: HVL1 2F1

<400> SEQUENCE: 60
atctagaatg ggagacggtc agtctgtgct gactcagcca cc                              42

<210> SEQ ID NO 61
<211> LENGTH: 42
<212> TYPE: DNA
<213> ORGANISM: Artificial Sequence
<220> FEATURE:
<223> OTHER INFORMATION: HVL1 2F2

<400> SEQUENCE: 61
atctagaatg ggagacggtc agtctgtgyt gacgcagccg cc                              42

<210> SEQ ID NO 62
<211> LENGTH: 40
<212> TYPE: DNA
<213> ORGANISM: Artificial Sequence
<220> FEATURE:
<223> OTHER INFORMATION: HVL2 2F

<400> SEQUENCE: 62
atctagaatg ggagacggtc agtctgccct gactcagcct                                 40
```

<210> SEQ ID NO 63
<211> LENGTH: 42
<212> TYPE: DNA
<213> ORGANISM: Artificial Sequence
<220> FEATURE:
<223> OTHER INFORMATION: HVL3 2F1

<400> SEQUENCE: 63
atctagaatg ggagacggtt cctatgwgct gacwcagcca cc          42

<210> SEQ ID NO 64
<211> LENGTH: 42
<212> TYPE: DNA
<213> ORGANISM: Artificial Sequence
<220> FEATURE:
<223> OTHER INFORMATION: HVL3 2F2

<400> SEQUENCE: 64
atctagaatg ggagacggtt cttctgagct gactcaggac cc          42

<210> SEQ ID NO 65
<211> LENGTH: 40
<212> TYPE: DNA
<213> ORGANISM: Artificial Sequence
<220> FEATURE:
<223> OTHER INFORMATION: HVL4 2F1

<400> SEQUENCE: 65
atctagaatg ggagacggtc tgcctgtgct gactcagccc             40

<210> SEQ ID NO 66
<211> LENGTH: 42
<212> TYPE: DNA
<213> ORGANISM: Artificial Sequence
<220> FEATURE:
<223> OTHER INFORMATION: HVL4 2F2

<400> SEQUENCE: 66
atctagaatg ggagacggtc agcytgtgct gactcaatcr yc          42

<210> SEQ ID NO 67
<211> LENGTH: 39
<212> TYPE: DNA
<213> ORGANISM: Artificial Sequence
<220> FEATURE:
<223> OTHER INFORMATION: HVL5 2F

<400> SEQUENCE: 67
atctagaatg ggagacggtc agsctgtgct gactcagcc              39

<210> SEQ ID NO 68
<211> LENGTH: 42
<212> TYPE: DNA
<213> ORGANISM: Artificial Sequence
<220> FEATURE:
<223> OTHER INFORMATION: HVL6 2F

<400> SEQUENCE: 68
atctagaatg ggagacggta attttatgct gactcagccc ca          42

<210> SEQ ID NO 69
<211> LENGTH: 42
<212> TYPE: DNA
<213> ORGANISM: Artificial Sequence
<220> FEATURE:
<223> OTHER INFORMATION: HVL7/8 2F

<400> SEQUENCE: 69
atctagaatg ggagacggtc agrctgtggt gacycaggag cc                                    42

<210> SEQ ID NO 70
<211> LENGTH: 42
<212> TYPE: DNA
<213> ORGANISM: Artificial Sequence
<220> FEATURE:
<223> OTHER INFORMATION: HVL9/10 2F

<400> SEQUENCE: 70
atctagaatg ggagacggtc agscwgkgct gactcagcca cc                                    42

<210> SEQ ID NO 71
<211> LENGTH: 48
<212> TYPE: DNA
<213> ORGANISM: Artificial Sequence
<220> FEATURE:
<223> OTHER INFORMATION: HVLCL 2R

<400> SEQUENCE: 71
gatcagggtc tgagacgarr ygrtsasctb sgtbcchbyd ccraabac                              48

<210> SEQ ID NO 72
<211> LENGTH: 11
<212> TYPE: PRT
<213> ORGANISM: Homo sapiens

<400> SEQUENCE: 72

Val Phe Gly Thr Gly Thr Lys Val Thr Val Ser
1               5                   10

<210> SEQ ID NO 73
<211> LENGTH: 11
<212> TYPE: PRT
<213> ORGANISM: Homo sapiens

<400> SEQUENCE: 73

Val Phe Gly Gly Gly Thr Lys Leu Thr Val Ser
1               5                   10

<210> SEQ ID NO 74
<211> LENGTH: 11
<212> TYPE: PRT
<213> ORGANISM: Homo sapiens

<400> SEQUENCE: 74

Val Phe Gly Gly Gly Thr Lys Leu Thr Val Ser
1               5                   10

<210> SEQ ID NO 75
<211> LENGTH: 11
<212> TYPE: PRT
<213> ORGANISM: Homo sapiens

<400> SEQUENCE: 75

Val Phe Gly Gly Gly Thr Gln Leu Ile Ile Ser
1               5                   10

<210> SEQ ID NO 76
<211> LENGTH: 11
<212> TYPE: PRT
<213> ORGANISM: Homo sapiens

<400> SEQUENCE: 76

Val Phe Gly Glu Gly Thr Glu Leu Thr Val Ser
1               5                   10

<210> SEQ ID NO 77
<211> LENGTH: 11
<212> TYPE: PRT
<213> ORGANISM: Homo sapiens

<400> SEQUENCE: 77

Val Phe Gly Ser Gly Thr Lys Val Thr Val Ser
1               5                   10

<210> SEQ ID NO 78
<211> LENGTH: 11
<212> TYPE: PRT
<213> ORGANISM: Homo sapiens

<400> SEQUENCE: 78

Val Phe Gly Gly Gly Thr Gln Leu Thr Ala Ser
1               5                   10

<210> SEQ ID NO 79
<211> LENGTH: 11
<212> TYPE: PRT
<213> ORGANISM: Homo sapiens

<400> SEQUENCE: 79

Val Phe Gly Thr Gly Thr Lys Leu Ile Ile Ser
1               5                   10

<210> SEQ ID NO 80
<211> LENGTH: 105
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t

<400> SEQUENCE: 80
gatcagggtc tgagacgaga ccgtcacttt cgtaccggtg ccgaacacca cagtannann      60
anntccgcca nnannanngt cccacgcctg acagtaatag tcagc                    105

<210> SEQ ID NO 81
<211> LENGTH: 31

```
<212> TYPE: PRT
<213> ORGANISM: Homo sapiens
<220> FEATURE:
<221> NAME/KEY: VARIANT
<222> LOCATION: (10)..(12)
<223> OTHER INFORMATION: X is any amino acid other than Trp, Gln, Lys,
      Glu, Met
<220> FEATURE:
<221> NAME/KEY: VARIANT
<222> LOCATION: (15)..(17)
<223> OTHER INFORMATION: X is any amino acid other than Trp, Gln, Lys,
      Glu, Met

<400> SEQUENCE: 81

Ala Asp Tyr Tyr Cys Gln Ala Trp Asp Xaa Xaa Xaa Gly Gly Xaa Xaa
1               5                   10                  15

Xaa Thr Val Val Phe Gly Thr Gly Thr Lys Val Thr Val Ser Ser
            20                  25                  30

<210> SEQ ID NO 82
<211> LENGTH: 105
<212> TYPE: DNA
<213> ORGANISM: Homo sapiens
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t

<400> SEQUENCE: 82
gatcagggtc tgagacccgc tgctcacggt aaccatggta ccttgacccc aaatatcaaa     60
cgcannanna nngccannan nannttttcgc acagtagtaa acagc                  105

<210> SEQ ID NO 83
<211> LENGTH: 25
<212> TYPE: PRT
<213> ORGANISM: Homo sapiens
<220> FEATURE:
<221> NAME/KEY: VARIANT
<222> LOCATION: (7)..(9)
<223> OTHER INFORMATION: X is any amino acid other than Trp, Gln, Lys,
      Glu, Met
<220> FEATURE:
<221> NAME/KEY: VARIANT
<222> LOCATION: (11)..(13)
<223> OTHER INFORMATION: X is any amino acid other than Trp, Gln, Lys,
      Glu, Met

<400> SEQUENCE: 83

Val Tyr Tyr Cys Ala Lys Xaa Xaa Xaa Gly Xaa Xaa Xaa Ala Phe Asp
1               5                   10                  15

Ile Trp Gly Gln Gly Thr Met Val Thr
```

<210> SEQ ID NO 84
<211> LENGTH: 771
<212> TYPE: DNA
<213> ORGANISM: Homo sapiens
<220> FEATURE:
<221> NAME/KEY: misc_feature
<222> LOCATION: (286)..(287)
<223> OTHER INFORMATION: n is a, c, g, or t
<220> FEATURE:
<221> NAME/KEY: misc_feature
<222> LOCATION: (289)..(290)
<223> OTHER INFORMATION: n is a, c, g, or t
<220> FEATURE:
<221> NAME/KEY: misc_feature
<222> LOCATION: (292)..(293)
<223> OTHER INFORMATION: n is a, c, g, or t
<220> FEATURE:
<221> NAME/KEY: misc_feature
<222> LOCATION: (301)..(302)
<223> OTHER INFORMATION: n is a, c, g, or t
<220> FEATURE:
<221> NAME/KEY: misc_feature
<222> LOCATION: (304)..(305)
<223> OTHER INFORMATION: n is a, c, g, or t
<220> FEATURE:
<221> NAME/KEY: misc_feature
<222> LOCATION: (307)..(308)
<223> OTHER INFORMATION: n is a, c, g, or t
<220> FEATURE:
<221> NAME/KEY: misc_feature
<222> LOCATION: (706)..(707)
<223> OTHER INFORMATION: n is a, c, g, or t
<220> FEATURE:
<221> NAME/KEY: misc_feature
<222> LOCATION: (709)..(710)
<223> OTHER INFORMATION: n is a, c, g, or t
<220> FEATURE:
<221> NAME/KEY: misc_feature
<222> LOCATION: (712)..(713)
<223> OTHER INFORMATION: n is a, c, g, or t
<220> FEATURE:
<221> NAME/KEY: misc_feature
<222> LOCATION: (718)..(719)
<223> OTHER INFORMATION: n is a, c, g, or t
<220> FEATURE:
<221> NAME/KEY: misc_feature
<222> LOCATION: (721)..(722)
<223> OTHER INFORMATION: n is a, c, g, or t
<220> FEATURE:
<221> NAME/KEY: misc_feature
<222> LOCATION: (724)..(725)
<223> OTHER INFORMATION: n is a, c, g, or t

<400> SEQUENCE: 84

```
atgggagacg gtcagtctgt gctgactcag ccaccctcag tgtccgtgtc cccaggacag    60
acagccagca tcacctgctc tggagataaa ttgggggata atatgcttg  ctggtatcag   120 cagaagccag gccagtcccc tgtgctggtc atctatcaag atagcaagcg gccctcaggg   180
atccctgagc gattctctgg ctccaactct gggaacacag ccactctgac catcagcggg   240
acccaggcta tggatgaggc tgactattac tgtcaggcgt gggacnntnn tnntggaggt   300
nntnntnnta ctgtggtgtt cggcacgggc accaagctca tcatttcgtc tcagaccggt   360
ggttctggtg gtggtggttc tggcggcggc ggctccggtg gtggtggatc cgaagtccaa   420
ctgctggagt ccggcggtgg cctggtgcag ccaggtggca gcctgcgcct gagctgcgcc   480
gcatccggtt ttactttcag cagctacgcg atgtcgtggg tgcgccaggc accgggcaag   540
ggcctggagt gggtcagcgc catcagcggt agcggcggtt ctacgtatta tgcggacagc   600
gtcaagggcc gttccaccat cagccgtgac aattccaaaa acaccctgta cttgcagatg   660
```

```
aacagcttgc gtgcggaaga tacggctgtt tactactgtg cgaaanntnn tnntggannt    720
nntnntgcct ttgatatttg gggtcaaggt accatggtta ccgtgagcag c             771
```

<210> SEQ ID NO 85
<211> LENGTH: 257
<212> TYPE: PRT
<213> ORGANISM: Homo sapiens
<220> FEATURE:
<221> NAME/KEY: misc_feature
<222> LOCATION: (96)..(98)
<223> OTHER INFORMATION: Xaa can be any naturally occurring amino acid
<220> FEATURE:
<221> NAME/KEY: misc_feature
<222> LOCATION: (101)..(103)
<223> OTHER INFORMATION: Xaa can be any naturally occurring amino acid
<220> FEATURE:
<221> NAME/KEY: misc_feature
<222> LOCATION: (236)..(238)
<223> OTHER INFORMATION: Xaa can be any naturally occurring amino acid
<220> FEATURE:
<221> NAME/KEY: misc_feature
<222> LOCATION: (240)..(242)
<223> OTHER INFORMATION: Xaa can be any naturally occurring amino acid

<400> SEQUENCE: 85

```
Met Gly Asp Gly Gln Ser Val Leu Thr Gln Pro Pro Ser Val Ser Val
1               5                   10                  15

Ser Pro Gly Gln Thr Ala Ser Ile Thr Cys Ser Gly Asp Lys Leu Gly
            20                  25                  30

Asp Lys Tyr Ala Cys Trp Tyr Gln Gln Lys Pro Gly Gln Ser Pro Val
        35                  40                  45

Leu Val Ile Tyr Gln Asp Ser Lys Arg Pro Ser Gly Ile Pro Glu Arg
    50                  55                  60

Phe Ser Gly Ser Asn Ser Gly Asn Thr Ala Thr Leu Thr Ile Ser Gly
65                  70                  75                  80

Thr Gln Ala Met Asp Glu Ala Asp Tyr Tyr Cys Gln Ala Trp Asp Xaa
                85                  90                  95

Xaa Xaa Gly Gly Xaa Xaa Xaa Thr Val Val Phe Gly Thr Gly Thr Lys
            100                 105                 110

Val Thr Val Ser Ser Gln Thr Gly Gly Ser Gly Gly Gly Ser Gly
        115                 120                 125

Gly Gly Gly Ser Gly Gly Gly Ser Glu Val Gln Leu Leu Glu Ser
    130                 135                 140

Gly Gly Gly Leu Val Gln Pro Gly Gly Ser Leu Arg Leu Ser Cys Ala
145                 150                 155                 160

Ala Ser Gly Phe Thr Phe Ser Ser Tyr Ala Met Ser Trp Val Arg Gln
                165                 170                 175

Ala Pro Gly Lys Gly Leu Glu Trp Val Ser Ala Ile Ser Gly Ser Gly
            180                 185                 190

Gly Ser Thr Tyr Tyr Ala Asp Ser Val Lys Gly Arg Phe Thr Ile Ser
        195                 200                 205

Arg Asp Asn Ser Lys Asn Thr Leu Tyr Leu Gln Met Asn Ser Leu Arg
    210                 215                 220

Ala Glu Asp Thr Ala Val Tyr Tyr Cys Ala Lys Xaa Xaa Xaa Gly Xaa
225                 230                 235                 240

Xaa Xaa Ala Phe Asp Ile Trp Gly Gln Gly Thr Met Val Thr Val Ser
                245                 250                 255

Ser
```

<210> SEQ ID NO 86
<211> LENGTH: 8
<212> TYPE: PRT
<213> ORGANISM: Homo sapiens
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 86

Xaa Xaa Xaa Gly Gly Xaa Xaa Xaa
1               5

<210> SEQ ID NO 87
<211> LENGTH: 7
<212> TYPE: PRT
<213> ORGANISM: Homo sapiens
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 87

Xaa Xaa Xaa Gly Xaa Xaa Xaa
1               5

<210> SEQ ID NO 88
<211> LENGTH: 361
<212> TYPE: DNA
<213> ORGANISM: Homo sapiens

<400> SEQUENCE: 88
atgggagacg gtcagtctgt gctgactcag ccaccctcag tgtccgtgtc cccaggacag      60
acagccagca tcacctgctc tggagataaa ttgggggata aatatgcttg ctggtatcag     120
cagaagccag gccagtcccc tgtgctggtc atctatcaag atagcaagcg gccctcaggg     180
atccctgagc gattctctgg ctccaactct gggaacacag ccactctgac catcagcggg     240
acccaggcta tggatgaggc tgactattac tgtcaggcgt gggactgaga cctagacggt     300
ctctgcgttt gatatttggg gtcaaggtac catggttacc gtgagcagct cgtctcagac     360
c                                                                    361

<210> SEQ ID NO 89
<211> LENGTH: 396
<212> TYPE: DNA
<213> ORGANISM: Homo sapiens

<400> SEQUENCE: 89
actgtggtgt tcggcaccgg tacgaaagtg actgtctcat ctcagaccgg tggttctggt      60
ggtggtggtt ctggcggcgg cggctccggt ggtggtggat ccgaagtcca actgctggag     120
tccggcggtg gcctggtgca gccaggtggc agcctgcgcc tgagctgcgc cgcatccggt     180
tttactttca gcagctacgc gatgtcgtgg gtgcgccagg caccgggcaa gggcctggag     240
tgggtcagcg ccatcagcgg tagcggcggt tctacgtatt atgcggacag cgtcaagggc     300
cgtttcacca tcagccgtga caattccaaa aacaccctgt acttgcagat gaacagcttg     360
cgtgcggaag atacggctgt ttactactgt gcgaaa                                    396

<210> SEQ ID NO 90
<211> LENGTH: 71
<212> TYPE: DNA
<213> ORGANISM: Homo sapiens
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 90
gatcagggtc tcaggacnnt nntnntggcg ganntnntnn tactgtggtg ttcggcaccg    60
gtacgaaagt g                                                         71

<210> SEQ ID NO 91
<211> LENGTH: 68
<212> TYPE: DNA
<213> ORGANISM: Homo sapiens
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 91
gatcagggtc tcaacgcann annanngcca nnannanntt tcgcacagta gtaaacagcc    60
gtatcttc                                                             68

<210> SEQ ID NO 92
<211> LENGTH: 8
<212> TYPE: PRT

```
<213> ORGANISM: Homo sapiens

<400> SEQUENCE: 92

Pro Phe Gly Gly Gly Gly Tyr Val
1               5

<210> SEQ ID NO 93
<211> LENGTH: 7
<212> TYPE: PRT
<213> ORGANISM: Homo sapiens

<400> SEQUENCE: 93

Pro Pro His Gly Ala Pro Ala
1               5

<210> SEQ ID NO 94
<211> LENGTH: 8
<212> TYPE: PRT
<213> ORGANISM: Homo sapiens

<400> SEQUENCE: 94

Leu Cys Ile Gly Gly Val Ala Ser
1               5

<210> SEQ ID NO 95
<211> LENGTH: 7
<212> TYPE: PRT
<213> ORGANISM: Homo sapiens

<400> SEQUENCE: 95

His Asn Ser Gly Asn Asn Phe
1               5

<210> SEQ ID NO 96
<211> LENGTH: 8
<212> TYPE: PRT
<213> ORGANISM: Homo sapiens

<400> SEQUENCE: 96

Phe Val Ser Gly Gly Ile Ser Thr
1               5

<210> SEQ ID NO 97
<211> LENGTH: 7
<212> TYPE: PRT
<213> ORGANISM: Homo sapiens

<400> SEQUENCE: 97

Phe Asn Phe Gly Asn Ala Tyr
1               5

<210> SEQ ID NO 98
<211> LENGTH: 8
<212> TYPE: PRT
<213> ORGANISM: Homo sapiens

<400> SEQUENCE: 98

Ile Asn Ser Gly Gly Ala Ser Phe
1               5

<210> SEQ ID NO 99
<211> LENGTH: 7
<212> TYPE: PRT
<213> ORGANISM: Homo sapiens
<220> FEATURE:
```

```
<221> NAME/KEY: misc_feature
<222> LOCATION: (1)..(3)
<223> OTHER INFORMATION: Xaa can be any naturally occurring amino acid

<400> SEQUENCE: 99

Xaa Xaa Xaa Gly Thr Asn Tyr
1               5

<210> SEQ ID NO 100
<211> LENGTH: 8
<212> TYPE: PRT
<213> ORGANISM: Homo sapiens

<400> SEQUENCE: 100

Ser Arg Ala Gly Gly Cys Asn Gly
1               5

<210> SEQ ID NO 101
<211> LENGTH: 7
<212> TYPE: PRT
<213> ORGANISM: Homo sapiens

<400> SEQUENCE: 101

Phe Asp Tyr Gly His Cys Ile
1               5

<210> SEQ ID NO 102
<211> LENGTH: 8
<212> TYPE: PRT
<213> ORGANISM: Homo sapiens

<400> SEQUENCE: 102

Thr Asn Arg Gly Gly Val Cys Ala
1               5

<210> SEQ ID NO 103
<211> LENGTH: 7
<212> TYPE: PRT
<213> ORGANISM: Homo sapiens

<400> SEQUENCE: 103

Thr Ala Ala Gly Val Pro Phe
1               5

<210> SEQ ID NO 104
<211> LENGTH: 8
<212> TYPE: PRT
<213> ORGANISM: Homo sapiens

<400> SEQUENCE: 104

Phe Ser Thr Gly Gly Cys Ala Phe
1               5

<210> SEQ ID NO 105
<211> LENGTH: 7
<212> TYPE: PRT
<213> ORGANISM: Homo sapiens

<400> SEQUENCE: 105

Ala Ile Cys Gly Ala Thr Ala
1               5

<210> SEQ ID NO 106
<211> LENGTH: 8
<212> TYPE: PRT
```

```
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 106

Phe Xaa Gly Gly Gly Asp Gly Thr
1               5

<210> SEQ ID NO 107
<211> LENGTH: 7
<212> TYPE: PRT
<213> ORGANISM: Homo sapiens

<400> SEQUENCE: 107

Pro Tyr Arg Gly Ser Phe Phe
1               5

<210> SEQ ID NO 108
<211> LENGTH: 8
<212> TYPE: PRT
<213> ORGANISM: Homo sapiens

<400> SEQUENCE: 108

Ile Ile Pro Gly Gly Leu Tyr Ala
1               5

<210> SEQ ID NO 109
<211> LENGTH: 7
<212> TYPE: PRT
<213> ORGANISM: Homo sapiens

<400> SEQUENCE: 109

Pro Val Ile Gly Ser Asn Thr
1               5

<210> SEQ ID NO 110
<211> LENGTH: 254
<212> TYPE: PRT
<213> ORGANISM: Aequorea victoria

<400> SEQUENCE: 110

Met Val Ser Val Ile Lys Pro Glu Met Lys Ile Lys Leu Cys Met Arg
1               5                   10                  15

Gly Thr Val Asn Gly His Asn Phe Val Ile Glu Gly Glu Gly Lys Gly
            20                  25                  30

Asn Pro Tyr Glu Gly Thr Gln Ile Leu Asp Leu Asn Val Thr Glu Gly
        35                  40                  45

Ala Pro Leu Pro Phe Ala Tyr Asp Ile Leu Thr Thr Val Phe Gln Tyr
    50                  55                  60

Gly Asn Arg Ala Phe Thr Lys Tyr Pro Ala Asp Ile Gln Asp Tyr Phe
65                  70                  75                  80

Lys Gln Thr Phe Pro Glu Gly Tyr His Trp Glu Arg Ser Met Thr Tyr
                85                  90                  95

Glu Asp Gln Gly Ile Cys Thr Ala Thr Ser Asn Ile Ser Met Arg Gly
            100                 105                 110

Asp Cys Phe Phe Tyr Asp Ile Arg Phe Asp Gly Thr Asn Phe Pro Pro
        115                 120                 125

Asn Gly Pro Val Met Gln Lys Lys Thr Leu Lys Trp Glu Pro Ser Thr
    130                 135                 140
```

```
Glu Lys Met Tyr Val Glu Asp Gly Val Leu Lys Gly Asp Val Asn Met
145                 150                 155                 160

Arg Leu Leu Leu Glu Gly Gly His Tyr Arg Cys Asp Phe Lys Thr
                165                 170                 175

Thr Tyr Lys Ala Lys Lys Glu Val Arg Leu Pro Asp Ala His Lys Ile
            180                 185                 190

Asp His Arg Ile Glu Ile Leu Lys His Asp Lys Asp Tyr Asn Lys Val
                195                 200                 205

Lys Leu Tyr Glu Asn Ala Val Ala Arg Tyr Ser Met Leu Pro Ser Gln
            210                 215                 220

Ala Lys Ser Gly Gly Leu Asn Asp Ile Phe Glu Ala Gln Lys Ile Glu
225                 230                 235                 240

Trp His Glu Asp Thr Gly Gly Ser His His His His His
                245                 250
```

<210> SEQ ID NO 111
<211> LENGTH: 266
<212> TYPE: PRT
<213> ORGANISM: Homo sapiens

<400> SEQUENCE: 111

```
Met Gly Asp Gly Gln Ser Val Leu Thr Gln Pro Pro Ser Val Ser Val
1               5                   10                  15

Ser Pro Gly Gln Thr Ala Ser Ile Thr Cys Ser Gly Asp Lys Leu Gly
            20                  25                  30

Asp Lys Tyr Ala Cys Trp Tyr Gln Gln Lys Pro Gly Gln Ser Pro Val
            35                  40                  45

Leu Val Ile Tyr Gln Asp Ser Lys Arg Pro Ser Gly Ile Pro Glu Arg
50                  55                  60

Phe Ser Gly Ser Asn Ser Gly Asn Thr Ala Thr Leu Thr Ile Ser Gly
65                  70                  75                  80

Thr Gln Ala Met Asp Glu Ala Asp Tyr Tyr Cys Gln Ala Trp Asp Phe
                85                  90                  95

Asn Leu Gly Gly Cys Gly Asp Thr Val Val Phe Gly Thr Gly Thr Lys
            100                 105                 110

Val Thr Val Ser Ser Gln Thr Gly Gly Ser Gly Gly Gly Ser Gly
            115                 120                 125

Gly Gly Gly Ser Gly Gly Gly Ser Glu Val Gln Leu Leu Glu Ser
        130                 135                 140

Gly Gly Gly Leu Val Gln Pro Gly Gly Ser Leu Arg Leu Ser Cys Ala
145                 150                 155                 160

Ala Ser Gly Phe Thr Phe Ser Ser Tyr Ala Met Ser Trp Val Arg Gln
                165                 170                 175

Ala Pro Gly Lys Gly Leu Glu Trp Val Ser Ala Ile Ser Gly Ser Gly
            180                 185                 190

Gly Ser Thr Tyr Tyr Ala Asp Ser Val Lys Gly Arg Phe Thr Ile Ser
            195                 200                 205

Arg Asp Asn Ser Lys Asn Thr Leu Tyr Leu Gln Met Asn Ser Leu Arg
        210                 215                 220

Ala Glu Asp Thr Ala Val Tyr Tyr Cys Ala Lys His Ile Asp Gly Pro
225                 230                 235                 240

Val Ala Ala Phe Asp Ile Trp Gly Gln Gly Thr Met Val Thr Val Ser
                245                 250                 255

Ser Ser Ser Gln Thr Ser Ile Leu Val Ala
            260                 265
```

<210> SEQ ID NO 112
<211> LENGTH: 1176
<212> TYPE: DNA
<213> ORGANISM: Artificial Sequence
<220> FEATURE:
<223> OTHER INFORMATION: Fusion construct

<400> SEQUENCE: 112

```
atgacgagca agaaaccctt taccccattac cagccgcagg gcaacagtga cccggctcat      60
accgcaaccg cgcccggcgg attgagtgcg aaagcgcctg caatgacccc gctgatgctg     120
gacacctcca gccgtaagct ggttgcgtgg atggcacca ccgacggtgc tgccgttggc      180
attcttgcgg ttgctgctga ccagaccagc accacgctga cgttctacaa gtccggcacg     240
ttccgttatg aggatgtgct ctggccgag gctgccagcg acgagacgaa aaacggacc       300
gcgtttgccg aacggcaat cagcatcgtt ggaggtagcg gcggatcgga tgacgacgat      360
aagtctagaa atggcggaga cggtcagtct gtgctgactc agccaccctc agtgtccgtg     420
tccccaggac agacagccag catcacctgc tctggagata aattggggga taaatatgct     480
tgctggtatc agcagaagcc aggccagtcc cctgtgctgg tcatctatca agatagcaag     540
cggccctcag ggatccctga gcgattctct ggctccaact ctgggaacac agccactctg     600
accatcagcg ggacccaggc tatggatgag gctgactatt actgtcaggc gtgggacttt    660
aatcttggcg gatgtggtga tactgtggtg ttcggcaccg gtacgaaagt gactgtctca    720
tctcagaccg tggttctgg tggcggtggt tctggcggcg gcggctccgg tggtggtgga    780
tccgaagtcc aactgctgga gtccggtggt ggcctggtgc agccaggtgg cagcctgcgc    840
ctgagctgcg ccgcatccgg ttttacttc agcagctacg cgatgtcgtg ggtgcgccag    900
gcaccgggca agggcctgga gtgggtcagc gccatcagcg gtagcggcgg ttctacgtat    960
tatgcggaca cgtcaagggg ccgtttcacc atcagccgtg acaattccaa aaacaccctg   1020
tacttgcaga tgaacagctt gcgtgcggaa gatacggctg tttactactg tgcgaaacat   1080
attgatggcc ctgttgctgc gtttgatatt tgggggtcaag gtaccatggt taccgtgagc   1140
aactcgagcg attacaagga cgatgatgac aaataa                             1176
```

<210> SEQ ID NO 113
<211> LENGTH: 391
<212> TYPE: PRT
<213> ORGANISM: Artificial Sequence
<220> FEATURE:
<223> OTHER INFORMATION: Fusion protein

<400> SEQUENCE: 113

```
Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95
```

```
Lys Lys Arg Thr Ala Phe Ala Gly Thr Ala Ile Ser Ile Val Gly Gly
                100                 105                 110

Ser Gly Gly Ser Asp Asp Asp Lys Ser Arg Asn Gly Gly Asp Gly
        115                 120                 125

Gln Ser Val Leu Thr Gln Pro Pro Ser Val Ser Val Ser Pro Gly Gln
        130                 135                 140

Thr Ala Ser Ile Thr Cys Ser Gly Asp Lys Leu Gly Asp Lys Tyr Ala
145                 150                 155                 160

Cys Trp Tyr Gln Gln Lys Pro Gly Gln Ser Pro Val Leu Val Ile Tyr
                165                 170                 175

Gln Asp Ser Lys Arg Pro Ser Gly Ile Pro Glu Arg Phe Ser Gly Ser
        180                 185                 190

Asn Ser Gly Asn Thr Ala Thr Leu Thr Ile Ser Gly Thr Gln Ala Met
        195                 200                 205

Asp Glu Ala Asp Tyr Tyr Cys Gln Ala Trp Asp Phe Asn Leu Gly Gly
        210                 215                 220

Cys Gly Asp Thr Val Val Phe Gly Thr Gly Thr Lys Val Thr Val Ser
225                 230                 235                 240

Ser Gln Thr Gly Gly Ser Gly Gly Gly Ser Gly Gly Gly Gly Ser
                245                 250                 255

Gly Gly Gly Gly Ser Glu Val Gln Leu Leu Glu Ser Gly Gly Gly Leu
        260                 265                 270

Val Gln Pro Gly Gly Ser Leu Arg Leu Ser Cys Ala Ala Ser Gly Phe
        275                 280                 285

Thr Phe Ser Ser Tyr Ala Met Ser Trp Val Arg Gln Ala Pro Gly Lys
        290                 295                 300

Gly Leu Glu Trp Val Ser Ala Ile Ser Gly Ser Gly Gly Ser Thr Tyr
305                 310                 315                 320

Tyr Ala Asp Ser Val Lys Gly Arg Phe Thr Ile Ser Arg Asp Asn Ser
                325                 330                 335

Lys Asn Thr Leu Tyr Leu Gln Met Asn Ser Leu Arg Ala Glu Asp Thr
        340                 345                 350

Ala Val Tyr Tyr Cys Ala Lys His Ile Asp Gly Pro Val Ala Ala Phe
        355                 360                 365

Asp Ile Trp Gly Gln Gly Thr Met Val Thr Val Ser Asn Ser Ser Asp
        370                 375                 380

Tyr Lys Asp Asp Asp Lys
385                 390

<210> SEQ ID NO 114
<211> LENGTH: 89
<212> TYPE: PRT
<213> ORGANISM: Homo sapiens

<400> SEQUENCE: 114

Gln Ser Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
                20                  25                  30

Cys Trp Tyr Gln Gln Lys Pro Gly Gln Ser Pro Val Leu Val Ile Tyr
                35                  40                  45

Gln Asp Ser Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65              70                  75                  80
```

```
Asp Glu Ala Asp Tyr Tyr Cys Gln Ala
                85

<210> SEQ ID NO 115
<211> LENGTH: 93
<212> TYPE: PRT
<213> ORGANISM: Homo sapiens

<400> SEQUENCE: 115

Met Gly Asp Gly Gln Ser Val Leu Thr Gln Pro Ser Val Ser Val
1               5                   10                  15

Ser Pro Gly Gln Thr Ala Ser Ile Thr Cys Ser Gly Asp Lys Leu Gly
                20                  25                  30

Asp Lys Tyr Ala Cys Trp Tyr Gln Gln Lys Pro Gly Gln Ser Pro Val
            35                  40                  45

Leu Val Ile Tyr Gln Asp Ser Lys Arg Pro Ser Gly Ile Pro Glu Arg
        50                  55                  60

Phe Ser Gly Ser Asn Ser Gly Asn Thr Ala Thr Leu Thr Ile Ser Gly
65                  70                  75                  80

Thr Gln Ala Met Asp Glu Ala Asp Tyr Tyr Cys Gln Ala
                85                  90

<210> SEQ ID NO 116
<211> LENGTH: 93
<212> TYPE: PRT
<213> ORGANISM: Homo sapiens

<400> SEQUENCE: 116

Met Gly Asp Gly Gln Ser Val Leu Thr Gln Pro Ser Val Ser Val
1               5                   10                  15

Ser Pro Gly Gln Thr Ala Ser Ile Thr Cys Ser Gly Asp Lys Leu Gly
                20                  25                  30

Asp Lys Tyr Ala Cys Trp Tyr Gln Gln Lys Pro Gly Gln Ser Pro Val
            35                  40                  45

Leu Val Ile Tyr Gln Asp Ser Lys Arg Pro Ser Gly Ile Pro Glu Arg
        50                  55                  60

Phe Ser Gly Ser Asn Ser Gly Asn Thr Ala Thr Leu Thr Ile Ser Gly
65                  70                  75                  80

Thr Gln Ala Met Asp Glu Ala His Tyr Tyr Cys Gln Thr
                85                  90

<210> SEQ ID NO 117
<211> LENGTH: 93
<212> TYPE: PRT
<213> ORGANISM: Homo sapiens

<400> SEQUENCE: 117

Met Gly Asp Gly Gln Ser Val Leu Thr Gln Pro Ser Val Ser Val
1               5                   10                  15

Ser Pro Gly Gln Thr Ala Thr Ile Thr Cys Ser Gly Asp Lys Leu Gly
                20                  25                  30

Asp Lys Phe Ala Cys Trp Tyr Gln Gln Lys Pro Gly Gln Ser Pro Val
            35                  40                  45

Leu Val Ile Tyr Gln Asp Tyr Gln Arg Pro Ser Gly Ile Pro Glu Arg
        50                  55                  60

Phe Ser Gly Ser Asn Ser Gly Asn Thr Ala Thr Leu Thr Ile Ser Gly
65                  70                  75                  80
```

Thr Gln Val Met Asp Glu Ala Asp Tyr Tyr Cys Gln Ala
            85                  90

<210> SEQ ID NO 118
<211> LENGTH: 87
<212> TYPE: PRT
<213> ORGANISM: Homo sapiens
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid

<400> SEQUENCE: 118

Met Gly Asp Gly Gln Ser Val Leu Thr Gln Pro Ala Val Ser Val
1               5                   10                  15

Ala Pro Glu Lys Thr Ala Thr Ile Ala Cys Gly Gly Asn Arg Ile Gly
                20                  25                  30

Ser Lys Ser Val His Trp Tyr Gln Xaa Lys Pro Gly Gln Ala Pro Val
            35                  40                  45

Leu Val Ile Tyr Asn Asp Asn Asp Arg Pro Ser Gly Xaa Pro Glu Arg
        50                  55                  60

Phe Ser Gly Ser Asn Ser Gly Asn Thr Ala Thr Leu Thr Ile Ser Arg
65                  70                  75                  80

Val Glu Val Gly Asp Glu Ala
                85

<210> SEQ ID NO 119
<211> LENGTH: 87
<212> TYPE: PRT
<213> ORGANISM: Homo sapiens

<400> SEQUENCE: 119

Met Gly Asp Gly Gln Ser Val Leu Thr Gln Pro Ser Val Ser Val
1               5                   10                  15

Ala Pro Gly Lys Thr Ala Thr Ile Ala Cys Gly Gly Asn Arg Ile Gly
                20                  25                  30

Ser Lys Ser Val His Trp Tyr Gln Gln Lys Pro Gly Gln Ala Pro Val
            35                  40                  45

Leu Val Ile Tyr Asn Asp Asn Asp Arg Pro Ser Gly Ile Pro Glu Arg
        50                  55                  60

Phe Ser Gly Ser Asn Ser Gly Asn Thr Ala Thr Leu Thr Ile Ser Arg
65                  70                  75                  80

Val Glu Val Gly Asp Glu Ala
                85

<210> SEQ ID NO 120
<211> LENGTH: 83
<212> TYPE: PRT
<213> ORGANISM: Homo sapiens

<400> SEQUENCE: 120

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
            35                  40                  45

```
Tyr Asp Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala

<210> SEQ ID NO 121
<211> LENGTH: 87
<212> TYPE: PRT
<213> ORGANISM: Homo sapiens

<400> SEQUENCE: 121

Met Gly Asp Gly Gln Ser Val Leu Thr Gln Pro Pro Ser Val Ser Val
  1               5                  10                  15

Ala Pro Gly Lys Thr Ala Thr Ile Thr Cys Gly Gly Asn Asn Ile Glu
                 20                  25                  30

Asp Lys Ser Val His Trp Tyr Gln Gln Lys Pro Gly Gln Ala Pro Val
             35                  40                  45

Leu Val Ile Tyr Tyr Asp Thr Asp Arg Pro Ser Gly Ile Pro Glu Arg
         50                  55                  60

Phe Ser Gly Ser Asn Ser Gly Asn Thr Ala Thr Leu Thr Ile Asn Arg
 65                  70                  75                  80

Val Glu Ala Gly Asp Glu Ala
                 85

<210> SEQ ID NO 122
<211> LENGTH: 95
<212> TYPE: PRT
<213> ORGANISM: Homo sapiens

<400> SEQUENCE: 122

Asn Phe Met Leu Thr Gln Pro His Ser Val Ser Glu Ser Pro Gly Lys
  1               5                  10                  15

Thr Val Thr Ile Ser Cys Thr Gly Ser Ser Gly Ser Ile Ala Ser Asn
                 20                  25                  30

Tyr Val Gln Trp Tyr Gln Gln Arg Pro Gly Ser Ala Pro Thr Thr Val
             35                  40                  45

Ile Tyr Glu Asp Asn Gln Arg Pro Ser Gly Val Pro Asp Arg Phe Ser
         50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp
                 85                  90                  95

<210> SEQ ID NO 123
<211> LENGTH: 99
<212> TYPE: PRT
<213> ORGANISM: Homo sapiens

<400> SEQUENCE: 123

Met Gly Asp Gly Asn Phe Met Leu Thr Gln Pro His Ser Val Ser Glu
  1               5                  10                  15

Ser Pro Gly Lys Thr Val Thr Ile Pro Cys Thr Gly Ser Ser Gly Ser
                 20                  25                  30

Ile Ala Ser Asn Tyr Val Gln Trp Tyr Gln Gln Arg Pro Gly Ser Ala
             35                  40                  45

Pro Thr Thr Val Ile Tyr Glu Asp Lys Gln Lys Pro Ser Gly Val Pro
```

```
                    50                  55                  60
Asp Arg Phe Ser Gly Ser Ile Asp Ser Ser Asn Ser Ala Ser Leu
 65                  70                  75                  80

Thr Ile Ser Gly Leu Lys Thr Glu Asp Glu Ala Asp Tyr Tyr Cys Gln
                 85                  90                  95

Ser Tyr Asp

<210> SEQ ID NO 124
<211> LENGTH: 99
<212> TYPE: PRT
<213> ORGANISM: Homo sapiens

<400> SEQUENCE: 124

Met Gly Asp Gly Asn Phe Met Leu Thr Gln Pro His Ser Val Ser Glu
 1               5                  10                  15

Ser Pro Gly Lys Thr Val Thr Ile Ser Cys Thr Gly Ser Ser Gly Ser
                20                  25                  30

Ile Ala Ser Asn Ser Val Gln Arg Tyr Gln Gln Arg Pro Gly Ser Ala
            35                  40                  45

Pro Thr Thr Val Ile Tyr Glu Asp Asn Arg Arg Pro Ser Gly Val Pro
        50                  55                  60

Asp Arg Phe Ser Gly Ser Ile Asp Ser Ser Asn Ser Ala Ser Leu
 65                  70                  75                  80

Ile Ile Ser Gly Leu Gln Thr Glu Asp Glu Ala Asp Tyr Tyr Cys Gln
                 85                  90                  95

Ser Tyr Asp

<210> SEQ ID NO 125
<211> LENGTH: 99
<212> TYPE: PRT
<213> ORGANISM: Homo sapiens

<400> SEQUENCE: 125

Met Gly Asp Gly Asn Phe Met Leu Thr Gln Pro His Ser Val Ser Glu
 1               5                  10                  15

Ser Pro Gly Lys Thr Val Thr Ile Ser Cys Thr Gly Arg Ser Gly Ser
                20                  25                  30

Ile Ala Asp Asn Tyr Val Gln Trp Tyr Gln Gln Arg Pro Gly Ser Val
            35                  40                  45

Pro Thr Ser Val Ile Phe Glu Asp Asn Gln Arg Pro Ser Gly Val Pro
        50                  55                  60

Glu Arg Phe Ser Gly Ser Ile Asp Ser Ser Asn Ser Ala Ser Leu
 65                  70                  75                  80

Thr Ile Ser Gly Leu Met Thr Glu Asp Glu Ala Asp Tyr His Cys Gln
                 85                  90                  95

Ser Tyr Asp
```